(12) United States Patent
Tanabe et al.

(10) Patent No.: US 8,143,022 B2
(45) Date of Patent: Mar. 27, 2012

(54) HIGH PRODUCTION SYSTEM FOR INFECTIOUS HEPATITIS C VIRUS PARTICLE

(75) Inventors: Jun-ichi Tanabe, Kanagawa (JP); Saburo Sone, Kanagawa (JP); Takaji Wakita, Tokyo (JP); Koji Ishii, Tokyo (JP); Ryosuke Suzuki, Chiba (JP); Tetsuro Suzuki, Tokyo (JP); Tatsuo Miyamura, Tokyo (JP)

(73) Assignee: Tokyo Metropolitan Institute of Medical Science, Tokyo (JP)

( * ) Notice: Subject to any disclaimer, the term of this patent is extended or adjusted under 35 U.S.C. 154(b) by 779 days.

(21) Appl. No.: 11/992,837

(22) PCT Filed: Sep. 29, 2006

(86) PCT No.: PCT/JP2006/319572
§ 371 (c)(1), (2), (4) Date: Mar. 28, 2008

(87) PCT Pub. No.: WO2007/037428
PCT Pub. Date: Apr. 5, 2007

(65) Prior Publication Data
US 2010/0035345 A1    Feb. 11, 2010

(30) Foreign Application Priority Data
Sep. 30, 2005  (JP) .................................. 2005-287646

(51) Int. Cl.
C12P 21/00 (2006.01)
C12N 7/00 (2006.01)
C12N 5/22 (2006.01)

(52) U.S. Cl. .................... 435/69.1; 435/70.3; 435/235.1; 435/320.1; 435/325; 435/370

(58) Field of Classification Search ................. 435/325, 435/370, 69.1, 70.3, 235.1, 320.1
See application file for complete search history.

(56) References Cited

FOREIGN PATENT DOCUMENTS
| | | |
|---|---|---|
| JP | 2001-17187 A | 1/2001 |
| WO | WO 2004/104198 A1 | 12/2004 |
| WO | WO-2005/080575 A1 | 9/2005 |

OTHER PUBLICATIONS

Lindenbach et al. (2005) Science, vol. 309, 623-626.*
Heller et al. (2005) PNAS, vol. 102(7), 2579-2583.*
Lim et al. (2002) Virology, vol. 303, 79-99.*
Neumann et al. (1999) PNAS, vol. 96, 9345-9350.*
Blight et al., Science Magazine, vol. 290, pp. 1972-1974, (2000).
Friebe et al., Journal of Virology, vol. 75, No. 24, pp. 12047-12057, (2001).
Kato et al., Gastroenterology, vol. 125, pp. 1808-1817, (2003).
Lim et al., Virology, vol. 303, pp. 79-99, (2002).
Theo et al., Proceedings of the National Academy of Sciences of the USA, vol. 102, No. 7, pp. 2579-2583, (2005).
Shinagawa et al., Genes and Development, vol. 17, pp. 1340-1345, (2003).
Wakita at al., Nature Medicine, vol. 11, No. 7, pp. 791-796, (2005).
Pietschmann et al., 11th International Symposium on Hepatitis C Virus and Related Diseases, (2004).
Blight et al., Journal of Virology, vol. 64, No. 24, pp. 13001-13014, (2002).
Neumann et al., Virology, vol. 202, pp. 477-479, (1994).
Lindenbach et al., "Complete replication of hepatitis C virus in cell culture", Science, Jul. 2005, vol. 309, pp. 623-626.
Fodor et al., "Rescue of influenza a virus from recombinant DNA", J. Virol., 1999, vol. 73, pp. 9679-9682.
Neumann et al., Generation of influenza A viruses entirely from cloned cDNAs, Proc. Natl. Acad. Sci. USA, 1999, vol. 96, pp. 9345-9350.

* cited by examiner

Primary Examiner — Anne Marie S Wehbe
(74) Attorney, Agent, or Firm — Birch, Stewart, Kolasch & Birch, LLP

(57) ABSTRACT

The present invention relates to a method for producing infectious hepatitis C virus (HCV) particles, comprising a step of introducing an expression vector into a cell that allows HCV proliferation, such expression vector comprising: DNA sequences encoding the 5' untranslated region, structural proteins, and, if necessary, non-structural proteins of HCV and DNA sequences encoding non-structural proteins and the 3' untranslated region derived from the HCV JFH1 strain, which are located downstream of a polymerase I promoter; and a DNA fragment containing an RNA polymerase I terminator, which is located further downstream thereof.

5 Claims, 27 Drawing Sheets
(5 of 27 Drawing Sheet(s) Filed in Color)

Fig.10A

DNA sequence of the insert J6(C-p7)JFH1 acctgccctaatagggcgacactccgccatgaatcactccctgtgaggaactactgtcttcacgcagaaa
gcgcctagccatggcgttagtatgagtgtcgtacagcctccaggccccccctcccgggagagccatagtggt
ctgcggaaccggtgagtacaccggaattgccgggaagactgggtcctttcttggataaacccactctatgccc
ggccatttgggcgtgccccgcaagactgctagccgagtagcgttgggttgcgaaaggccttgtggtactgcc
tgatagggtgcttgcgagtgccccgggaggtctcgtagaccgtgcaccatgagcacaaatcctaaacctcaa
agaaaaaccaaaagaaacaccaaccgtcgcccacaagacgttaagtttccgggcggcggccagatcgttgg
cggagtatacttgttgccgcgcaggggccccaggttgggtgtgcgcgcgacaaggaagacttcggagcggtc
ccagccacgtggaaggcgccagcccatccctaaagatcggcgctccactggcaaatcctggggaaaaccag
gatacccctggcccctatacgggaatgagggactcggctgggcaggatggctcctgtcccccgaggttcccg
tccctcttggggccccaatgaccccggcataggtcgcgcaacgtgggtaaggtcatcgataccctaacgtgc
ggctttgccgacctcatggggtacatccctgtcgtgggcgccccgctcggcggcgtcgccagagctctcgcgca
tggcgtgagagtcctggaggacggggttaattttgcaacagggaacttacccggttgctccttttctatcttctt
gctggccctgctgtcctgcatcaccaccccggtctccgctgccgaagtgaagaacatcagtaccggctacatgg
tgactaacgactgcaccaatgacagcattacctggcagctccaggctgctgtcctccacgtccccgggtgcgtc
ccgtgcgagaaagtggggaatgcatctcagtgctggataccggtctcaccgaatgtggccgtgcagcggccc
ggcgccctcacgcagggcttgcggacgcacatcgacatggttgtgatgtccgccacgctctgctctgccctcta
cgtgggggacctctgcggtggggtgatgctcgcagcccaaatgttcattgtctcgccgcagcaccactggtttg
tccaagactgcaattgctccatctaccctggtaccatcactggacaccgcatggcatgggacatgatgatgaa
ctggtcgcccacggctaccatgatcttggcgtacgcgatgcgtgtccccgaggtcattatagacatcattagcg
gggctcattggggcgtcatgttcggcttggcctacttctctatgcagggagcgtgggcgaaagtcgttgtcatc
cttctgttggccgccggggtggacgcgcgcacccatactgttggggttctgccgcgcagaccaccgggcgcct
caccagcttatttgacatgggccccaggcagaaaatccagctcgttaacaccaatggcagctggcacatcaa
ccgcaccgccctgaactgcaatgactccttgcacaccggctttatcgcgtctctgttctacacccacagcttcaa
ctcgtcaggatgtcccgaacgcatgtccgcctgccgcagtatcgaggccttccgggtgggatggggcgccttg
caatatgaggataatgtcaccaatccagaggatatgagacccattgctggcactacccaccaaggcagtgt
ggcgtggtctccgcgaagactgtgtgtggcccagtgtactgtttcacccccagcccagtggtagtgggcacga
ccgacaggcttggagcgcccacttacacgtggggggagaatgagacagatgtcttcctattgaacagcactc
gaccaccgctggggtcatggttcggctgcacgtggatgaactcttctggctacaccaagacttgcggcgcacc
accctgccgtactagagctgacttcaacgccagcacggacctgttgtgccccacggactgttttaggaagcat
cctgataccacttacctcaaatgcggctctgggccctggctcacgccaaggtgcctgatcgactacccctacag
gctctggcattacccctgcacagttaactataccatcttcaaaataaggatgtatgtgggaggggttgagcac
aggctcacggctgcatgcaatttcactcgtggggatcgttgcaacttggaggacagagacagaagtcaactg
tctcctttgttgcactccaccacggaatgggccatttttaccttgctcttactcggacctgccgccttgtcgactg
gtcttctccacctccaccaaaacatcgtggacgtacaattcatgtatggcctatcacctgccctcacaaaatac

Fig.10B atcgtccgatgggagtgggtaatactcttattcctgctcttagcggacgccagggtttgcgcctgcttatggat
gctcatcttgttgggccaggccgaagcagcactagagaagctggtcatcttgcacgctgcgagcgcagctag
ctgcaatggcttcctatattttgtcatcttttcgtggctgcttggtacatcaagggtcgggtagtccccttagct
acctattccctcactggcctgtggtcctttagcctactgctcctagcattgccccaacaggcttatgcttatgacg
catctgtgcatggccagataggagcggctctgctggtaatgatcaccctcttcacactcaccccggggtataa
gaccctcctcggccagtgtctgtggtggttgtgctatctcctgaccctgggggaagccatgattcaggagtggg
taccacccatgcaggtgcgcggcggccgcgatggcatcgcgtgggccgtcactatattctgcccgggtgtggt
gtttgacattaccaaatggcttttggcgttgcttgggcctgcttacctcttaagggccgctttgacacatgtgcc
gtacttcgtcagagctcacgctctgataagggtatgcgctttggtgaagcagctcgcggggggtaggtatgtt
caggtggcgctattggcccttggcaggtggactggcacctacatctatgaccacctcacacctatgtcggactg
ggccgctagcggcctgcgcgacttagcggtcgccgtggaacccatcatcttcagtccgatggagaagaaggt
catcgtctggggagcggagacggctgcatgtggggacattctacatggacttcccgtgtccgcccgactcggc
caggagatcctcctcggcccagctgatggctacacctccaaggggtggaagctccttgctcccatcactgctta
tgcccagcaaacacgaggcctcctgggcgccatagtggtgagtatgacggggcgtgacaggacagaacag
gccggggaagtccaaatcctgtccacagtctctcagtccttcctcggaacaaccatctcgggggttttgtggac
tgtttaccacggagctggcaacaagactctagccggcttacggggtccggtcacgcagatgtactcgagtgct
gagggggacttggtaggctggcccagccccctgggaccaagtctttggagccgtgcaagtgtggagccgtc
gacctatatctggtcacgcggaacgctgatgtcatcccggctcggagacgcggggacaagcggggagcattg
ctctccccgagacccatttcgaccttgaaggggtcctcggggggccggtgctctgccctaggggccacgtcgt
tgggctcttccgagcagctgtgtgctctcggggcgtggccaaatccatcgatttcatcccgttgagacactcg
acgttgttacaaggtctcccactttcagtgacaacagcacgccaccggctgtgccccagacctatcaggtcgg
gtacttgcatgctccaactggcagtggaaagagcaccaaggtccctgtcgcgtatgccgcccaggggtacaa
agtactagtgcttaaccctcggtagctgccaccctggggtttggggcgtacctatccaaggcacatggcatc
aatcccaacattaggactggagtcaggaccgtgatgaccggggaggccatcacgtactccacatatggcaa
atttctcgccgatggggctgcgctagcggcgcctatgacatcatcatatgcgatgaatgccacgctgtggat
gctacctccattctcggcatcggaacggtccttgatcaagcagagacagccggggtcagactaactgtgctgg
ctacggccacaccccccgggtcagtgacaaccccccatcccgatatagaagaggtaggcctcgggcgggagg
gtgagatccccttctatgggagggcgattcccctatcctgcatcaagggagggagacacctgattttctgccac
tcaaagaaaaagtgtgacgagctcgcggcggcccttcggggcatgggcttgaatgccgtggcatactatag
agggttggacgtctccataataccagctcagggagatgtggtggtcgtcgccaccgacgccctcatgacggg
gtacactggagactttgactccgtgatcgactgcaatgtagcggtcacccaagctgtcgacttcagcctggac
cccaccttcactataaccacacagactgtcccacaagacgctgtctcacgcagtcagcgccgcggcgcacag
gtagaggaagacagggcacttataggtatgtttccactggtgaacgagcctcaggaatgtttgacagtgtag
tgctttgtgagtgctacgacgcaggggctgcgtggtacgatctcacaccagcggagaccaccgtcaggcttag
agcgtatttcaacacgcccggcctacccgtgtgtcaagaccatcttgaattttgggaggcagttttcaccggcc
tcacacacatagacgcccacttcctctcccaaacaaagcaagcgggggagaacttcgcgtacctagtagcct

Fig.10C accaagctacggtgtgcgccagagccaaggcccctcccccgtcctgggacgccatgtggaagtgcctggcccg
actcaagcctacgcttgcgggccccacacctctcctgtaccgtttgggccctattaccaatgaggtcaccctcac
acaccctgggacgaagtacatcgccacatgcatgcaagctgaccttgaggtcatgaccagcacgtgggtcct
agctggaggagtcctggcagccgtcgccgcatattgcctggcgactggatgcgtttccatcatcggccgcttgc
acgtcaaccagcgagtcgtcgttgcgccggataaggaggtcctgtatgaggcttttgatgagatggaggaat
gcgcctctagggcggctctcatcgaagaggggcagcggatagccgagatgttgaagtccaagatccaaggc
ttgctgcagcaggcctctaagcaggcccaggacatacaacccgctatgcaggcttcatggcccaaagtggaa
caattttgggccagacacatgtggaacttcattagcggcatccaatacctcgcaggattgtcaacactgccag
ggaaccccgcggtggcttccatgatggcattcagtgccgccctcaccagtccgttgtcgaccagtaccaccatc
cttctcaacatcatgggaggctggttagcgtcccagatcgcaccaccgcgggggccaccggctttgtcgtcag
tggcctggtgggggctgccgtgggcagcataggcctgggtaaggtgctggtggacatcctggcaggatatgg
tgcgggcatttcgggggccctcgtcgcattcaagatcatgtctggcgagaagccctctatggaagatgtcatc
aatctactgcctgggatcctgtctccgggagccctggtggtgggggtcatctgcgcggccattctgcgccgcca
cgtgggaccgggggagggcgcggtccaatggatgaacaggcttattgcctttgcttccagaggaaaccacgt
cgcccctactcactacgtgacggagtcggatgcgtcgcagcgtgtgacccaactacttggctctcttactataa
ccagcctactcagaagactccacaattggataactgaggactgccccatcccatgctccggatcctggctccgc
gacgtgtgggactgggtttgcaccatcttgacagacttcaaaaattggctgacctctaaattgttccccaagct
gcccggcctcccccttcatctcttgtcaaaaggggtacaagggtgtgtgggccggcactggcatcatgaccacg
cgctgcccttgcggcgccaacatctctggcaatgtccgcctgggctctatgaggatcacagggcctaaaacct
gcatgaacacctggcaggggacctttcctatcaattgctacacggagggccagtgcgcgccgaaaccccca
cgaactacaagaccgccatctggagggtggcggcctcggagtacgcggaggtgacgcagcatgggtcgtac
tcctatgtaacaggactgaccactgacaatctgaaaattccttgccaactaccttctccagagttttctcctgg
gtggacggtgtgcagatccataggtttgcacccacaccaaagccgttttccgggatgaggtctcgttctgcgt
tgggcttaattcctatgctgtcgggtcccagcttccctgtgaacctgagcccgacgcagacgtattgaggtcca
tgctaacagatccgccccacatcacggcggagactgcggcgcggcgcttggcacggggatcacctccatctga
ggcgagctcctcagtgagccagctatcagcaccgtcgctgcgggccacctgcaccacccacagcaacacctat
gacgtggacatggtcgatgccaacctgctcatggagggcggtgtggctcagacagagcctgagtccagggtg
cccgttctggactttctcgagccaatggccgaggaagagagcgaccttgagccctcaataccatcggagtgca
tgctccccaggagcgggtttccacgggccttaccggcttgggcacggcctgactacaacccgccgctcgtgga
atcgtggaggaggccagattaccaaccgccaccgttgctggttgtgctctccccccccccaagaaggccccg
acgcctcccccaaggagacgccggacagtgggtctgagcgagagcaccatatcagaagccctccagcaact
ggccatcaagacctttggccagccccctcgagcggtgatgcaggctcgtccacgggggcgggcgccgccga
atccggcggtccgacgtcccctggtgagccggccccctcagagacaggttccgcctcctctatgcccccctcga
gggggagcctggagatccggacctggagtctgatcaggtagagcttcaacctccccccaggggggggggg
tagctcccggttcgggctcggggtcttggtctacttgctccgaggaggacgataccacgtgtgctgctccatg
tcatactcctggaccggggctctaataactccctgtagccccgaagaggaaaagttgccaatcaaccctttga

Fig.10D gtaactcgctgttgcgataccataacaaggtgtactgtacaacatcaaagagcgcctcacagagggctaaa
aaggtaacttttgacaggacgcaagtgctcgacgcccattatgactcagtcttaaaggacatcaagctagcg
gcttccaaggtcagcgcaaggctcctcaccttggaggaggcgtgccagttgactccaccccattctgcaagat
ccaagtatggattcggggccaaggaggtccgcagcttgtccgggagggccgttaaccacatcaagtccgtgt
ggaaggacctcctggaagacccacaaacaccaattccacaaccatcatggccaaaaatgaggtgttctgc
gtggaccccgccaaggggggtaagaaaccagctcgcctcatcgtttaccctgacctcggcgtccgggtctgcg
agaaaatggccctctatgacattacacaaaagcttcctcaggcggtaatgggagcttcctatggcttccagta
ctcccctgcccaacgggtggagtatctcttgaaagcatgggcggaaaagaaggaccccatgggttttcgtat
gatacccgatgcttcgactcaaccgtcactgagagagacatcaggaccgaggagtccatataccaggcctgc
tccctgcccgaggaggcccgcactgccatacactcgctgactgagagactttacgtaggagggcccatgttca
acagcaagggtcaaacctgcggttacagacgttgccgcgccagcggggtgctaaccactagcatgggtaac
accatcacatgctatgtgaaagccctagcggcctgcaaggctgcggggatagttgcgcccacaatgctggta
tgcggcgatgacctagtagtcatctcagaaagccaggggactgaggaggacgagcggaacctgagagcctt
cacggaggccatgaccaggtactctgccctcctggtgatcccccagaccggaatatgacctggagctaata
acatcctgttcctcaaatgtgtctgtggcgttgggcccgcggggccgccgcagatactacctgaccagagacc
caaccactccactcgccgggctgcctgggaaacagttagacactcccctatcaattcatggctgggaaacat
catccagtatgctccaaccatatgggttcgcatggtcctaatgacacacttcttctccattctcatggtccaaga
caccctggaccagaacctcaactttgagatgtatggatcagtatactccgtgaatcctttggaccttccagcca
taattgagaggttacacgggcttgacgccttttctatgcacacatactctcaccacgaactgacgcgggtggct
tcagccctcagaaaacttgggcgccaccctcagggtgtggaagagtcgggctcgcgcagtcagggcgtcc
ctcatctcccgtggagggaaagcggccgtttgcggccgatatctcttcaattgggcggtgaagaccaagctca
aactcactccattgccggaggcgcgcctactggacttatccagttggttcaccgtcggcgccggcggggcga
catttttcacagcgtgtcgcgcgcccgaccccgctcattactcttcggcctactcctacttttcgtaggggtaggc
ctcttcctactccccgctcggtagagcggcacacactaggtacactccatagctaactgttcctttttttttttttt
ttttttttttttttttttttttttttctttttttttttttttccctctttcttcccttctcatcttattctactttctttcttg
gtggctccatcttagccctagtcacggctagctgtgaaaggtccgtgagccgcatgactgcagagagtgccgt
aactggtctctctgcagatcatgt

Fig.11A

DNA sequence of the insert H77c(C-p7)JFH1 acctgcccctaatagggcgacactccgccatgaatcactcccctgtgaggaactactgtcttcacgcagaaa
gcgcctagccatggcgttagtatgagtgtcgtacagcctccaggccccccctcccgggagagccatagtggt
ctgcggaaccggtgagtacaccggaattgccaggacgaccgggtcctttcttggataaacccgctcaatgcct
ggagatttgggcgtgccccgcaagactgctagccgagtagtgttgggtcgcgaaaggccttgtggtactgcc
tgatagggtgcttgcgagtgccccgggaggtctcgtagaccgtgcaccatgagcacgaatcctaaacctcaa
agaaaaaccaaacgtaacaccaaccgtcgcccacaggacgtcaagttcccgggtggcggtcagatcgttgg
tggagtttacttgttgccgcgcaggggccctagattgggtgtgcgcgcgacgaggaagacttccgagcggtc
gcaacctcgaggtagacgtcagcctatccccaaggcacgtcggcccgagggcaggacctgggctcagcccgg
gtaccettggcccctctatggcaatgagggttgcgggtgggcgggatggctcctgtctccccgtggctctcggc
ctagctggggccccacagaccccggcgtaggtcgcgcaatttgggtaaggtcatcgataccettacgtgcgg
cttcgccgacctcatggggtacataccgctcgtcggcgcccctcttggaggcgctgccagggccctggcgcatg
gcgtccgggttctggaagacggcgtgaactatgcaacagggaaccttcctggttgctctttctctatcttccttc
tggccctgctctcttgcctgactgtgcccgcttcagcctaccaagtgcgcaattcctcggggctttaccatgtcac
caatgattgccctaactcgagtattgtgtacgaggcggccgatgccatcctgcacactccggggtgtgtcccttt
gcgttcgcgagggtaacgctcgaggtgttgggtggcggtgaccccacggtggccaccagggacggcaaa
ctccccacaacgcagcttcgacgtcatatcgatctgcttgtcgggagcgccaccctctgctcggccctctacgtg
ggggacctgtgcgggtctgtctttcttgttggtcaactgtttaccttctctcccaggcgccactggacgacgcaa
gactgcaattgttctatctatcccggccatataacgggtcatcgcatggcatgggatatgatgatgaactggt
cccctacggcagcgttggtggtagctcagctgctccggatcccacaagccatcatggacatgatcgctggtgct
cactggggagtcctggcgggcatagcgtatttctccatggtggggaactgggcgaaggtcctggtagtgctgc
tgctatttgccggcgtcgacgcggaaacccacgtcaccgggggaaatgccggccgcaccacggctgggcttgt
tggtctccttacaccaggcgccaagcagaacatccaactgatcaacaccaacggcagttggcacatcaatag
cacggccttgaattgcaatgaaagccttaacaccggctggttagcagggctcttctatcaacacaaattcaac
tcttcaggctgtcctgagaggttggccagctgccgacgccttaccgattttgcccagggctggggtcctatcag
ttatgccaacggaagcggcctcgacgaacgcccctactgctggcactaccctccaagaccttgtggcattgtgc
ccgcaaagagcgtgtgtggcccggtatattgcttcactcccagccccgtggtggtgggaacgaccgacaggtc
gggcgcgcctacctacagctggggtgcaaatgatacggatgtcttcgtccttaacaacacaggccaccgctg
ggcaattggttcggttgtacctggatgaactcaactggattcaccaaagtgtgcggagcgcccccttgtgtcat
cggaggggtgggcaacaacaccttgctctgccccactgattgcttccgcaaacatccggaagccacatactct
cggtgcggctccggtcctggattacacccaggtgcatggtcgactaccegtataggctttggcactatccttgt
accatcaattacaccatattcaaagtcaggatgtacgtgggagggggtcgagcacaggctggaagcggcctg
caactggacgcggggcgaacgctgtgatctggaagacagggacaggtccgagctcagcccgttgctgctgtc
caccacacagtggcaggtccttccgtgttctttcacgaccctgccagccttgtccaccggcctcatccacctccac
cagaacattgtggacgtgcagtacttgtacggggtagggtcaagcatcgcgtcctgggccattaagtgggag

Fig.11B tacgtcgttctcctgttccttctgcttgcagacgcgcgcgtctgctcctgcttgtggatgatgttactcatatccca
agcggaggcggctttggagaacctcgtaatactcaatgcagcatccctggccgggacgcacggtcttgtgtcc
ttcctcgtgttcttctgctttgcgtggtatctgaagggtaggtgggtgcccggagcggtctacgccctctacggg
atgtggcctctcctcctgctcctgctggcgttgcctcagcgggcatacgcatatgacgcacctgtgcacggaca
gataggcgtgggtttgttgatattgatcaccctcttcacactcaccccggggtataagaccctcctcggccagt
gtctgtggtggttgtgctatctcctgaccctgggggaagccatgattcaggagtgggtaccacccatgcaggt
gcgcggcggccgcgatggcatcgcgtgggccgtcactatattctgcccgggtgtggtgtttgacattaccaaat
ggcttttggcgttgcttgggcctgcttacctcttaagggccgctttgacacatgtgccgtacttcgtcagagctc
acgctctgataagggtatgcgctttggtgaagcagctcgcggggggtaggtatgttcaggtggcgctattggc
ccttggcaggtggactggcacctacatctatgaccacctcacacctatgtcggactgggccgctagcggcctgc
gcgacttagcggtcgccgtggaacccatcatcttcagtccgatggagaagaaggtcatcgtctggggagcgg
agacggctgcatgtggggacattctacatggacttcccgtgtccgcccgactcggccaggagatcctcctcggc
ccagctgatggctacacctccaaggggtggaagctccttgctcccatcactgcttatgccagcaaacacgag
gcctcctgggcgccatagtggtgagtatgacggggcgtgacaggacagaacaggccggggaagtccaaatc
ctgtccacagtctctcagtccttcctcggaacaaccatctcgggggttttgtggactgtttaccacggagctggc
aacaagactctagccggcttacggggtccggtcacgcagatgtactcgagtgctgagggggacttggtaggc
tggcccagccccctgggaccaagtctttggagccgtgcaagtgtggagccgtcgacctatatctggtcacgc
ggaacgctgatgtcatcccggctcggagacgcggggacaagcggggagcattgctctccccgagacccattt
cgaccttgaaggggtcctcgggggggccggtgctctgccctaggggccacgtcgttgggctcttccgagcagc
tgtgtgctctcggggcgtggccaaatccatcgatttcatccccgttgagacactcgacgttgttacaaggtctcc
cactttcagtgacaacagcacgccaccggctgtgccccagacctatcaggtcgggtacttgcatgctccaactg
gcagtggaaagagcaccaaggtccctgtcgcgtatgccgcccaggggtacaaagtactagtgcttaaccctt
cggtagctgccacccctgggtttgggcgtacctatccaaggcacatggcatcaatcccaacattaggactgg
agtcaggaccgtgatgaccggggaggccatcacgtactccacatatggcaaatttctcgccgatggggctg
cgctagcggcgcctatgacatcatatatgcgatgaatgccacgctgtggatgctacctccattctcggcatcg
gaacggtccttgatcaagcagagacagccggggtcagactaactgtgctggctacggccacaccccccgggt
cagtgacaaccccccatcccgatatagaagaggtaggcctcgggcgggagggtgagatccccttctatggga
gggcgattccccatcctgcatcaagggagggagacacctgattttctgccactcaaagaaaaagtgtgacg
agctcgcggcggcccttcggggcatgggcttgaatgccgtggcatactatagagggttggacgtctccataat
accagctcagggagatgtggtggtcgtcgccaccgacgccctcatgacggggtacactggagactttgactcc
gtgatcgactgcaatgtagcggtcacccaagctgtcgacttcagcctggacccaccttcactataaccacac
agactgtcccacaagacgctgtctcacgcagtcagcgccgggcgcacaggtagaggaagacagggcact
tataggtatgtttccactggtgaacgagcctcaggaatgtttgacagtgtagtgctttgtgagtgctacgacg
caggggctgcgtggtacgatctcacaccagcggagaccaccgtcaggcttagagcgtatttcaacacgcccg
gcctaccgtgtgtcaagaccatcttgaattttgggaggcagttttcaccggcctcacacacatagacgcccac
ttcctctcccaaacaaagcaagcgggggagaacttcgcgtacctagtagcctaccaagctacggtgtgcgcc

Fig.11C agagccaaggcccctcccccgtcctgggacgccatgtggaagtgcctggcccgactcaagcctacgcttgcgg
gccccacacctctcctgtaccgtttgggccctattaccaatgaggtcaccctcacacaccctgggacgaagtac
atcgccacatgcatgcaagctgaccttgaggtcatgaccagcacgtgggtcctagctggaggagtcctggca
gccgtcgccgcatattgcctggcgactggatgcgtttccatcatcggccgcttgcacgtcaaccagcgagtcgt
cgttgcgccggataaggaggtcctgtatgaggcttttgatgagatggaggaatgcgcctctagggcggctctc
atcgaagaggggcagcggatagccgagatgttgaagtccaagatccaaggcttgctgcagcaggcctctaa
gcaggcccaggacatacaacccgctatgcaggcttcatggcccaaagtggaacaattttgggccagacacat
gtggaacttcattagcggcatccaatacctcgcaggattgtcaacactgcagggaaccccgcggtggcttcc
atgatggcattcagtgccgccctcaccagtccgttgtcgaccagtaccaccatccttctcaacatcatgggagg
ctggttagcgtcccagatcgcaccacccgcgggggccaccggctttgtcgtcagtggcctggtggggctgcc
gtgggcagcataggcctgggtaaggtgctggtggacatcctggcaggatatggtgcgggcatttcggggggcc
ctcgtcgcattcaagatcatgtctggcgagaagccctctatggaagatgtcatcaatctactgcctgggatcct
gtctccgggagccctggtggtgggggtcatctgcgcggccattctgcgccgccacgtgggaccgggggaggg
cgcggtccaatggatgaacaggcttattgcctttgcttccagaggaaaccacgtcgcccctactcactacgtga
cggagtcggatgcgtcgcagcgtgtgacccaactacttggctctcttactataaccagcctactcagaagactc
cacaattggataactgaggactgccccatcccatgctccggatcctggctccgcgacgtgtgggactggtttg
caccatcttgacagacttcaaaaattggctgacctctaaattgttccccaagctgcccggcctccccttcatctct
tgtcaaaaggggtacaagggtgtgtgggccggcactggcatcatgaccacgcgctgcccttgcggcgccaac
atctctggcaatgtccgcctgggctctatgaggatcacagggcctaaaacctgcatgaacacctggcagggg
acctttcctatcaattgctacacggagggccagtgcgcgccgaaaccccccacgaactacaagaccgccatct
ggagggtggcggcctcggagtacgcggaggtgacgcagcatgggtcgtactcctatgtaacaggactgacc
actgacaatctgaaaattccttgccaactaccttctccagagttttctcctgggtggacggtgtgcagatccat
aggtttgcacccacaccaaagccgttttccgggatgaggtctcgttctgcgttgggcttaattcctatgctgtc
gggtcccagcttcctgtgaacctgagcccgacgcagacgtattgaggtccatgctaacagatccgccccaca
tcacggcggagactgcggcgcggcgcttggcacggggatcacctccatctgaggcgagctcctcagtgagcc
agctatcagcaccgtcgctgcgggccacctgcaccacccacagcaacacctatgacgtggacatggtcgatgc
caacctgctcatggagggcggtgtggctcagacagagcctgagtccagggtgcccgttctggactttctcgag
ccaatggccgaggaagagagcgaccttgagccctcaataccatcggagtgcatgctccccaggagcgggttt
ccacgggccttaccggcttgggcacggcctgactacaacccgccgctcgtggaatcgtggaggaggccagat
taccaaccgcccaccgttgctggttgtgctctcccccccccaagaaggccccgacgcctcccccaaggagacg
ccggacagtgggtctgagcgagagcaccatatcagaagccctccagcaactggccatcaagacctttggcca
gccccctcgagcggtgatgcaggctcgtccacggggcggggcgccgcgaatccggcggtccgacgtcccct
ggtgagccggccccctcagagacaggttccgcctcctctatgccccccctcgagggggagcctggagatccgg
acctggagtctgatcaggtagagcttcaacctccccccaggggggggggtagctcccggttcggctcggg
gtcttggtctacttgctccgaggaggacgataccaccgtgtgctgctccatgtcatactcctggaccggggctct
aataactccctgtagccccgaagaggaaaagttgccaatcaacccctttgagtaactcgctgttgcgataccat

Fig.11D aacaaggtgtactgtacaacatcaaagagcgcctcacagagggctaaaaaggtaacttttgacaggacgc
aagtgctcgacgcccattatgactcagtcttaaaggacatcaagctagcggcttccaaggtcagcgcaaggc
tcctcaccttggaggaggcgtgccagttgactccaccccattctgcaagatccaagtatggattcggggccaa
ggaggtccgcagcttgtccgggagggccgttaaccacatcaagtccgtgtggaaggacctcctggaagaccc
acaaacaccaattcccacaaccatcatggccaaaaatgaggtgttctgcgtggaccccgccaagggggta
agaaaccagctcgcctcatcgtttaccctgacctcggcgtccgggtctgcgagaaaatggccctctatgacatt
acacaaaagcttcctcaggcggtaatgggagcttcctatggcttccagtactcccctgcccaacgggtggagt
atctcttgaaagcatgggcggaaaagaaggacccccatgggttttttcgtatgatacccgatgcttcgactcaac
cgtcactgagagagacatcaggaccgaggagtccatataccaggcctgctccctgcccgaggaggcccgcac
tgccatacactcgctgactgagagactttacgtaggagggcccatgttcaacagcaagggtcaaacctgcgg
ttacagacgttgccgcgccagcggggtgctaaccactagcatgggtaacaccatcacatgctatgtgaaagc
cctagcggcctgcaaggctgcggggatagttgcgcccacaatgctggtatgcggcgatgacctagtagtcatc
tcagaaagccaggggactgaggaggacgagcggaacctgagagccttcacggaggccatgaccaggtact
ctgcccctcctggtgatcccccagaccggaatatgacctggagctaataacatcctgttcctcaaatgtgtct
gtggcgttgggcccgcggggccgccgcagatactacctgaccagagacccaaccactccactcgcccgggctg
cctgggaaacagttagacactcccctatcaattcatggctgggaaacatcatccagtatgctccaaccatatg
ggttcgcatggtcctaatgacacacttcttctccattctcatggtccaagacaccctggaccagaacctcaactt
tgagatgtatggatcagtatactccgtgaatcctttggaccttccagccataattgagaggttacacgggctt
gacgccttttctatgcacacatactctcaccacgaactgacgcgggtggcttcagccctcagaaaacttgggg
cgccaccccctcagggtgtggaagagtcgggctcgcgcagtcagggcgtccctcatctcccgtggagggaaag
cggccgtttgcggccgatatctcttcaattgggcggtgaagaccaagctcaaactcactccattgccggaggc
gcgcctactggacttatccagttggttcaccgtcggcgccggcgggggcgacattttcacagcgtgtcgcgcg
cccgaccccgctcattactcttcggcctactcctacttttcgtaggggtaggcctcttcctactcccgctcggtag
agcggcacacactaggtacactccatagctaactgttccttttttttttttttttttttttttttttttttttttttttttt
tctttttttttttttttccctctttcttcccttctcatcttattctactttctttcttggtggctccatcttagccctagtca
cggctagctgtgaaaggtccgtgagccgcatgactgcagagagtgccgtaactggtctctctgcagatcatgt

Fig.12A

DNA sequence of the insert J1(C-p7)JFH1 acctgcccctaataggggcgacactccgccatgaatcactcccctgtgaggaactactgtcttcacgcagaaa
gcgcctagccatggcgttagtatgagtgtcgtacagcctccaggccccccctcccgggagagccatagtggt
ctgcggaaccggtgagtacaccggaattgccaggacgaccgggtcctttcttggatcaacccgctcaatgcct
ggagatttgggcgtgccccgcgagactgctagccgagtagtgttgggtcgcgaaaggccttgtggtactgcc
tgatagggtgcttgcgagtgccccgggaggtctcgtagaccgtgcatcatgagcacaaatcctaaaccccaa
agaaaaaccaaacgtaacaccaaccgtcgcccacaggacgttaagttcccgggcggtggtcagatcgtcgg
tggagtttacttgttgccgcgcaggggccccaggttgggtgtgcgtgcgactaggaagacttccgagcggtcg
caacctcgtggaaggcgacaacctatccccaaggctcgccggcccgagggcaggacctgggctcagcctggg
tatccttggcccctctatggcaatgagggcttggggtggcaggatggctcctgtcaccccgcggctctcggcc
tagttggggcccctaatgaccccggcgtaggtcgcgtaatttgggtaaggtcatcgataccccttacatgcggct
tcgccgacctcatggggtacatcccgcttgtcggcgccccttaggggggcgctgccagggccctggcacatggt
gtccgggttctggaggacggcgtgaactatgcaacaggaatttgcccggttgctctttctctatcttcctctta
gctctgctgtcctgtttgaccatcccagcttccgcttatgaagtgcgcaacgtgtccgggatataccatgtcaca
aacgactgctccaactcaagcattgtgtatgaggcggcggacgtgatcatgcatgcccccgggtgcgtgccct
gcgttcgggagaacaattcctcccgttgctgggtagcgctcactcccacgctcgcggccaggaatgccagcgt
ccccactacgacattacgacgccacgtcgacttgctcgttgggacggctgctttctgctccgctatgtacgtggg
ggatctctgcggatctgttttcctcatctcccagctgttcaccttctcgcctcgccggcatgagacagtacagga
ctgcaactgctcaatctatcccggccacgtatcaggccatcgtatggcttgggatatgatgatgaactggtcgc
ccacggcagccttagtggtgtcgcagttactccggatcccacaagctgtcatggacatggtggcgggggccca
ctggggagtcctagcgggccttgcctactattccatggtggggaactgggctaaggttttgattgtgatgctac
tctttgccggcgttgacgggcatacccgcgtgacgggggggtgcaaggccatgtcacctctacactcacgtc
cctctttagacctggggcgtcccagaaaattcagcttgtaaacaccaatggcagttggcatatcaacaggact
gccctgaactgcaatgactccctcaaaactgggtttcttgccgcgctgttctacacacacaagttcaacgcgtc
cggatgcccggagcgcatggccagctgtcgctccattgacaagttcgaccagggatggggtcccatcacctat
gctcaacctgacaactcggaccagaggccgtattgctggcactacgcacctcgacagtgtggtatcgtacccg
cgtcgcaggtgtgcggtccagtgtattgcttcaccccaagccctgttgtagtggggacgaccgatcgtttcggc
gcccctacgtataactggggggacaatgagacggacgtgctgctcctaaacaacacgcggccgccgcatggc
aactggttcggctgtacatggatgaatagcactgggttcaccaagacgtgcggaggccccccgtgtaacatc
agggggtcggcaacaacaccttgacctgccccacggactgcttccggaagcaccccgacgccacttacaca
aaatgtggttcgggcccttggttgacacctaggtgcttggttgactacccatacaggctctggcactacccctg
cactgtcaactttaccatcttcaaggttaggatgtatgtgggggcgtggagcacaggcttgatgctgcatgc
aactggactcgaggagagcgttgcgacttggaggacagggatagagcagagctcagcccgctattgctgtct
acaacagagtggcagatactgccctgttcctacaccaccctaccggctctgtccactggtttaatccacctccac
cagaacatcgtggacatacaatacctgtacggtatagggtcggcggtcgtctccattgccatcaagtgggag

Fig.12B tatgtcgtgctgctcttccttctcctggcggacgcgcgcgtctgtgcctgcttgtggatgatgctgctgatagccc
aggccgaggctgccttagagaacttggtggtcctcaatgcggcgtccgtggtcggagcgcatggcatgctccc
cttctttatgttcttctgtgccgcctggtacatgaagggcaggctggtccctggagcggcatacgctttctacgg
tgtatggccgctgctcctgctcctgctagcattaccaccacgagcttacgcctatgacgcacctgtgcacggac
agataggcgtgggtttgttgatattgatcaccctcttcacactcaccccggggtataagaccctcctcggccag
tgtctgtggtggttgtgctatctcctgaccctgggggaagccatgattcaggagtgggtaccacccatgcaggt
gcgcggcggccgcgatggcatcgcgtgggccgtcactatattctgcccgggtgtggtgtttgacattaccaaat
ggcttttggcgttgcttgggcctgcttacctcttaagggccgctttgacacatgtgccgtacttcgtcagagctc
acgctctgataagggtatgcgcttggtgaagcagctcgcggggggtaggtatgttcaggtggcgctattggc
ccttggcaggtggactggcacctacatctatgaccacctcacacctatgtcggactgggccgctagcggcctgc
gcgacttagcggtcgccgtggaacccatcatcttcagtccgatggagaagaaggtcatcgtctggggagcgg
agacggctgcatgtggggacattctacatggacttcccgtgtccgcccgactcggccaggagatcctcctcggc
ccagctgatggctacacctccaaggggtggaagctccttgctcccatcactgcttatgcccagcaaacacgag
gcctcctgggcgccatagtggtgagtatgacggggcgtgacaggacagaacaggccggggaagtccaaatc
ctgtccacagtctctcagtccttcctcggaacaaccatctcgggggttttgtggactgtttaccacggagctggc
aacaagactctagccggcttacggggtccggtcacgcagatgtactcgagtgctgagggggacttggtaggc
tggcccagcccccctgggaccaagtctttggagccgtgcaagtgtggagccgtcgacctatatctggtcacgc
ggaacgctgatgtcatcccggctcggagacgcggggacaagcggggagcattgctctccccgagacccattt
cgaccttgaaggggtcctcgggggggccggtgctctgccctaggggccacgtcgttgggctcttccgagcagc
tgtgtgctctcggggcgtggccaaatccatcgatttcatccccgttgagacactcgacgttgttacaaggtctcc
cactttcagtgacaacagcacgccaccggctgtgccccagacctatcaggtcgggtacttgcatgctccaactg
gcagtggaaagagcaccaaggtccctgtcgcgtatgccgcccaggggtacaaagtactagtgcttaacccct
cggtagctgccaccctggggtttgggcgtacctatccaaggcacatggcatcaatcccaacattaggactgg
agtcaggaccgtgatgaccggggaggccatcacgtactccacatatggcaaatttctcgccgatgggggctg
cgctagcggcgcctatgacatcatcatatgcgatgaatgccacgctgtggatgctacctccattctcggcatcg
gaacggtccttgatcaagcagagacagccggggtcagactaactgtgctggctacggccacacccccgggt
cagtgacaaccccccatcccgatatagaagaggtaggcctcgggcgggagggtgagatcccttctatggga
gggcgattcccctatcctgcatcaagggagggagacacctgattttctgccactcaaagaaaaagtgtgacg
agctcgcggcggccttcggggcatgggcttgaatgccgtggcatactatagagggttggacgtctccataat
accagctcagggagatgtggtggtcgtcgccaccgacgccctcatgacggggtacactggagactttgactcc
gtgatcgactgcaatgtagcggtcacccaagctgtcgacttcagcctggaccccaccttcactataaccacac
agactgtcccacaagacgctgtctcacgcagtcagcgccgcggcgcacaggtagaggaagacagggcact
tataggtatgtttccactggtgaacgagcctcaggaatgtttgacagtgtagtgctttgtgagtgctacgacg
caggggctgcgtggtacgatctcacaccagcggagaccaccgtcaggcttagagcgtatttcaacacgcccg
gcctacccgtgtgtcaagaccatcttgaattttgggaggcagttttcaccggcctcacacacatagacgcccac
ttcctctcccaaacaaagcaagcgggggagaacttcgcgtacctagtagcctaccaagctacggtgtgcgcc

Fig.12C agagccaaggcccctcccccgtcctgggacgccatgtggaagtgcctggcccgactcaagcctacgcttgcgg
gccccacacctctcctgtaccgtttgggccctattaccaatgaggtcaccctcacacaccctgggacgaagtac
atcgccacatgcatgcaagctgaccttgaggtcatgaccagcacgtgggtcctagctggaggagtcctggca
gccgtcgccgcatattgcctggcgactggatgcgtttccatcatcggccgcttgcacgtcaaccagcgagtcgt
cgttgcgccggataaggaggtcctgtatgaggcttttgatgagatggaggaatgcgcctctagggcggctctc
atcgaagagggcagcggatagccgagatgttgaagtccaagatccaaggcttgctgcagcaggcctctaa
gcaggcccaggacatacaacccgctatgcaggcttcatggcccaaagtggaacaattttgggccagacacat
gtggaacttcattagcggcatccaatacctcgcaggattgtcaacactgccagggaaccccgcggtggcttcc
atgatggcattcagtgccgccctcaccagtccgttgtcgaccagtaccaccatccttctcaacatcatgggagg
ctggttagcgtcccagatcgcaccacccgcgggggccaccggctttgtcgtcagtggcctggtgggggctgcc
gtgggcagcataggcctgggtaaggtgctggtggacatcctggcaggatatggtgcgggcatttcgggggcc
ctcgtcgcattcaagatcatgtctggcgagaagccctctatggaagatgtcatcaatctactgcctgggatcct
gtctccgggagccctggtggtgggggtcatctgcgcggccattctgcgccgccacgtgggaccgggggaggg
cgcggtccaatggatgaacaggcttattgccttgcttccagaggaaaccacgtcgcccctactcactacgtga
cggagtcggatgcgtcgcagcgtgtgacccaactacttggctctcttactataaccagcctactcagaagactc
cacaattggataactgaggactgccccatcccatgctccggatcctggctccgcgacgtgtgggactgggtttg
caccatcttgacagacttcaaaaattggctgacctctaaattgttccccaagctgcccggcctcccccttcatctct
tgtcaaaaggggtacaagggtgtgtgggccggcactggcatcatgaccacgcgctgcccttgcggcgccaac
atctctggcaatgtccgcctgggctctatgaggatcacagggcctaaaacctgcatgaacacctggcagggg
acctttcctatcaattgctacacggagggccagtgcgcgccgaaaaccccccacgaactacaagaccgccatct
ggagggtggcggcctcggagtacgcggaggtgacgcagcatgggtcgtactcctatgtaacaggactgacc
actgacaatctgaaaattccttgccaactaccttctccagagttttctcctgggtggacggtgtgcagatccat
aggtttgcacccacaccaaagccgttttccgggatgaggtctcgttctgcgttgggcttaattcctatgctgtc
gggtcccagcttccctgtgaacctgagcccgacgcagacgtattgaggtccatgctaacagatccgccccaca
tcacggcggagactgcggcgcggcgcttggcacggggatcacctccatctgaggcgagctcctcagtgagcc
agctatcagcaccgtcgctgcgggccacctgcaccacccacagcaacacctatgacgtggacatggtcgatgc
caacctgctcatggagggcggtgtggctcagacagagcctgagtccagggtgcccgttctggactttctcgag
ccaatggccgaggaagagagcgaccttgagccctcaataccatcggagtgcatgctccccaggagcgggttt
ccacgggccttaccggcttgggcacggcctgactacaacccgccgctcgtggaatcgtggaggaggccagat
taccaaccgccaccgttgctggttgtgctctccccccccccaagaaggccccgacgcctcccccaaggagacg
ccggacagtgggtctgagcgagagcaccatatcagaagccctccagcaactggccatcaagacctttggcca
gcccccctcgagcggtgatgcaggctcgtccacgggggcgggcgccgccgaatccggcggtccgacgtcccct
ggtgagccggcccctcagagacaggttccgcctcctctatgcccccctcgagggggagcctggagatccgg
acctggagtctgatcaggtagagcttcaacctccccccaggggggggggggtagctcccggttcgggctcggg
gtcttggtctacttgctccgaggaggacgataccaccgtgtgctgctccatgtcatactcctggaccggggctct
aataactccctgtagccccgaagaggaaaagttgccaatcaacccctttgagtaactcgctgttgcgataccat

Fig.12D aacaaggtgtactgtacaacatcaaagagcgcctcacagagggctaaaaaggtaacttttgacaggacgc
aagtgctcgacgcccattatgactcagtcttaaaggacatcaagctagcggcttccaaggtcagcgcaaggc
tcctcaccttggaggaggcgtgccagttgactccaccccattctgcaagatccaagtatggattcggggccaa
ggaggtccgcagcttgtccgggagggccgttaaccacatcaagtccgtgtggaaggacctcctggaagaccc
acaaacaccaattcccacaaccatcatggccaaaaatgaggtgttctgcgtggaccccgccaagggggggta
agaaaccagctcgcctcatcgtttaccctgacctcggcgtccgggtctgcgagaaaatggccctctatgacatt
acacaaaagcttcctcaggcggtaatgggagcttcctatggcttccagtactcccctgcccaacgggtggagt
atctcttgaaagcatgggcggaaaagaaggaccccatgggttttttcgtatgatacccgatgcttcgactcaac
cgtcactgagagagacatcaggaccgaggagtccatataccaggcctgctccctgcccgaggaggcccgcac
tgccatacactcgctgactgagagactttacgtaggagggcccatgttcaacagcaagggtcaaacctgcgg
ttacagacgttgccgcgccagcggggtgctaaccactagcatgggtaacaccatcacatgctatgtgaaagc
cctagcggcctgcaaggctgcggggatagttgcgcccacaatgctggtatgcggcgatgacctagtagtcatc
tcagaaagccaggggactgaggaggacgagcggaacctgagagccttcacggaggccatgaccaggtact
ctgcccctcctggtgatcccccagaccggaatatgacctggagctaataacatcctgttcctcaaatgtgtct
gtggcgttgggcccgcggggccgccgcagatactacctgaccagagacccaaccactccactcgcccgggctg
cctgggaaacagttagacactcccctatcaattcatggctgggaaacatcatccagtatgctccaaccatatg
ggttcgcatggtcctaatgacacacttcttctccattctcatggtccaagacaccctggaccagaacctcaactt
tgagatgtatggatcagtatactccgtgaatcctttggaccttccagccataattgagaggttacacgggctt
gacgccttttctatgcacacatactctcaccacgaactgacgcggtggcttcagccctcagaaaacttggggg
cgccacccctcagggtgtggaagagtcgggctcgcgcagtcagggcgtccctcatctcccgtggagggaaag
cggccgtttgcggccgatatctcttcaattgggcggtgaagaccaagctcaaactcactccattgccggaggc
gcgcctactggacttatccagttggttcaccgtcggcgccggcggggcgacattttcacagcgtgtcgcgcg
cccgaccccgctcattactcttcggcctactcctactttcgtaggggtaggcctcttcctactccccgctcggtag
agcggcacacactaggtacactccatagctaactgttccttttttttttttttttttttttttttttttttttttttttttt
tcttttttttttttttccctctttcttcccttctcatcttattctactttctttcttggtggctccatcttagccctagtca
cggctagctgtgaaaggtccgtgagccgcatgactgcagagagtgccgtaactggtctctctgcagatcatgt

Fig.13A

DNA sequence of the insert J1(C-NS2)JFH1 acctgcccctaatagggcgacactccgccatgaatcactcccctgtgaggaactactgtcttcacgcagaaa
gcgcctagccatggcgttagtatgagtgtcgtacagcctccaggccccccctcccgggagagccatagtggt
ctgcggaaccggtgagtacaccggaattgccaggacgaccgggtcctttcttggatcaacccgctcaatgcct
ggagatttgggcgtgccccgcgagactgctagccgagtagtgttgggtcgcgaaaggccttgtggtactgcc
tgatagggtgcttgcgagtgccccgggaggtctcgtagaccgtgcatcatgagcacaaatcctaaacccaa
agaaaaaccaaacgtaacaccaaccgtcgcccacaggacgttaagttcccggccggtggtcagatcgtcgg
tggagtttacttgttgccgcgcaggggccccaggttgggtgtgcgtgcgactaggaagacttccgagcggtcg
caacctcgtggaaggcgacaacctatccccaaggctcgccggccccgagggcaggacctgggctcagcctggg
tatccttggcccctctatggcaatgagggcttggggtgggcaggatggctcctgtcaccccgcggctctcggcc
tagttggggccctaatgaccccggcgtaggtcgcgtaatttgggtaaggtcatcgataccttacatgcggct
tcgccgacctcatggggtacatcccgcttgtcggcgccccttaggggcgctgccagggccctggcacatggt
gtccgggttctggaggacggcgtgaactatgcaacagggaatttgcccggttgctctttctctatcttcctctta
gctctgctgtcctgtttgaccatcccagcttccgcttatgaagtgcgcaacgtgtccgggatataccatgtcaca
aacgactgctccaactcaagcattgtgtatgaggcggcggacgtgatcatgcatgccccgggtgcgtgccct
gcgttcgggagaacaattcctcccgttgctgggtagcgctcactcccacgctcgcggccaggaatgccagcgt
cccccactacgacattacgacgccacgtcgacttgctcgttgggacggctgctttctgctccgctatgtacgtggg
ggatctctgcggatctgttttcctcatctcccagctgttcaccttctcgcctcgccggcatgagacagtacagga
ctgcaactgctcaatctatcccggccacgtatcaggccatcgtatggcttgggatatgatgatgaactggtcgc
ccacggcagccttagtggtgtcgcagttactccggatcccacaagctgtcatggacatggtggcggggggccca
ctggggagtcctagcgggccttgcctactattccatggtggggaactgggctaaggttttgattgtgatgctac
tcttttgccggcgttgacgggcatacccgcgtgacgggggggggtgcaaggccatgtcacctctacactcacgtc
cctctttagacctgggcgtcccagaaaattcagcttgtaaacaccaatggcagttggcatatcaacaggact
gccctgaactgcaatgactccctcaaaactgggtttcttgccgcgctgttctacacacacaagttcaacgcgtc
cggatgcccggagcgcatggccagctgtcgctccattgacaagttcgaccagggatggggtcccatcacctat
gctcaacctgacaactcggaccagaggccgtattgctggcactacgcacctcgacagtgtggtatcgtacccg
cgtcgcaggtgtgcggtccagtgtattgcttcaccccaagccctgttgtagtggggacgaccgatcgtttcggc
gccccctacgtataactgggggggacaatgagacggacgtgctgctcctaaacaacacgcggccgccgcatggc
aactggttcggctgtacatggatgaatagcactgggttcaccaagacgtgcggaggcccccccgtgtaacatc
agggggtcggcaacaacaccttgacctgccccacggactgcttccggaagcaccccgacgccacttacaca
aaatgtggttcgggcccttggttgacacctaggtgcttggttgactacccatacaggctctggcactacccctg
cactgtcaactttaccatcttcaaggttaggatgtatgtgggggcgtggagcacaggcttgatgctgcatgc
aactggactcgaggagagcgttgcgacttggaggacagggatagagcagagctcagcccgctattgctgtct
acaacagagtggcagatactgccctgttcctacaccacccaccggctctgtccactggtttaatccacctccac
cagaacatcgtggacatacaatacctgtacggtataggtcggcggtcgtctccattgccatcaagtgggag

Fig.13B tatgtcgtgctgctcttccttctcctggcggacgcgcgcgtctgtgcctgcttgtggatgatgctgctgatagccc
aggccgaggctgccttagagaacttggtggtcctcaatgcggcgtccgtggtcggagcgcatggcatgctccc
cttctttatgttcttctgtgccgcctggtacatgaagggcaggctggtccctggagcggcatacgctttctacgg
tgtatggccgctgctcctgctcctgctagcattaccaccacgagcttacgccatggaccgggagatggttgcat
cttgcggaggcggggttttgtaggtctagcactcctgaccttgtcaccatactgtaaagtgttcctcgctaggc
tcatatggtggttacaatattttatcaccaaagccgaggcgcatttgcaagtgtcgctccccccctcaacgttc
gaggcggacgcgatgccatcatcctcctcatgtgcgcggtccacccagagctaatctttgacatcaccaaactt
ctgctctccatactcggtccgctcatggtgctccaagctagtttaatccgagtgccgtacttcgtgcgcgctcaa
gggctcattcgcgcatgcatgttggtgcggaaagctgccggggggccattatgtccaaatggccttcgtgaagc
tagctgcgctgacaggcacgtacgtttatgaccacctcactccactgcaggattgggcccatgtgggcctacg
agaccttgcggtggcagtagagcccgttgtcttttctgccatggagaccaaggtcatcacctgggggggcagac
accgcggcgtgtggggacattatctcaggtctaccgtctccgcccgaaggggaaggagatacttttggga
ccggccgatagtttgaagggcaggggtggcgactccttgctcccatcactgcttatgcccagcaaacacgag
gcctcctgggcgccatagtggtgagtatgacggggcgtgacaggacagaacaggccggggaagtccaaatc
ctgtccacagtctctcagtccttcctcggaacaaccatctcgggggttttgtggactgtttaccacggagctggc
aacaagactctagccggcttacggggtccggtcacgcagatgtactcgagtgctgaggggacttggtaggc
tggcccagccccctgggaccaagtctttggagccgtgcaagtgtggagccgtcgacctatatctggtcacgc
ggaacgctgatgtcatcccggctcggagacgcggggacaagcggggagcattgctctccccgagacccattt
cgaccttgaaggggtcctcgggggggccggtgctctgccctaggggccacgtcgttgggctcttccgagcagc
tgtgtgctctcggggcgtggccaaatccatcgatttcatccccgttgagacactcgacgttgttacaaggtctcc
cactttcagtgacaacagcacgccaccggctgtgccccagacctatcaggtcgggtacttgcatgctccaactg
gcagtggaaagagcaccaaggtccctgtcgcgtatgccgcccaggggtacaaagtactagtgcttaacccct
cggtagctgccaccctggggtttgggcgtacctatccaaggcacatggcatcaatcccaacattaggactgg
agtcaggaccgtgatgaccggggaggccatcacgtactccacatatggcaaatttctcgccgatggggctg
cgctagcggcgcctatgacatcatcatatgcgatgaatgccacgctgtggatgctacctccattctcggcatcg
gaacggtccttgatcaagcagagacagccggggtcagactaactgtgctggctacggccacaccccccgggt
cagtgacaaccccccatcccgatatagaagaggtaggcctcgggcgggagggtgagatccccttctatggga
gggcgattcccctatcctgcatcaagggagggagacacctgatttctgccactcaaagaaaaagtgtgacg
agctcgcggcggcccttcggggcatgggcttgaatgccgtggcatactatagagggttggacgtctccataat
accagctcagggagatgtggtggtcgtcgccaccgacgccctcatgacggggtacactggagactttgactcc
gtgatcgactgcaatgtagcggtcacccaagctgtcgacttcagcctggaccccaccttcactataaccacac
agactgtcccacaagacgctgtctcacgcagtcagcgccgcgggcgcacaggtagaggaagacagggcact
tataggtatgtttccactggtgaacgagcctcaggaatgtttgacagtgtagtgctttgtgagtgctacgacg
caggggctgcgtggtacgatctcacaccagcggagaccaccgtcaggcttagagcgtatttcaacacgcccg
gcctacccgtgtgtcaagaccatcttgaattttgggaggcagttttcaccggcctcacacacatagacgcccac
ttcctctcccaaacaaagcaagcggggggagaacttcgcgtacctagtagcctaccaagctacggtgtgcgcc

Fig.13C agagccaaggcccctcccccgtcctgggacgccatgtggaagtgcctggcccgactcaagcctacgcttgcgg
gccccacacctctcctgtaccgtttgggccctattaccaatgaggtcaccctcacacaccctgggacgaagtac
atcgccacatgcatgcaagctgaccttgaggtcatgaccagcacgtgggtcctagctggaggagtcctggca
gccgtcgccgcatattgcctggcgactggatgcgtttccatcatcggccgcttgcacgtcaaccagcgagtcgt
cgttgcgccggataaggaggtcctgtatgaggcttttgatgagatggaggaatgcgcctctagggcggctctc
atcgaagaggggcagcggatagccgagatgttgaagtccaagatccaaggcttgctgcagcaggcctctaa
gcaggcccaggacatacaacccgctatgcaggcttcatggcccaaagtggaacaattttgggccagacacat
gtgaacttcattagcggcatccaatacctcgcaggattgtcaacactgccagggaaccccgcggtggcttcc
atgatggcattcagtgccgccctcaccagtccgttgtcgaccagtaccaccatccttctcaacatcatgggagg
ctggttagcgtcccagatcgcaccacccgcgggggccaccggctttgtcgtcagtggcctggtgggggctgcc
gtgggcagcataggcctgggtaaggtgctggtggacatcctggcaggatatggtgcgggcatttcgggggcc
ctcgtcgcattcaagatcatgtctggcgagaagccctctatggaagatgtcatcaatctactgcctgggatcct
gtctccgggagccctggtggtgggggtcatctgcgcggccattctgcgccgccacgtgggaccggggggaggg
cgcggtccaatggatgaacaggcttattgcctttgcttccagaggaaaccacgtcgcccctactcactacgtga
cggagtcggatgcgtcgcagcgtgtgacccaactacttggctctcttactataaccagcctactcagaagactc
cacaattggataactgaggactgccccatcccatgctccggatcctggctccgcgacgtgtgggactgggtttg
caccatcttgacagacttcaaaaattggctgacctctaaattgttccccaagctgccggcctccccttcatctct
tgtcaaaaggggtacaagggtgtgtgggccggcactggcatcatgaccacgcgctgcccttgcggcgccaac
atctctggcaatgtccgcctgggctctatgaggatcacagggcctaaaacctgcatgaacacctggcagggg
acctttcctatcaattgctacacggagggccagtgcgcgccgaaaccccccacgaactacaagaccgccatct
ggagggtggcggcctcggagtacgcggaggtgacgcagcatgggtcgtactcctatgtaacaggactgacc
actgacaatctgaaaattccttgccaactaccttctccagagttttttctcctgggtggacggtgtgcagatccat
aggtttgcacccacaccaaagccgttttccgggatgaggtctcgttctgcgttgggcttaattcctatgctgtc
gggtcccagcttcctgtgaacctgagcccgacgcagacgtattgaggtccatgctaacagatccgccccaca
tcacggcggagactgcggcgcggcgcttggcacggggatcacctccatctgaggcgagctcctcagtgagcc
agctatcagcaccgtcgctgcgggccacctgcaccacccacagcaacacctatgacgtggacatggtcgatgc
caacctgctcatggagggcggtgtggctcagacagagcctgagtccagggtgcccgttctggactttctcgag
ccaatggccgaggaagagagcgaccttgagccctcaataccatcggagtgcatgctcccaggagcgggttt
ccacgggccttaccggcttgggcacggcctgactacaacccgcgctcgtggaatcgtggaggaggccagat
taccaaccgcccaccgttgctggttgtgctctccccccccccaagaaggccccgacgcctcccccaaggagacg
ccggacagtgggtctgagcgagagcaccatatcagaagccctccagcaactggccatcaagacctttggcca
gccccctcgagcggtgatgcaggctcgtccacggggcgggcgccgcgaatccggcggtccgacgtccct
ggtgagccggccccctcagagacaggttccgcctcctctatgccccccctcgagggggagcctggagatccgg
acctggagtctgatcaggtagagcttcaacctccccccaggggggggggtagctcccggttcgggctcggg
gtcttggtctacttgctccgaggaggacgataccaccgtgtgctgctccatgtcatactcctggaccggggctct
aataactccctgtagccccgaagaggaaaagttgccaatcaacccttgagtaactcgctgttgcgataccat

Fig.13D aacaaggtgtactgtacaacatcaaagagcgcctcacagagggctaaaaaggtaacttttgacaggacgc
aagtgctcgacgcccattatgactcagtcttaaaggacatcaagctagcggcttccaaggtcagcgcaaggc
tcctcaccttggaggaggcgtgccagttgactccaccccattctgcaagatccaagtatggattcggggccaa
ggaggtccgcagcttgtccgggagggccgttaaccacatcaagtccgtgtggaaggacctcctggaagaccc
acaaacaccaattcccacaaccatcatggccaaaaatgaggtgttctgcgtggacccgccaaggggggta
agaaaccagctcgcctcatcgtttaccctgacctcggcgtccgggtctgcgagaaaatggccctctatgacatt
acacaaaagcttcctcaggcggtaatgggagcttcctatggcttccagtactcccctgcccaacgggtggagt
atctcttgaaagcatgggcggaaaagaaggaccccatgggttttcgtatgatacccgatgcttcgactcaac
cgtcactgagagagacatcaggaccgaggagtccatataccaggcctgctccctgcccgaggaggcccgcac
tgccatacactcgctgactgagagactttacgtaggagggcccatgttcaacagcaagggtcaaacctgcgg
ttacagacgttgccgcgccagcggggtgctaaccactagcatgggtaacaccatcacatgctatgtgaaagc
cctagcggcctgcaaggctgcggggatagttgcgcccacaatgctggtatgcggcgatgacctagtagtcatc
tcagaaagccaggggactgaggaggacgagcggaacctgagagccttcacggaggccatgaccaggtact
ctgcccctcctggtgatcccccagaccggaatatgacctggagctaataacatcctgttcctcaaatgtgtct
gtggcgttgggcccgcggggccgccgcagatactacctgaccagagacccaaccactccactcgcccgggctg
cctgggaaacagttagacactcccctatcaattcatggctgggaaacatcatccagtatgctccaaccatatg
ggttcgcatggtcctaatgacacacttcttctccattctcatggtccaagacaccctggaccagaacctcaactt
tgagatgtatggatcagtatactccgtgaatcctttggaccttccagccataattgagaggttacacgggctt
gacgccttttctatgcacacatactctcaccacgaactgacgcgggtggcttcagccctcagaaaacttgggg
cgccacccctcagggtgtggaagagtcgggctcgcgcagtcagggcgtccctcatctcccgtggagggaaag
cggccgtttgcggccgatatctcttcaattgggcggtgaagaccaagctcaaactcactccattgccggaggc
gcgcctactggacttatccagttggttcaccgtcggcgccggcggggcgacattttcacagcgtgtcgcgcg
cccgaccccgctcattactcttcggcctactcctacttttcgtaggggtaggcctcttcctactccccgctcggtag
agcggcacacactaggtacactccatagctaactgttcctttttttttttttttttttttttttttttttttttttttt
tctttttttttttttttccctctttcttcccttctcatcttattctactttctttcttggtggctccatcttagccctagtca
cggctagctgtgaaaggtccgtgagccgcatgactgcagagagtgccgtaactggtctctctgcagatcatgt

SEQUENCE LISTING

```
<160> NUMBER OF SEQ ID NOS: 45

<210> SEQ ID NO 1
<211> LENGTH: 45
<212> TYPE: RNA
<213> ORGANISM: Artificial Sequence
<220> FEATURE:
<223> OTHER INFORMATION: Synthetic oligonucleotide

<400> SEQUENCE: 1
gcugauggcg augaaugaac acugcguuug cuggcuuuga ugaaa            45

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 2
gtaccccatg aggtcggcaa ag                                     22

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
gctgatggcg atgaatgaac actg                                   24

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 4
```
gaccgctccg aagttttcct tg                                      22

<210> SEQ ID NO 5
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 5
gaacactgcg tttgctggct ttgatg                                  26

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 6
cgccctatca ggcagtacca caag                                    24

<210> SEQ ID NO 7
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 7
cgggagagcc atagtgg                                            17

<210> SEQ ID NO 8
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 8
agtaccacaa ggcctttcg                                          19

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
ctgcggaacc ggtgagtaca c                                       21

<210> SEQ ID NO 10
<211> LENGTH: 25
<212> TYPE: DNA
<213> ORGANISM: Artificial Sequence
<220> FEATURE:
<223> OTHER INFORMATION: Synthetic primer

<400> SEQUENCE: 10
gccatggcgt tagtatgagt gtcgt                                   25

<210> SEQ ID NO 11
<211> LENGTH: 30
<212> TYPE: DNA
<213> ORGANISM: Artificial Sequence
<220> FEATURE:
<223> OTHER INFORMATION: Synthetic primer

<400> SEQUENCE: 11
tcgtgctcat ggtgcacggt ctacgagacc                                    30

<210> SEQ ID NO 12
<211> LENGTH: 30
<212> TYPE: DNA
<213> ORGANISM: Artificial Sequence
<220> FEATURE:
<223> OTHER INFORMATION: Synthetic primer

<400> SEQUENCE: 12
ggcatacgca tatgacgcac ctgtgcacgg                                    30

<210> SEQ ID NO 13
<211> LENGTH: 27
<212> TYPE: DNA
<213> ORGANISM: Artificial Sequence
<220> FEATURE:
<223> OTHER INFORMATION: Synthetic primer

<400> SEQUENCE: 13
gctctgacga agtacggcac atgtgtc                                       27

<210> SEQ ID NO 14
<211> LENGTH: 30
<212> TYPE: DNA
<213> ORGANISM: Artificial Sequence
<220> FEATURE:
<223> OTHER INFORMATION: Synthetic primer

<400> SEQUENCE: 14
accgtgcacc atgagcacga atcctaaacc                                    30

<210> SEQ ID NO 15
<211> LENGTH: 25
<212> TYPE: DNA
<213> ORGANISM: Artificial Sequence
<220> FEATURE:
<223> OTHER INFORMATION: Synthetic primer

<400> SEQUENCE: 15
gaagccgcac gtaagggtat cgatg                                         25

<210> SEQ ID NO 16
<211> LENGTH: 25
<212> TYPE: DNA
<213> ORGANISM: Artificial Sequence
<220> FEATURE:
<223> OTHER INFORMATION: Synthetic primer

<400> SEQUENCE: 16
cattgtgccc gcaaagagcg tgtgt                                         25

<210> SEQ ID NO 17
<211> LENGTH: 30
<212> TYPE: DNA
<213> ORGANISM: Artificial Sequence
<220> FEATURE:
<223> OTHER INFORMATION: Synthetic primer

<400> SEQUENCE: 17
gtgcgtcata tgcgtatgcc cgctgaggca                                    30

```
<210> SEQ ID NO 18
<211> LENGTH: 30
<212> TYPE: DNA
<213> ORGANISM: Artificial Sequence
<220> FEATURE:
<223> OTHER INFORMATION: Synthetic primer

<400> SEQUENCE: 18
ttgtgctcat ggtgcacggt ctacgagacc                                          30

<210> SEQ ID NO 19
<211> LENGTH: 30
<212> TYPE: DNA
<213> ORGANISM: Artificial Sequence
<220> FEATURE:
<223> OTHER INFORMATION: Synthetic primer

<400> SEQUENCE: 19
agcttacgcc tatgacgcac ctgtgcacgg                                          30

<210> SEQ ID NO 20
<211> LENGTH: 30
<212> TYPE: DNA
<213> ORGANISM: Artificial Sequence
<220> FEATURE:
<223> OTHER INFORMATION: Synthetic primer

<400> SEQUENCE: 20
accgtgcacc atgagcacaa atcctaaacc                                          30

<210> SEQ ID NO 21
<211> LENGTH: 21
<212> TYPE: DNA
<213> ORGANISM: Artificial Sequence
<220> FEATURE:
<223> OTHER INFORMATION: Synthetic primer

<400> SEQUENCE: 21
aagcgggatg taccccatga g                                                   21

<210> SEQ ID NO 22
<211> LENGTH: 30
<212> TYPE: DNA
<213> ORGANISM: Artificial Sequence
<220> FEATURE:
<223> OTHER INFORMATION: Synthetic primer

<400> SEQUENCE: 22
cggctgtaca tggatgaata gcactgggtt                                          30

<210> SEQ ID NO 23
<211> LENGTH: 30
<212> TYPE: DNA
<213> ORGANISM: Artificial Sequence
<220> FEATURE:
<223> OTHER INFORMATION: Synthetic primer

<400> SEQUENCE: 23
gtgcgtcata ggcgtaagct cgtggtggta                                          30

<210> SEQ ID NO 24
<211> LENGTH: 30
<212> TYPE: DNA
<213> ORGANISM: Artificial Sequence
<220> FEATURE:
<223> OTHER INFORMATION: Synthetic primer

<400> SEQUENCE: 24
```

```
gcgactcctt gctcccatca ctgcttatgc                                      30

<210> SEQ ID NO 25
<211> LENGTH: 28
<212> TYPE: DNA
<213> ORGANISM: Artificial Sequence
<220> FEATURE:
<223> OTHER INFORMATION: Synthetic primer

<400> SEQUENCE: 25
tgggagacct tgtaacaacg tcgagtgt                                        28

<210> SEQ ID NO 26
<211> LENGTH: 30
<212> TYPE: DNA
<213> ORGANISM: Artificial Sequence
<220> FEATURE:
<223> OTHER INFORMATION: Synthetic primer

<400> SEQUENCE: 26
cataagcagt gatgggagca aggagtcgcc                                      30

<210> SEQ ID NO 27
<211> LENGTH: 9678
<212> TYPE: DNA
<213> ORGANISM: Hepatitis C virus
<220> FEATURE:
<221> NAME/KEY: CDS
<222> LOCATION: (341)..(9442)

<400> SEQUENCE: 27
acctgcccct aatagggggcg acactccgcc atgaatcact cccctgtgag gaactactgt    60
cttcacgcag aaagcgccta gccatggcgt tagtatgagt gtcgtacagc ctccaggccc   120 cccctcccg ggagagccat agtggtctgc ggaaccggtg agtacaccgg aattgccggg    180
aagactgggt cctttcttgg ataaacccac tctatgcccg gccatttggg cgtgcccccg   240
caagactgct agccgagtag cgttgggttg cgaaaggcct tgtggtactg cctgataggg   300
cgcttgcgag tgccccggga ggtctcgtag accgtgcacc atg agc aca aat cct    355
                                              Met Ser Thr Asn Pro
                                              1               5 aaa cct caa aga aaa acc aaa aga aac acc aac cgt cgc cca gaa gac    403
Lys Pro Gln Arg Lys Thr Lys Arg Asn Thr Asn Arg Arg Pro Glu Asp
            10                  15                  20 gtt aag ttc ccg ggc ggc ggc cag atc gtt ggc gga gta tac ttg ttg    451
Val Lys Phe Pro Gly Gly Gly Gln Ile Val Gly Gly Val Tyr Leu Leu
        25                  30                  35 ccg cgc agg ggc ccc agg ttg ggt gtg cgc acg aca agg aaa act tcg    499
Pro Arg Arg Gly Pro Arg Leu Gly Val Arg Thr Thr Arg Lys Thr Ser
    40                  45                  50 gag cgg tcc cag cca cgt ggg aga cgc cag ccc atc ccc aaa gat cgg    547
Glu Arg Ser Gln Pro Arg Gly Arg Arg Gln Pro Ile Pro Lys Asp Arg
55                  60                  65 cgc tcc act ggc aag gcc tgg gga aaa cca ggt cgc ccc tgg ccc cta    595
Arg Ser Thr Gly Lys Ala Trp Gly Lys Pro Gly Arg Pro Trp Pro Leu
70                  75                  80                  85 tat ggg aat gag gga ctc ggc tgg gca gga tgg ctc ctg tcc ccc cga    643
Tyr Gly Asn Glu Gly Leu Gly Trp Ala Gly Trp Leu Leu Ser Pro Arg
                90                  95                 100 ggc tct cgc ccc tcc tgg ggc ccc act gac ccc cgg cat agg tcg cgc    691
Gly Ser Arg Pro Ser Trp Gly Pro Thr Asp Pro Arg His Arg Ser Arg
            105                 110                 115
```

-continued

| | | |
|---|---|---|
| aac gtg ggt aaa gtc atc gac acc cta acg tgt ggc ttt gcc gac ctc<br>Asn Val Gly Lys Val Ile Asp Thr Leu Thr Cys Gly Phe Ala Asp Leu<br>120 125 130 | 739 | |
| atg ggg tac atc ccc gtc gta ggc gcc ccg ctt agt ggc gcc gcc aga<br>Met Gly Tyr Ile Pro Val Val Gly Ala Pro Leu Ser Gly Ala Ala Arg<br>135 140 145 | 787 | |
| gct gtc gcg cac ggc gtg aga gtc ctg gag gac ggg gtt aat tat gca<br>Ala Val Ala His Gly Val Arg Val Leu Glu Asp Gly Val Asn Tyr Ala<br>150 155 160 165 | 835 | |
| aca ggg aac cta ccc ggt ttc ccc ttt tct atc ttc ttg ctg gcc ctg<br>Thr Gly Asn Leu Pro Gly Phe Pro Phe Ser Ile Phe Leu Leu Ala Leu<br>170 175 180 | 883 | |
| ttg tcc tgc atc acc gtt ccg gtc tct gct gcc cag gtg aag aat acc<br>Leu Ser Cys Ile Thr Val Pro Val Ser Ala Ala Gln Val Lys Asn Thr<br>185 190 195 | 931 | |
| agt agc agc tac atg gtg acc aat gac tgc tcc aat gac agc atc act<br>Ser Ser Ser Tyr Met Val Thr Asn Asp Cys Ser Asn Asp Ser Ile Thr<br>200 205 210 | 979 | |
| tgg cag ctc gag gct gcg gtt ctc cac gtc ccc ggg tgc gtc ccg tgc<br>Trp Gln Leu Glu Ala Ala Val Leu His Val Pro Gly Cys Val Pro Cys<br>215 220 225 | 1027 | |
| gag aga gtg ggg aat acg tca cgg tgt tgg gtg cca gtc tcg cca aac<br>Glu Arg Val Gly Asn Thr Ser Arg Cys Trp Val Pro Val Ser Pro Asn<br>230 235 240 245 | 1075 | |
| atg gct gtg cgg cag ccc ggt gcc ctc acg cag ggt ctg cgg acg cac<br>Met Ala Val Arg Gln Pro Gly Ala Leu Thr Gln Gly Leu Arg Thr His<br>250 255 260 | 1123 | |
| atc gat atg gtt gtg atg tcc gcc acc ttc tgc tct gct ctc tac gtg<br>Ile Asp Met Val Val Met Ser Ala Thr Phe Cys Ser Ala Leu Tyr Val<br>265 270 275 | 1171 | |
| ggg gac ctc tgt ggc ggg gtg atg ctc gcg gcc cag gtg ttc atc gtc<br>Gly Asp Leu Cys Gly Gly Val Met Leu Ala Ala Gln Val Phe Ile Val<br>280 285 290 | 1219 | |
| tcg ccg cag tac cac tgg ttt gtg caa gaa tgc aat tgc tcc atc tac<br>Ser Pro Gln Tyr His Trp Phe Val Gln Glu Cys Asn Cys Ser Ile Tyr<br>295 300 305 | 1267 | |
| cct ggc acc atc act gga cac cgc atg gca tgg gac atg atg atg aac<br>Pro Gly Thr Ile Thr Gly His Arg Met Ala Trp Asp Met Met Met Asn<br>310 315 320 325 | 1315 | |
| tgg tcg ccc acg gcc acc atg atc ctg gcg tac gtg atg cgc gtc ccc<br>Trp Ser Pro Thr Ala Thr Met Ile Leu Ala Tyr Val Met Arg Val Pro<br>330 335 340 | 1363 | |
| gag gtc atc ata gac atc gtt agc ggg gct cac tgg ggc gtc atg ttc<br>Glu Val Ile Ile Asp Ile Val Ser Gly Ala His Trp Gly Val Met Phe<br>345 350 355 | 1411 | |
| ggc ttg gcc tac ttc tct atg cag gga gcg tgg gcg aag gtc att gtc<br>Gly Leu Ala Tyr Phe Ser Met Gln Gly Ala Trp Ala Lys Val Ile Val<br>360 365 370 | 1459 | |
| atc ctt ctg ctg gcc gct ggg gtg gac gcg ggc acc acc acc gtt gga<br>Ile Leu Leu Leu Ala Ala Gly Val Asp Ala Gly Thr Thr Thr Val Gly<br>375 380 385 | 1507 | |
| ggc gct gtt gca cgt tcc acc aac gtg att gcc ggc gtg ttc agc cat<br>Gly Ala Val Ala Arg Ser Thr Asn Val Ile Ala Gly Val Phe Ser His<br>390 395 400 405 | 1555 | |
| ggc cct cag cag aac att cag ctc att aac acc aac ggc agt tgg cac<br>Gly Pro Gln Gln Asn Ile Gln Leu Ile Asn Thr Asn Gly Ser Trp His<br>410 415 420 | 1603 | |
| atc aac cgt act gcc ttg aat tgc aat gac tcc ttg aac acc ggc ttt<br>Ile Asn Arg Thr Ala Leu Asn Cys Asn Asp Ser Leu Asn Thr Gly Phe<br>425 430 435 | 1651 | |

```
ctc gcg gcc ttg ttc tac acc aac cgc ttt aac tcg tca ggg tgt cca    1699
Leu Ala Ala Leu Phe Tyr Thr Asn Arg Phe Asn Ser Ser Gly Cys Pro
        440                 445                 450 ggg cgc ctg tcc gcc tgc cgc aac atc gag gct ttc cgg ata ggg tgg    1747
Gly Arg Leu Ser Ala Cys Arg Asn Ile Glu Ala Phe Arg Ile Gly Trp
    455                 460                 465 ggc acc cta cag tac gag gat aat gtc acc aat cca gag gat atg agg    1795
Gly Thr Leu Gln Tyr Glu Asp Asn Val Thr Asn Pro Glu Asp Met Arg
470             475                 480                 485 ccg tac tgc tgg cac tac ccc cca aag ccg tgt ggc gta gtc ccc gcg    1843
Pro Tyr Cys Trp His Tyr Pro Pro Lys Pro Cys Gly Val Val Pro Ala
                490                 495                 500 agg tct gtg tgt ggc cca gtg tac tgt ttc acc ccc agc ccg gta gta    1891
Arg Ser Val Cys Gly Pro Val Tyr Cys Phe Thr Pro Ser Pro Val Val
            505                 510                 515 gtg ggc acg acc gac aga cgt gga gtg ccc acc tac aca tgg gga gag    1939
Val Gly Thr Thr Asp Arg Arg Gly Val Pro Thr Tyr Thr Trp Gly Glu
        520                 525                 530 aat gag aca gat gtc ttc cta ctg aac agc acc cga ccg ccg cag ggc    1987
Asn Glu Thr Asp Val Phe Leu Leu Asn Ser Thr Arg Pro Pro Gln Gly
    535                 540                 545 tca tgg ttc ggc tgc acg tgg atg aac tcc act ggt ttc acc aag act    2035
Ser Trp Phe Gly Cys Thr Trp Met Asn Ser Thr Gly Phe Thr Lys Thr
550             555                 560                 565 tgt ggc gcg cca cct tgc cgc acc aga gct gac ttc aac gcc agc acg    2083
Cys Gly Ala Pro Pro Cys Arg Thr Arg Ala Asp Phe Asn Ala Ser Thr
                570                 575                 580 gac ttg ttg tgc cct acg gat tgt ttt agg aag cat cct gat gcc act    2131
Asp Leu Leu Cys Pro Thr Asp Cys Phe Arg Lys His Pro Asp Ala Thr
            585                 590                 595 tat att aag tgt ggt tct ggg ccc tgg ctc aca cca aag tgc ctg gtc    2179
Tyr Ile Lys Cys Gly Ser Gly Pro Trp Leu Thr Pro Lys Cys Leu Val
        600                 605                 610 cac tac cct tac aga ctc tgg cat tac ccc tgc aca gtc aat ttt acc    2227
His Tyr Pro Tyr Arg Leu Trp His Tyr Pro Cys Thr Val Asn Phe Thr
    615                 620                 625 atc ttc aag ata aga atg tat gta ggg ggg gtt gag cac agg ctc acg    2275
Ile Phe Lys Ile Arg Met Tyr Val Gly Gly Val Glu His Arg Leu Thr
630             635                 640                 645 gcc gca tgc aac ttc act cgt ggg gat cgc tgc gac ttg gag gac agg    2323
Ala Ala Cys Asn Phe Thr Arg Gly Asp Arg Cys Asp Leu Glu Asp Arg
                650                 655                 660 gac agg agt cag ctg tct cct ctg ttg cac tct acc acg gaa tgg gcc    2371
Asp Arg Ser Gln Leu Ser Pro Leu Leu His Ser Thr Thr Glu Trp Ala
            665                 670                 675 atc ctg ccc tgc acc tac tca gac tta ccc gct ttg tca act ggt ctt    2419
Ile Leu Pro Cys Thr Tyr Ser Asp Leu Pro Ala Leu Ser Thr Gly Leu
        680                 685                 690 ctc cac ctt cac cag aac atc gtg gac gta caa tac atg tat ggc ctc    2467
Leu His Leu His Gln Asn Ile Val Asp Val Gln Tyr Met Tyr Gly Leu
    695                 700                 705 tca cct gct atc aca aaa tac gtc gtt cga tgg gag tgg gtg gta ctc    2515
Ser Pro Ala Ile Thr Lys Tyr Val Val Arg Trp Glu Trp Val Val Leu
710             715                 720                 725 tta ttc ctg ctc tta gcg gac gcc aga gtc tgc gcc tgc ttg tgg atg    2563
Leu Phe Leu Leu Leu Ala Asp Ala Arg Val Cys Ala Cys Leu Trp Met
                730                 735                 740 ctc atc ttg ttg ggc cag gcc gaa gca gca ttg gag aag ttg gtc gtc    2611
Leu Ile Leu Leu Gly Gln Ala Glu Ala Ala Leu Glu Lys Leu Val Val
            745                 750                 755
```

-continued

| | | |
|---|---|---|
| ttg cac gct gcg agt gcg gct aac tgc cat ggc ctc cta tat ttt gcc<br>Leu His Ala Ala Ser Ala Ala Asn Cys His Gly Leu Leu Tyr Phe Ala<br>760           765            770 | | 2659 |
| atc ttc ttc gtg gca gct tgg cac atc agg ggt cgg gtg gtc ccc ttg<br>Ile Phe Phe Val Ala Ala Trp His Ile Arg Gly Arg Val Val Pro Leu<br>775           780            785 | | 2707 |
| acc acc tat tgc ctc act ggc cta tgg ccc ttc tgc cta ctg ctc atg<br>Thr Thr Tyr Cys Leu Thr Gly Leu Trp Pro Phe Cys Leu Leu Leu Met<br>790           795            800           805 | | 2755 |
| gca ctg ccc cgg cag gct tat gcc tat gac gca cct gtg cac gga cag<br>Ala Leu Pro Arg Gln Ala Tyr Ala Tyr Asp Ala Pro Val His Gly Gln<br>810           815            820 | | 2803 |
| ata ggc gtg ggt ttg ttg ata ttg atc acc ctc ttc aca ctc acc ccg<br>Ile Gly Val Gly Leu Leu Ile Leu Ile Thr Leu Phe Thr Leu Thr Pro<br>825           830            835 | | 2851 |
| ggg tat aag acc ctc ctc ggc cag tgt ctg tgg tgg ttg tgc tat ctc<br>Gly Tyr Lys Thr Leu Leu Gly Gln Cys Leu Trp Trp Leu Cys Tyr Leu<br>840           845            850 | | 2899 |
| ctg acc ctg ggg gaa gcc atg att cag gag tgg gta cca ccc atg cag<br>Leu Thr Leu Gly Glu Ala Met Ile Gln Glu Trp Val Pro Pro Met Gln<br>855           860            865 | | 2947 |
| gtg cgc ggc ggc cgc gat ggc atc gcg tgg gcc gtc act ata ttc tgc<br>Val Arg Gly Gly Arg Asp Gly Ile Ala Trp Ala Val Thr Ile Phe Cys<br>870           875            880           885 | | 2995 |
| ccg ggt gtg gtg ttt gac att acc aaa tgg ctt ttg gcg ttg ctt ggg<br>Pro Gly Val Val Phe Asp Ile Thr Lys Trp Leu Leu Ala Leu Leu Gly<br>890           895            900 | | 3043 |
| cct gct tac ctc tta agg gcc gct ttg aca cat gtg ccg tac ttc gtc<br>Pro Ala Tyr Leu Leu Arg Ala Ala Leu Thr His Val Pro Tyr Phe Val<br>905           910            915 | | 3091 |
| aga gct cac gct ctg ata agg gta tgc gct ttg gtg aag cag ctc gcg<br>Arg Ala His Ala Leu Ile Arg Val Cys Ala Leu Val Lys Gln Leu Ala<br>920           925            930 | | 3139 |
| ggg ggt agg tat gtt cag gtg gcg cta ttg gcc ctt ggc agg tgg act<br>Gly Gly Arg Tyr Val Gln Val Ala Leu Leu Ala Leu Gly Arg Trp Thr<br>935           940            945 | | 3187 |
| ggc acc tac atc tat gac cac ctc aca cct atg tcg gac tgg gcc gct<br>Gly Thr Tyr Ile Tyr Asp His Leu Thr Pro Met Ser Asp Trp Ala Ala<br>950           955            960           965 | | 3235 |
| agc ggc ctg cgc gac tta gcg gtc gcc gtg gaa ccc atc atc ttc agt<br>Ser Gly Leu Arg Asp Leu Ala Val Ala Val Glu Pro Ile Ile Phe Ser<br>970           975            980 | | 3283 |
| ccg atg gag aag aag gtc atc gtc tgg gga gcg gag acg gct gca tgt<br>Pro Met Glu Lys Lys Val Ile Val Trp Gly Ala Glu Thr Ala Ala Cys<br>985           990            995 | | 3331 |
| ggg gac att cta cat gga ctt ccc gtg tcc gcc cga ctc ggc cag<br>Gly Asp Ile Leu His Gly Leu Pro Val Ser Ala Arg Leu Gly Gln<br>1000           1005           1010 | | 3376 |
| gag atc ctc ctc ggc cca gct gat ggc tac acc tcc aag ggg tgg<br>Glu Ile Leu Leu Gly Pro Ala Asp Gly Tyr Thr Ser Lys Gly Trp<br>1015           1020           1025 | | 3421 |
| aag ctc ctt gct ccc atc act gct tat gcc cag caa aca cga ggc<br>Lys Leu Leu Ala Pro Ile Thr Ala Tyr Ala Gln Gln Thr Arg Gly<br>1030           1035           1040 | | 3466 |
| ctc ctg ggc gcc ata gtg gtg agt atg acg ggg cgt gac agg aca<br>Leu Leu Gly Ala Ile Val Val Ser Met Thr Gly Arg Asp Arg Thr<br>1045           1050           1055 | | 3511 |
| gaa cag gcc ggg gaa gtc caa atc ctg tcc aca gtc tct cag tcc<br>Glu Gln Ala Gly Glu Val Gln Ile Leu Ser Thr Val Ser Gln Ser<br>1060           1065           1070 | | 3556 |

| | | | | | | | | | | | | | |
|---|---|---|---|---|---|---|---|---|---|---|---|---|---|
| ttc | ctc | gga | aca | acc | atc | tcg | ggg | gtt | ttg | tgg | act | gtt | tac cac | 3601 |
| Phe | Leu | Gly | Thr | Thr | Ile | Ser | Gly | Val | Leu | Trp | Thr | Val | Tyr His | |
| | | 1075 | | | | 1080 | | | | 1085 | | | | |
| gga | gct | ggc | aac | aag | act | cta | gcc | ggc | tta | cgg | ggt | ccg | gtc acg | 3646 |
| Gly | Ala | Gly | Asn | Lys | Thr | Leu | Ala | Gly | Leu | Arg | Gly | Pro | Val Thr | |
| | | 1090 | | | | 1095 | | | | 1100 | | | | |
| cag | atg | tac | tcg | agt | gct | gag | ggg | gac | ttg | gta | ggc | tgg | ccc agc | 3691 |
| Gln | Met | Tyr | Ser | Ser | Ala | Glu | Gly | Asp | Leu | Val | Gly | Trp | Pro Ser | |
| | | 1105 | | | | 1110 | | | | 1115 | | | | |
| ccc | cct | ggg | acc | aag | tct | ttg | gag | ccg | tgc | aag | tgt | gga | gcc gtc | 3736 |
| Pro | Pro | Gly | Thr | Lys | Ser | Leu | Glu | Pro | Cys | Lys | Cys | Gly | Ala Val | |
| | | 1120 | | | | 1125 | | | | 1130 | | | | |
| gac | cta | tat | ctg | gtc | acg | cgg | aac | gct | gat | gtc | atc | ccg | gct cgg | 3781 |
| Asp | Leu | Tyr | Leu | Val | Thr | Arg | Asn | Ala | Asp | Val | Ile | Pro | Ala Arg | |
| | | 1135 | | | | 1140 | | | | 1145 | | | | |
| aga | cgc | ggg | gac | aag | cgg | gga | gca | ttg | ctc | tcc | ccg | aga | ccc att | 3826 |
| Arg | Arg | Gly | Asp | Lys | Arg | Gly | Ala | Leu | Leu | Ser | Pro | Arg | Pro Ile | |
| | | 1150 | | | | 1155 | | | | 1160 | | | | |
| tcg | acc | ttg | aag | ggg | tcc | tcg | ggg | ggg | ccg | gtg | ctc | tgc | cct agg | 3871 |
| Ser | Thr | Leu | Lys | Gly | Ser | Ser | Gly | Gly | Pro | Val | Leu | Cys | Pro Arg | |
| | | 1165 | | | | 1170 | | | | 1175 | | | | |
| ggc | cac | gtc | gtt | ggg | ctc | ttc | cga | gca | gct | gtg | tgc | tct | cgg ggc | 3916 |
| Gly | His | Val | Val | Gly | Leu | Phe | Arg | Ala | Ala | Val | Cys | Ser | Arg Gly | |
| | | 1180 | | | | 1185 | | | | 1190 | | | | |
| gtg | gcc | aaa | tcc | atc | gat | ttc | atc | ccc | gtt | gag | aca | ctc | gac gtt | 3961 |
| Val | Ala | Lys | Ser | Ile | Asp | Phe | Ile | Pro | Val | Glu | Thr | Leu | Asp Val | |
| | | 1195 | | | | 1200 | | | | 1205 | | | | |
| gtt | aca | agg | tct | ccc | act | ttc | agt | gac | aac | agc | acg | cca | ccg gct | 4006 |
| Val | Thr | Arg | Ser | Pro | Thr | Phe | Ser | Asp | Asn | Ser | Thr | Pro | Pro Ala | |
| | | 1210 | | | | 1215 | | | | 1220 | | | | |
| gtg | ccc | cag | acc | tat | cag | gtc | ggg | tac | ttg | cat | gct | cca | act ggc | 4051 |
| Val | Pro | Gln | Thr | Tyr | Gln | Val | Gly | Tyr | Leu | His | Ala | Pro | Thr Gly | |
| | | 1225 | | | | 1230 | | | | 1235 | | | | |
| agt | gga | aag | agc | acc | aag | gtc | cct | gtc | gcg | tat | gcc | gcc | cag ggg | 4096 |
| Ser | Gly | Lys | Ser | Thr | Lys | Val | Pro | Val | Ala | Tyr | Ala | Ala | Gln Gly | |
| | | 1240 | | | | 1245 | | | | 1250 | | | | |
| tac | aaa | gta | cta | gtg | ctt | aac | ccc | tcg | gta | gct | gcc | acc | ctg ggg | 4141 |
| Tyr | Lys | Val | Leu | Val | Leu | Asn | Pro | Ser | Val | Ala | Ala | Thr | Leu Gly | |
| | | 1255 | | | | 1260 | | | | 1265 | | | | |
| ttt | ggg | gcg | tac | cta | tcc | aag | gca | cat | ggc | atc | aat | ccc | aac att | 4186 |
| Phe | Gly | Ala | Tyr | Leu | Ser | Lys | Ala | His | Gly | Ile | Asn | Pro | Asn Ile | |
| | | 1270 | | | | 1275 | | | | 1280 | | | | |
| agg | act | gga | gtc | agg | acc | gtg | atg | acc | ggg | gag | gcc | atc | acg tac | 4231 |
| Arg | Thr | Gly | Val | Arg | Thr | Val | Met | Thr | Gly | Glu | Ala | Ile | Thr Tyr | |
| | | 1285 | | | | 1290 | | | | 1295 | | | | |
| tcc | aca | tat | ggc | aaa | ttt | ctc | gcc | gat | ggg | ggc | tgc | gct | agc ggc | 4276 |
| Ser | Thr | Tyr | Gly | Lys | Phe | Leu | Ala | Asp | Gly | Gly | Cys | Ala | Ser Gly | |
| | | 1300 | | | | 1305 | | | | 1310 | | | | |
| gcc | tat | gac | atc | atc | ata | tgc | gat | gaa | tgc | cac | gct | gtg | gat gct | 4321 |
| Ala | Tyr | Asp | Ile | Ile | Ile | Cys | Asp | Glu | Cys | His | Ala | Val | Asp Ala | |
| | | 1315 | | | | 1320 | | | | 1325 | | | | |
| acc | tcc | att | ctc | ggc | atc | gga | acg | gtc | ctt | gat | caa | gca | gag aca | 4366 |
| Thr | Ser | Ile | Leu | Gly | Ile | Gly | Thr | Val | Leu | Asp | Gln | Ala | Glu Thr | |
| | | 1330 | | | | 1335 | | | | 1340 | | | | |
| gcc | ggg | gtc | aga | cta | act | gtg | ctg | gct | acg | gcc | aca | ccc | ccc ggg | 4411 |
| Ala | Gly | Val | Arg | Leu | Thr | Val | Leu | Ala | Thr | Ala | Thr | Pro | Pro Gly | |
| | | 1345 | | | | 1350 | | | | 1355 | | | | |
| tca | gtg | aca | acc | ccc | cat | ccc | gat | ata | gaa | gag | gta | ggc | ctc ggg | 4456 |
| Ser | Val | Thr | Thr | Pro | His | Pro | Asp | Ile | Glu | Glu | Val | Gly | Leu Gly | |
| | | 1360 | | | | 1365 | | | | 1370 | | | | |

| | | | | | | | | |
|---|---|---|---|---|---|---|---|---|
| cgg Arg | gag Glu | ggt Gly 1375 | gag Glu | atc Ile | ccc Pro | ttc Phe | tat Tyr 1380 | ggg Gly | agg Arg | gcg Ala | att Ile 1385 | ccc Pro | cta Leu | tcc Ser | 4501 |

```
cgg gag ggt gag atc ccc ttc tat ggg agg gcg att ccc cta tcc        4501
Arg Glu Gly Glu Ile Pro Phe Tyr Gly Arg Ala Ile Pro Leu Ser
        1375            1380            1385 tgc atc aag gga ggg aga cac ctg att ttc tgc cac tca aag aaa        4546
Cys Ile Lys Gly Gly Arg His Leu Ile Phe Cys His Ser Lys Lys
        1390            1395            1400 aag tgt gac gag ctc gcg gcg gcc ctt cgg ggc atg ggc ttg aat        4591
Lys Cys Asp Glu Leu Ala Ala Ala Leu Arg Gly Met Gly Leu Asn
        1405            1410            1415 gcc gtg gca tac tat aga ggg ttg gac gtc tcc ata ata cca gct        4636
Ala Val Ala Tyr Tyr Arg Gly Leu Asp Val Ser Ile Ile Pro Ala
        1420            1425            1430 cag gga gat gtg gtg gtc gtc gcc acc gac gcc ctc atg acg ggg        4681
Gln Gly Asp Val Val Val Val Ala Thr Asp Ala Leu Met Thr Gly
        1435            1440            1445 tac act gga gac ttt gac tcc gtg atc gac tgc aat gta gcg gtc        4726
Tyr Thr Gly Asp Phe Asp Ser Val Ile Asp Cys Asn Val Ala Val
        1450            1455            1460 acc caa gct gtc gac ttc agc ctg gac ccc acc ttc act ata acc        4771
Thr Gln Ala Val Asp Phe Ser Leu Asp Pro Thr Phe Thr Ile Thr
        1465            1470            1475 aca cag act gtc cca caa gac gct gtc tca cgc agt cag cgc cgc        4816
Thr Gln Thr Val Pro Gln Asp Ala Val Ser Arg Ser Gln Arg Arg
        1480            1485            1490 ggg cgc aca ggt aga gga aga cag ggc act tat agg tat gtt tcc        4861
Gly Arg Thr Gly Arg Gly Arg Gln Gly Thr Tyr Arg Tyr Val Ser
        1495            1500            1505 act ggt gaa cga gcc tca gga atg ttt gac agt gta gtg ctt tgt        4906
Thr Gly Glu Arg Ala Ser Gly Met Phe Asp Ser Val Val Leu Cys
        1510            1515            1520 gag tgc tac gac gca ggg gct gcg tgg tac gat ctc aca cca gcg        4951
Glu Cys Tyr Asp Ala Gly Ala Ala Trp Tyr Asp Leu Thr Pro Ala
        1525            1530            1535 gag acc acc gtc agg ctt aga gcg tat ttc aac acg ccc ggc cta        4996
Glu Thr Thr Val Arg Leu Arg Ala Tyr Phe Asn Thr Pro Gly Leu
        1540            1545            1550 ccc gtg tgt caa gac cat ctt gaa ttt tgg gag gca gtt ttc acc        5041
Pro Val Cys Gln Asp His Leu Glu Phe Trp Glu Ala Val Phe Thr
        1555            1560            1565 ggc ctc aca cac ata gac gcc cac ttc ctc tcc caa aca aag caa        5086
Gly Leu Thr His Ile Asp Ala His Phe Leu Ser Gln Thr Lys Gln
        1570            1575            1580 gcg ggg gag aac ttc gcg tac cta gta gcc tac caa gct acg gtg        5131
Ala Gly Glu Asn Phe Ala Tyr Leu Val Ala Tyr Gln Ala Thr Val
        1585            1590            1595 tgc gcc aga gcc aag gcc cct ccc ccg tcc tgg gac gcc atg tgg        5176
Cys Ala Arg Ala Lys Ala Pro Pro Pro Ser Trp Asp Ala Met Trp
        1600            1605            1610 aag tgc ctg gcc cga ctc aag cct acg ctt gcg ggc ccc aca cct        5221
Lys Cys Leu Ala Arg Leu Lys Pro Thr Leu Ala Gly Pro Thr Pro
        1615            1620            1625 ctc ctg tac cgt ttg ggc cct att acc aat gag gtc acc ctc aca        5266
Leu Leu Tyr Arg Leu Gly Pro Ile Thr Asn Glu Val Thr Leu Thr
        1630            1635            1640 cac cct ggg acg aag tac atc gcc aca tgc atg caa gct gac ctt        5311
His Pro Gly Thr Lys Tyr Ile Ala Thr Cys Met Gln Ala Asp Leu
        1645            1650            1655 gag gtc atg acc agc acg tgg gtc cta gct gga gga gtc ctg gca        5356
Glu Val Met Thr Ser Thr Trp Val Leu Ala Gly Gly Val Leu Ala
        1660            1665            1670
```

| | | |
|---|---|---|
| gcc gtc gcc gca tat tgc ctg gcg act gga tgc gtt tcc atc atc<br>Ala Val Ala Ala Tyr Cys Leu Ala Thr Gly Cys Val Ser Ile Ile<br>　　　　1675　　　　　　　　1680　　　　　　　　1685 | | 5401 |
| ggc cgc ttg cac gtc aac cag cga gtc gtc gtt gcg ccg gat aag<br>Gly Arg Leu His Val Asn Gln Arg Val Val Val Ala Pro Asp Lys<br>　　　1690　　　　　　　　1695　　　　　　　　1700 | | 5446 |
| gag gtc ctg tat gag gct ttt gat gag atg gag gaa tgc gcc tct<br>Glu Val Leu Tyr Glu Ala Phe Asp Glu Met Glu Glu Cys Ala Ser<br>　　　　1705　　　　　　　　1710　　　　　　　　1715 | | 5491 |
| agg gcg gct ctc atc gaa gag ggg cag cgg ata gcc gag atg ttg<br>Arg Ala Ala Leu Ile Glu Glu Gly Gln Arg Ile Ala Glu Met Leu<br>　　　1720　　　　　　　　1725　　　　　　　　1730 | | 5536 |
| aag tcc aag atc caa ggc ttg ctg cag cag gcc tct aag cag gcc<br>Lys Ser Lys Ile Gln Gly Leu Leu Gln Gln Ala Ser Lys Gln Ala<br>　　　　1735　　　　　　　　1740　　　　　　　　1745 | | 5581 |
| cag gac ata caa ccc gct atg cag gct tca tgg ccc aaa gtg gaa<br>Gln Asp Ile Gln Pro Ala Met Gln Ala Ser Trp Pro Lys Val Glu<br>　　　1750　　　　　　　　1755　　　　　　　　1760 | | 5626 |
| caa ttt tgg gcc aga cac atg tgg aac ttc att agc ggc atc caa<br>Gln Phe Trp Ala Arg His Met Trp Asn Phe Ile Ser Gly Ile Gln<br>　　　　1765　　　　　　　　1770　　　　　　　　1775 | | 5671 |
| tac ctc gca gga ttg tca aca ctg cca ggg aac ccc gcg gtg gct<br>Tyr Leu Ala Gly Leu Ser Thr Leu Pro Gly Asn Pro Ala Val Ala<br>　　　1780　　　　　　　　1785　　　　　　　　1790 | | 5716 |
| tcc atg atg gca ttc agt gcc gcc ctc acc agt ccg ttg tcg acc<br>Ser Met Met Ala Phe Ser Ala Ala Leu Thr Ser Pro Leu Ser Thr<br>　　　　1795　　　　　　　　1800　　　　　　　　1805 | | 5761 |
| agt acc acc atc ctt ctc aac atc atg gga ggc tgg tta gcg tcc<br>Ser Thr Thr Ile Leu Leu Asn Ile Met Gly Gly Trp Leu Ala Ser<br>　　　1810　　　　　　　　1815　　　　　　　　1820 | | 5806 |
| cag atc gca cca ccc gcg ggg gcc acc ggc ttt gtc gtc agt ggc<br>Gln Ile Ala Pro Pro Ala Gly Ala Thr Gly Phe Val Val Ser Gly<br>　　　　1825　　　　　　　　1830　　　　　　　　1835 | | 5851 |
| ctg gtg ggg gct gcc gtg ggc agc ata ggc ctg ggt aag gtg ctg<br>Leu Val Gly Ala Ala Val Gly Ser Ile Gly Leu Gly Lys Val Leu<br>　　　1840　　　　　　　　1845　　　　　　　　1850 | | 5896 |
| gtg gac atc ctg gca gga tat ggt gcg ggc att tcg ggg gcc ctc<br>Val Asp Ile Leu Ala Gly Tyr Gly Ala Gly Ile Ser Gly Ala Leu<br>　　　　1855　　　　　　　　1860　　　　　　　　1865 | | 5941 |
| gtc gca ttc aag atc atg tct ggc gag aag ccc tct atg gaa gat<br>Val Ala Phe Lys Ile Met Ser Gly Glu Lys Pro Ser Met Glu Asp<br>　　　1870　　　　　　　　1875　　　　　　　　1880 | | 5986 |
| gtc atc aat cta ctg cct ggg atc ctg tct ccg gga gcc ctg gtg<br>Val Ile Asn Leu Leu Pro Gly Ile Leu Ser Pro Gly Ala Leu Val<br>　　　　1885　　　　　　　　1890　　　　　　　　1895 | | 6031 |
| gtg ggg gtc atc tgc gcg gcc att ctg cgc cgc cac gtg gga ccg<br>Val Gly Val Ile Cys Ala Ala Ile Leu Arg Arg His Val Gly Pro<br>　　　1900　　　　　　　　1905　　　　　　　　1910 | | 6076 |
| ggg gag ggc gcg gtc caa tgg atg aac agg ctt att gcc ttt gct<br>Gly Glu Gly Ala Val Gln Trp Met Asn Arg Leu Ile Ala Phe Ala<br>　　　　1915　　　　　　　　1920　　　　　　　　1925 | | 6121 |
| tcc aga gga aac cac gtc gcc cct act cac tac gtg acg gag tcg<br>Ser Arg Gly Asn His Val Ala Pro Thr His Tyr Val Thr Glu Ser<br>　　　1930　　　　　　　　1935　　　　　　　　1940 | | 6166 |
| gat gcg tcg cag cgt gtg acc caa cta ctt ggc tct ctt act ata<br>Asp Ala Ser Gln Arg Val Thr Gln Leu Leu Gly Ser Leu Thr Ile<br>　　　　1945　　　　　　　　1950　　　　　　　　1955 | | 6211 |
| acc agc cta ctc aga aga ctc cac aat tgg ata act gag gac tgc<br>Thr Ser Leu Leu Arg Arg Leu His Asn Trp Ile Thr Glu Asp Cys<br>　　　1960　　　　　　　　1965　　　　　　　　1970 | | 6256 |

| | | | | | | | | | | |
|---|---|---|---|---|---|---|---|---|---|---|
| ccc | atc | cca | tgc | tcc | gga | tcc | tgg | ctc | cgc | gac | gtg | tgg | gac | tgg | 6301 |
| Pro | Ile | Pro | Cys | Ser | Gly | Ser | Trp | Leu | Arg | Asp | Val | Trp | Asp | Trp | |
| | | 1975 | | | | 1980 | | | | | 1985 | | | | |
| gtt | tgc | acc | atc | ttg | aca | gac | ttc | aaa | aat | tgg | ctg | acc | tct | aaa | 6346 |
| Val | Cys | Thr | Ile | Leu | Thr | Asp | Phe | Lys | Asn | Trp | Leu | Thr | Ser | Lys | |
| | | 1990 | | | | 1995 | | | | 2000 | | | | | |
| ttg | ttc | ccc | aag | ctg | ccc | ggc | ctc | ccc | ttc | atc | tct | tgt | caa | aag | 6391 |
| Leu | Phe | Pro | Lys | Leu | Pro | Gly | Leu | Pro | Phe | Ile | Ser | Cys | Gln | Lys | |
| | | 2005 | | | | 2010 | | | | 2015 | | | | | |
| ggg | tac | aag | ggt | gtg | tgg | gcc | ggc | act | ggc | atc | atg | acc | acg | cgc | 6436 |
| Gly | Tyr | Lys | Gly | Val | Trp | Ala | Gly | Thr | Gly | Ile | Met | Thr | Thr | Arg | |
| | | 2020 | | | | 2025 | | | | 2030 | | | | | |
| tgc | cct | tgc | ggc | gcc | aac | atc | tct | ggc | aat | gtc | cgc | ctg | ggc | tct | 6481 |
| Cys | Pro | Cys | Gly | Ala | Asn | Ile | Ser | Gly | Asn | Val | Arg | Leu | Gly | Ser | |
| | | 2035 | | | | 2040 | | | | 2045 | | | | | |
| atg | agg | atc | aca | ggg | cct | aaa | acc | tgc | atg | aac | acc | tgg | cag | ggg | 6526 |
| Met | Arg | Ile | Thr | Gly | Pro | Lys | Thr | Cys | Met | Asn | Thr | Trp | Gln | Gly | |
| | | 2050 | | | | 2055 | | | | 2060 | | | | | |
| acc | ttt | cct | atc | aat | tgc | tac | acg | gag | ggc | cag | tgc | gcg | ccg | aaa | 6571 |
| Thr | Phe | Pro | Ile | Asn | Cys | Tyr | Thr | Glu | Gly | Gln | Cys | Ala | Pro | Lys | |
| | | 2065 | | | | 2070 | | | | 2075 | | | | | |
| ccc | ccc | acg | aac | tac | aag | acc | gcc | atc | tgg | agg | gtg | gcg | gcc | tcg | 6616 |
| Pro | Pro | Thr | Asn | Tyr | Lys | Thr | Ala | Ile | Trp | Arg | Val | Ala | Ala | Ser | |
| | | 2080 | | | | 2085 | | | | 2090 | | | | | |
| gag | tac | gcg | gag | gtg | acg | cag | cat | ggg | tcg | tac | tcc | tat | gta | aca | 6661 |
| Glu | Tyr | Ala | Glu | Val | Thr | Gln | His | Gly | Ser | Tyr | Ser | Tyr | Val | Thr | |
| | | 2095 | | | | 2100 | | | | 2105 | | | | | |
| gga | ctg | acc | act | gac | aat | ctg | aaa | att | cct | tgc | caa | cta | cct | tct | 6706 |
| Gly | Leu | Thr | Thr | Asp | Asn | Leu | Lys | Ile | Pro | Cys | Gln | Leu | Pro | Ser | |
| | | 2110 | | | | 2115 | | | | 2120 | | | | | |
| cca | gag | ttt | ttc | tcc | tgg | gtg | gac | ggt | gtg | cag | atc | cat | agg | ttt | 6751 |
| Pro | Glu | Phe | Phe | Ser | Trp | Val | Asp | Gly | Val | Gln | Ile | His | Arg | Phe | |
| | | 2125 | | | | 2130 | | | | 2135 | | | | | |
| gca | ccc | aca | cca | aag | ccg | ttt | ttc | cgg | gat | gag | gtc | tcg | ttc | tgc | 6796 |
| Ala | Pro | Thr | Pro | Lys | Pro | Phe | Phe | Arg | Asp | Glu | Val | Ser | Phe | Cys | |
| | | 2140 | | | | 2145 | | | | 2150 | | | | | |
| gtt | ggg | ctt | aat | tcc | tat | gct | gtc | ggg | tcc | cag | ctt | ccc | tgt | gaa | 6841 |
| Val | Gly | Leu | Asn | Ser | Tyr | Ala | Val | Gly | Ser | Gln | Leu | Pro | Cys | Glu | |
| | | 2155 | | | | 2160 | | | | 2165 | | | | | |
| cct | gag | ccc | gac | gca | gac | gta | ttg | agg | tcc | atg | cta | aca | gat | ccg | 6886 |
| Pro | Glu | Pro | Asp | Ala | Asp | Val | Leu | Arg | Ser | Met | Leu | Thr | Asp | Pro | |
| | | 2170 | | | | 2175 | | | | 2180 | | | | | |
| ccc | cac | atc | acg | gcg | gag | act | gcg | gcg | cgg | cgc | ttg | gca | cgg | gga | 6931 |
| Pro | His | Ile | Thr | Ala | Glu | Thr | Ala | Ala | Arg | Arg | Leu | Ala | Arg | Gly | |
| | | 2185 | | | | 2190 | | | | 2195 | | | | | |
| tca | cct | cca | tct | gag | gcg | agc | tcc | tca | gtg | agc | cag | cta | tca | gca | 6976 |
| Ser | Pro | Pro | Ser | Glu | Ala | Ser | Ser | Ser | Val | Ser | Gln | Leu | Ser | Ala | |
| | | 2200 | | | | 2205 | | | | 2210 | | | | | |
| ccg | tcg | ctg | cgg | gcc | acc | tgc | acc | acc | cac | agc | aac | acc | tat | gac | 7021 |
| Pro | Ser | Leu | Arg | Ala | Thr | Cys | Thr | Thr | His | Ser | Asn | Thr | Tyr | Asp | |
| | | 2215 | | | | 2220 | | | | 2225 | | | | | |
| gtg | gac | atg | gtc | gat | gcc | aac | ctg | ctc | atg | gag | ggc | ggt | gtg | gct | 7066 |
| Val | Asp | Met | Val | Asp | Ala | Asn | Leu | Leu | Met | Glu | Gly | Gly | Val | Ala | |
| | | 2230 | | | | 2235 | | | | 2240 | | | | | |
| cag | aca | gag | cct | gag | tcc | agg | gtg | ccc | gtt | ctg | gac | ttt | ctc | gag | 7111 |
| Gln | Thr | Glu | Pro | Glu | Ser | Arg | Val | Pro | Val | Leu | Asp | Phe | Leu | Glu | |
| | | 2245 | | | | 2250 | | | | 2255 | | | | | |
| cca | atg | gcc | gag | gaa | gag | agc | gac | ctt | gag | ccc | tca | ata | cca | tcg | 7156 |
| Pro | Met | Ala | Glu | Glu | Glu | Ser | Asp | Leu | Glu | Pro | Ser | Ile | Pro | Ser | |
| | | 2260 | | | | 2265 | | | | 2270 | | | | | |

```
gag tgc atg ctc ccc agg agc ggg ttt cca cgg gcc tta ccg gct      7201
Glu Cys Met Leu Pro Arg Ser Gly Phe Pro Arg Ala Leu Pro Ala
        2275                2280                2285 tgg gca cgg cct gac tac aac ccg ccg ctc gtg aa tcg tgg agg       7246
Trp Ala Arg Pro Asp Tyr Asn Pro Pro Leu Val Glu Ser Trp Arg
    2290                2295                2300 agg cca gat tac caa ccg ccc acc gtt gct ggt tgt gct ctc ccc      7291
Arg Pro Asp Tyr Gln Pro Pro Thr Val Ala Gly Cys Ala Leu Pro
        2305                2310                2315 ccc ccc aag aag gcc ccg acg cct ccc cca agg aga cgc cgg aca      7336
Pro Pro Lys Lys Ala Pro Thr Pro Pro Pro Arg Arg Arg Arg Thr
        2320                2325                2330 gtg ggt ctg agc gag agc acc ata tca gaa gcc ctc cag caa ctg      7381
Val Gly Leu Ser Glu Ser Thr Ile Ser Glu Ala Leu Gln Gln Leu
        2335                2340                2345 gcc atc aag acc ttt ggc cag ccc ccc tcg agc ggt gat gca ggc      7426
Ala Ile Lys Thr Phe Gly Gln Pro Pro Ser Ser Gly Asp Ala Gly
        2350                2355                2360 tcg tcc acg ggg gcg ggc gcc gcc gaa tcc ggc ggt ccg acg tcc      7471
Ser Ser Thr Gly Ala Gly Ala Ala Glu Ser Gly Gly Pro Thr Ser
        2365                2370                2375 cct ggt gag ccg gcc ccc tca gag aca ggt tcc gcc tcc tct atg      7516
Pro Gly Glu Pro Ala Pro Ser Glu Thr Gly Ser Ala Ser Ser Met
        2380                2385                2390 ccc ccc ctc gag ggg gag cct gga gat ccg gac ctg gag tct gat      7561
Pro Pro Leu Glu Gly Glu Pro Gly Asp Pro Asp Leu Glu Ser Asp
        2395                2400                2405 cag gta gag ctt caa cct ccc ccc cag ggg ggg ggg gta gct ccc      7606
Gln Val Glu Leu Gln Pro Pro Pro Gln Gly Gly Gly Val Ala Pro
        2410                2415                2420 ggt tcg ggc tcg ggg tct tgg tct act tgc tcc gag gag gac gat      7651
Gly Ser Gly Ser Gly Ser Trp Ser Thr Cys Ser Glu Glu Asp Asp
        2425                2430                2435 acc acc gtg tgc tgc tcc atg tca tac tcc tgg acc ggg gct cta      7696
Thr Thr Val Cys Cys Ser Met Ser Tyr Ser Trp Thr Gly Ala Leu
        2440                2445                2450 ata act ccc tgt agc ccc gaa gag gaa aag ttg cca atc aac cct      7741
Ile Thr Pro Cys Ser Pro Glu Glu Glu Lys Leu Pro Ile Asn Pro
        2455                2460                2465 ttg agt aac tcg ctg ttg cga tac cat aac aag gtg tac tgt aca      7786
Leu Ser Asn Ser Leu Leu Arg Tyr His Asn Lys Val Tyr Cys Thr
        2470                2475                2480 aca tca aag agc gcc tca cag agg gct aaa aag gta act ttt gac      7831
Thr Ser Lys Ser Ala Ser Gln Arg Ala Lys Lys Val Thr Phe Asp
        2485                2490                2495 agg acg caa gtg ctc gac gcc cat tat gac tca gtc tta aag gac      7876
Arg Thr Gln Val Leu Asp Ala His Tyr Asp Ser Val Leu Lys Asp
        2500                2505                2510 atc aag cta gcg gct tcc aag gtc agc gca agg ctc ctc acc ttg      7921
Ile Lys Leu Ala Ala Ser Lys Val Ser Ala Arg Leu Leu Thr Leu
        2515                2520                2525 gag gag gcg tgc cag ttg act cca ccc cat tct gca aga tcc aag      7966
Glu Glu Ala Cys Gln Leu Thr Pro Pro His Ser Ala Arg Ser Lys
        2530                2535                2540 tat gga ttc ggg gcc aag gag gtc cgc agc ttg tcc ggg agg gcc      8011
Tyr Gly Phe Gly Ala Lys Glu Val Arg Ser Leu Ser Gly Arg Ala
        2545                2550                2555 gtt aac cac atc aag tcc gtg tgg aag gac ctc ctg gaa gac cca      8056
Val Asn His Ile Lys Ser Val Trp Lys Asp Leu Leu Glu Asp Pro
        2560                2565                2570
```

```
caa aca cca att ccc aca acc atc atg gcc aaa aat gag gtg ttc        8101
Gln Thr Pro Ile Pro Thr Thr Ile Met Ala Lys Asn Glu Val Phe
        2575                2580                2585 tgc gtg gac ccc gcc aag ggg ggt aag aaa cca gct cgc ctc atc        8146
Cys Val Asp Pro Ala Lys Gly Gly Lys Lys Pro Ala Arg Leu Ile
2590                2595                2600 gtt tac cct gac ctc ggc gtc cgg gtc tgc gag aaa atg gcc ctc        8191
Val Tyr Pro Asp Leu Gly Val Arg Val Cys Glu Lys Met Ala Leu
            2605                2610                2615 tat gac att aca caa aag ctt cct cag gcg gta atg gga gct tcc        8236
Tyr Asp Ile Thr Gln Lys Leu Pro Gln Ala Val Met Gly Ala Ser
                2620                2625                2630 tat ggc ttc cag tac tcc cct gcc caa cgg gtg gag tat ctc ttg        8281
Tyr Gly Phe Gln Tyr Ser Pro Ala Gln Arg Val Glu Tyr Leu Leu
                    2635                2640                2645 aaa gca tgg gcg gaa aag aag gac ccc atg ggt ttt tcg tat gat        8326
Lys Ala Trp Ala Glu Lys Lys Asp Pro Met Gly Phe Ser Tyr Asp
2650                2655                2660 acc cga tgc ttc gac tca acc gtc act gag aga gac atc agg acc        8371
Thr Arg Cys Phe Asp Ser Thr Val Thr Glu Arg Asp Ile Arg Thr
        2665                2670                2675 gag gag tcc ata tac cag gcc tgc tcc ctg ccc gag gag gcc cgc        8416
Glu Glu Ser Ile Tyr Gln Ala Cys Ser Leu Pro Glu Glu Ala Arg
            2680                2685                2690 act gcc ata cac tcg ctg act gag aga ctt tac gta gga ggg ccc        8461
Thr Ala Ile His Ser Leu Thr Glu Arg Leu Tyr Val Gly Gly Pro
                2695                2700                2705 atg ttc aac agc aag ggt caa acc tgc ggt tac aga cgt tgc cgc        8506
Met Phe Asn Ser Lys Gly Gln Thr Cys Gly Tyr Arg Arg Cys Arg
                    2710                2715                2720 gcc agc ggg gtg cta acc act agc atg ggt aac acc atc aca tgc        8551
Ala Ser Gly Val Leu Thr Thr Ser Met Gly Asn Thr Ile Thr Cys
2725                2730                2735 tat gtg aaa gcc cta gcg gcc tgc aag gct gcg ggg ata gtt gcg        8596
Tyr Val Lys Ala Leu Ala Ala Cys Lys Ala Ala Gly Ile Val Ala
        2740                2745                2750 ccc aca atg ctg gta tgc ggc gat gac cta gta gtc atc tca gaa        8641
Pro Thr Met Leu Val Cys Gly Asp Asp Leu Val Val Ile Ser Glu
            2755                2760                2765 agc cag ggg act gag gag gac gag cgg aac ctg aga gcc ttc acg        8686
Ser Gln Gly Thr Glu Glu Asp Glu Arg Asn Leu Arg Ala Phe Thr
                2770                2775                2780 gag gcc atg acc agg tac tct gcc cct cct ggt gat ccc ccc aga        8731
Glu Ala Met Thr Arg Tyr Ser Ala Pro Pro Gly Asp Pro Pro Arg
                    2785                2790                2795 ccg gaa tat gac ctg gag cta ata aca tcc tgt tcc tca aat gtg        8776
Pro Glu Tyr Asp Leu Glu Leu Ile Thr Ser Cys Ser Ser Asn Val
2800                2805                2810 tct gtg gcg ttg ggc ccg cgg ggc cgc cgc aga tac tac ctg acc        8821
Ser Val Ala Leu Gly Pro Arg Gly Arg Arg Arg Tyr Tyr Leu Thr
        2815                2820                2825 aga gac cca acc act cca ctc gcc cgg gct gcc tgg gaa aca gtt        8866
Arg Asp Pro Thr Thr Pro Leu Ala Arg Ala Ala Trp Glu Thr Val
            2830                2835                2840 aga cac tcc cct atc aat tca tgg ctg gga aac atc atc cag tat        8911
Arg His Ser Pro Ile Asn Ser Trp Leu Gly Asn Ile Ile Gln Tyr
                2845                2850                2855 gct cca acc ata tgg gtt cgc atg gtc cta atg aca cac ttc ttc        8956
Ala Pro Thr Ile Trp Val Arg Met Val Leu Met Thr His Phe Phe
                    2860                2865                2870
```

| | | | | | | | | | | | | |
|---|---|---|---|---|---|---|---|---|---|---|---|---|
| tcc | att | ctc | atg | gtc | caa | gac | acc | ctg | gac | cag | aac | ctc | aac | ttt | 9001 |
| Ser | Ile | Leu | Met | Val | Gln | Asp | Thr | Leu | Asp | Gln | Asn | Leu | Asn | Phe | |
| | 2875 | | | | 2880 | | | | | 2885 | | | | | | gag atg tat gga tca gta tac tcc gtg aat cct ttg gac ctt cca 9046
Glu Met Tyr Gly Ser Val Tyr Ser Val Asn Pro Leu Asp Leu Pro
    2890                2895                2900 gcc ata att gag agg tta cac ggg ctt gac gcc ttt tct atg cac 9091
Ala Ile Ile Glu Arg Leu His Gly Leu Asp Ala Phe Ser Met His
    2905                2910                2915 aca tac tct cac cac gaa ctg acg cgg gtg gct tca gcc ctc aga 9136
Thr Tyr Ser His His Glu Leu Thr Arg Val Ala Ser Ala Leu Arg
    2920                2925                2930 aaa ctt ggg gcg cca ccc ctc agg gtg tgg aag agt cgg gct cgc 9181
Lys Leu Gly Ala Pro Pro Leu Arg Val Trp Lys Ser Arg Ala Arg
    2935                2940                2945 gca gtc agg gcg tcc ctc atc tcc cgt gga ggg aaa gcg gcc gtt 9226
Ala Val Arg Ala Ser Leu Ile Ser Arg Gly Gly Lys Ala Ala Val
    2950                2955                2960 tgc ggc cga tat ctc ttc aat tgg gcg gtg aag acc aag ctc aaa 9271
Cys Gly Arg Tyr Leu Phe Asn Trp Ala Val Lys Thr Lys Leu Lys
    2965                2970                2975 ctc act cca ttg ccg gag gcg cgc cta ctg gac tta tcc agt tgg 9316
Leu Thr Pro Leu Pro Glu Ala Arg Leu Leu Asp Leu Ser Ser Trp
    2980                2985                2990 ttc acc gtc ggc gcc ggc ggg ggc gac att ttt cac agc gtg tcg 9361
Phe Thr Val Gly Ala Gly Gly Gly Asp Ile Phe His Ser Val Ser
    2995                3000                3005 cgc gcc cga ccc cgc tca tta ctc ttc ggc cta ctc ctt ttc 9406
Arg Ala Arg Pro Arg Ser Leu Leu Phe Gly Leu Leu Leu Phe
    3010                3015                3020 gta ggg gta ggc ctc ttc cta ctc ccc gct cgg tag agcggcacac 9452
Val Gly Val Gly Leu Phe Leu Leu Pro Ala Arg
    3025                3030 actaggtaca ctccatagct aactgttcct tttttttttt tttttttttt tttttttttt 9512 tttttttttt ttcttttttt ttttttttccc tctttcttcc cttctcatct tattctactt 9572 tctttcttgg tggctccatc ttagccctag tcacggctag ctgtgaaagg tccgtgagcc 9632 gcatgactgc agagagtgcc gtaactggtc tctctgcaga tcatgt 9678

<210> SEQ ID NO 28
<211> LENGTH: 3033
<212> TYPE: PRT
<213> ORGANISM: Hepatitis C virus

<400> SEQUENCE: 28

Met Ser Thr Asn Pro Lys Pro Gln Arg Lys Thr Lys Arg Asn Thr Asn
1               5                   10                  15

Arg Arg Pro Glu Asp Val Lys Phe Pro Gly Gly Gly Gln Ile Val Gly
            20                  25                  30

Gly Val Tyr Leu Leu Pro Arg Arg Gly Pro Arg Leu Gly Val Arg Thr
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ala Trp Gly Lys Pro Gly
65                  70                  75                  80

Arg Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

```
Arg His Arg Ser Arg Asn Val Gly Lys Val Ile Asp Thr Leu Thr Cys
            115                 120                 125
Gly Phe Ala Asp Leu Met Gly Tyr Ile Pro Val Val Gly Ala Pro Leu
        130                 135                 140
Ser Gly Ala Ala Arg Ala Val Ala His Gly Val Arg Val Leu Glu Asp
145                 150                 155                 160
Gly Val Asn Tyr Ala Thr Gly Asn Leu Pro Gly Phe Pro Phe Ser Ile
                165                 170                 175
Phe Leu Leu Ala Leu Leu Ser Cys Ile Thr Val Pro Val Ser Ala Ala
                180                 185                 190
Gln Val Lys Asn Thr Ser Ser Tyr Met Val Thr Asn Asp Cys Ser
            195                 200                 205
Asn Asp Ser Ile Thr Trp Gln Leu Glu Ala Ala Val Leu His Val Pro
    210                 215                 220
Gly Cys Val Pro Cys Glu Arg Val Gly Asn Thr Ser Arg Cys Trp Val
225                 230                 235                 240
Pro Val Ser Pro Asn Met Ala Val Arg Gln Pro Gly Ala Leu Thr Gln
                245                 250                 255
Gly Leu Arg Thr His Ile Asp Met Val Val Met Ser Ala Thr Phe Cys
            260                 265                 270
Ser Ala Leu Tyr Val Gly Asp Leu Cys Gly Gly Val Met Leu Ala Ala
            275                 280                 285
Gln Val Phe Ile Val Ser Pro Gln Tyr His Trp Phe Val Gln Glu Cys
        290                 295                 300
Asn Cys Ser Ile Tyr Pro Gly Thr Ile Thr Gly His Arg Met Ala Trp
305                 310                 315                 320
Asp Met Met Met Asn Trp Ser Pro Thr Ala Thr Met Ile Leu Ala Tyr
                325                 330                 335
Val Met Arg Val Pro Glu Val Ile Ile Asp Ile Val Ser Gly Ala His
            340                 345                 350
Trp Gly Val Met Phe Gly Leu Ala Tyr Phe Ser Met Gln Gly Ala Trp
        355                 360                 365
Ala Lys Val Ile Val Ile Leu Leu Leu Ala Ala Gly Val Asp Ala Gly
        370                 375                 380
Thr Thr Thr Val Gly Gly Ala Val Ala Arg Ser Thr Asn Val Ile Ala
385                 390                 395                 400
Gly Val Phe Ser His Gly Pro Gln Gln Asn Ile Gln Leu Ile Asn Thr
                405                 410                 415
Asn Gly Ser Trp His Ile Asn Arg Thr Ala Leu Asn Cys Asn Asp Ser
                420                 425                 430
Leu Asn Thr Gly Phe Leu Ala Ala Leu Phe Tyr Thr Asn Arg Phe Asn
            435                 440                 445
Ser Ser Gly Cys Pro Gly Arg Leu Ser Ala Cys Arg Asn Ile Glu Ala
        450                 455                 460
Phe Arg Ile Gly Trp Gly Thr Leu Gln Tyr Glu Asp Asn Val Thr Asn
465                 470                 475                 480
Pro Glu Asp Met Arg Pro Tyr Cys Trp His Tyr Pro Lys Pro Cys
                485                 490                 495
Gly Val Val Pro Ala Arg Ser Val Cys Gly Pro Val Tyr Cys Phe Thr
                500                 505                 510
Pro Ser Pro Val Val Val Gly Thr Thr Asp Arg Arg Gly Val Pro Thr
            515                 520                 525
Tyr Thr Trp Gly Glu Asn Glu Thr Asp Val Phe Leu Leu Asn Ser Thr
```

```
                530             535             540
Arg Pro Pro Gln Gly Ser Trp Phe Gly Cys Thr Trp Met Asn Ser Thr
545             550             555             560

Gly Phe Thr Lys Thr Cys Gly Ala Pro Pro Cys Arg Thr Arg Ala Asp
            565             570             575

Phe Asn Ala Ser Thr Asp Leu Leu Cys Pro Thr Asp Cys Phe Arg Lys
            580             585             590

His Pro Asp Ala Thr Tyr Ile Lys Cys Gly Ser Gly Pro Trp Leu Thr
            595             600             605

Pro Lys Cys Leu Val His Tyr Pro Tyr Arg Leu Trp His Tyr Pro Cys
            610             615             620

Thr Val Asn Phe Thr Ile Phe Lys Ile Arg Met Tyr Val Gly Gly Val
625             630             635             640

Glu His Arg Leu Thr Ala Ala Cys Asn Phe Thr Arg Gly Asp Arg Cys
            645             650             655

Asp Leu Glu Asp Arg Asp Arg Ser Gln Leu Ser Pro Leu Leu His Ser
            660             665             670

Thr Thr Glu Trp Ala Ile Leu Pro Cys Thr Tyr Ser Asp Leu Pro Ala
            675             680             685

Leu Ser Thr Gly Leu Leu His Leu His Gln Asn Ile Val Asp Val Gln
690             695             700

Tyr Met Tyr Gly Leu Ser Pro Ala Ile Thr Lys Tyr Val Val Arg Trp
705             710             715             720

Glu Trp Val Val Leu Leu Phe Leu Leu Leu Ala Asp Ala Arg Val Cys
            725             730             735

Ala Cys Leu Trp Met Leu Ile Leu Leu Gly Gln Ala Glu Ala Ala Leu
            740             745             750

Glu Lys Leu Val Val Leu His Ala Ala Ser Ala Ala Asn Cys His Gly
            755             760             765

Leu Leu Tyr Phe Ala Ile Phe Phe Val Ala Ala Trp His Ile Arg Gly
770             775             780

Arg Val Val Pro Leu Thr Thr Tyr Cys Leu Thr Gly Leu Trp Pro Phe
785             790             795             800

Cys Leu Leu Leu Met Ala Leu Pro Arg Gln Ala Tyr Ala Tyr Asp Ala
            805             810             815

Pro Val His Gly Gln Ile Gly Val Gly Leu Leu Ile Leu Ile Thr Leu
            820             825             830

Phe Thr Leu Thr Pro Gly Tyr Lys Thr Leu Leu Gly Gln Cys Leu Trp
            835             840             845

Trp Leu Cys Tyr Leu Leu Thr Leu Gly Glu Ala Met Ile Gln Glu Trp
850             855             860

Val Pro Pro Met Gln Val Arg Gly Gly Arg Asp Gly Ile Ala Trp Ala
865             870             875             880

Val Thr Ile Phe Cys Pro Gly Val Val Phe Asp Ile Thr Lys Trp Leu
            885             890             895

Leu Ala Leu Leu Gly Pro Ala Tyr Leu Leu Arg Ala Ala Leu Thr His
            900             905             910

Val Pro Tyr Phe Val Arg Ala His Ala Leu Ile Arg Val Cys Ala Leu
            915             920             925

Val Lys Gln Leu Ala Gly Gly Arg Tyr Val Gln Val Ala Leu Leu Ala
            930             935             940

Leu Gly Arg Trp Thr Gly Thr Tyr Ile Tyr Asp His Leu Thr Pro Met
945             950             955             960
```

```
Ser Asp Trp Ala Ala Ser Gly Leu Arg Asp Leu Ala Val Ala Val Glu
            965                 970                 975

Pro Ile Ile Phe Ser Pro Met Glu Lys Lys Val Ile Val Trp Gly Ala
        980                 985                 990

Glu Thr Ala Ala Cys Gly Asp Ile Leu His Gly Leu Pro Val Ser Ala
        995                 1000                1005

Arg Leu Gly Gln Glu Ile Leu Leu Gly Pro Ala Asp Gly Tyr Thr
    1010                1015                1020

Ser Lys Gly Trp Lys Leu Leu Ala Pro Ile Thr Ala Tyr Ala Gln
    1025                1030                1035

Gln Thr Arg Gly Leu Leu Gly Ala Ile Val Val Ser Met Thr Gly
    1040                1045                1050

Arg Asp Arg Thr Glu Gln Ala Gly Glu Val Gln Ile Leu Ser Thr
    1055                1060                1065

Val Ser Gln Ser Phe Leu Gly Thr Thr Ile Ser Gly Val Leu Trp
    1070                1075                1080

Thr Val Tyr His Gly Ala Gly Asn Lys Thr Leu Ala Gly Leu Arg
    1085                1090                1095

Gly Pro Val Thr Gln Met Tyr Ser Ser Ala Glu Gly Asp Leu Val
    1100                1105                1110

Gly Trp Pro Ser Pro Pro Gly Thr Lys Ser Leu Glu Pro Cys Lys
    1115                1120                1125

Cys Gly Ala Val Asp Leu Tyr Leu Val Thr Arg Asn Ala Asp Val
    1130                1135                1140

Ile Pro Ala Arg Arg Arg Gly Asp Lys Arg Gly Ala Leu Leu Ser
    1145                1150                1155

Pro Arg Pro Ile Ser Thr Leu Lys Gly Ser Ser Gly Gly Pro Val
    1160                1165                1170

Leu Cys Pro Arg Gly His Val Val Gly Leu Phe Arg Ala Ala Val
    1175                1180                1185

Cys Ser Arg Gly Val Ala Lys Ser Ile Asp Phe Ile Pro Val Glu
    1190                1195                1200

Thr Leu Asp Val Val Thr Arg Ser Pro Thr Phe Ser Asp Asn Ser
    1205                1210                1215

Thr Pro Pro Ala Val Pro Gln Thr Tyr Gln Val Gly Tyr Leu His
    1220                1225                1230

Ala Pro Thr Gly Ser Gly Lys Ser Thr Lys Val Pro Val Ala Tyr
    1235                1240                1245

Ala Ala Gln Gly Tyr Lys Val Leu Val Leu Asn Pro Ser Val Ala
    1250                1255                1260

Ala Thr Leu Gly Phe Gly Ala Tyr Leu Ser Lys Ala His Gly Ile
    1265                1270                1275

Asn Pro Asn Ile Arg Thr Gly Val Arg Thr Val Met Thr Gly Glu
    1280                1285                1290

Ala Ile Thr Tyr Ser Thr Tyr Gly Lys Phe Leu Ala Asp Gly Gly
    1295                1300                1305

Cys Ala Ser Gly Ala Tyr Asp Ile Ile Ile Cys Asp Glu Cys His
    1310                1315                1320

Ala Val Asp Ala Thr Ser Ile Leu Gly Ile Gly Thr Val Leu Asp
    1325                1330                1335

Gln Ala Glu Thr Ala Gly Val Arg Leu Thr Val Leu Ala Thr Ala
    1340                1345                1350

Thr Pro Pro Gly Ser Val Thr Thr Pro His Pro Asp Ile Glu Glu
    1355                1360                1365
```

```
Val Gly Leu Gly Arg Glu Gly Glu Ile Pro Phe Tyr Gly Arg Ala
    1370            1375                1380

Ile Pro Leu Ser Cys Ile Lys Gly Gly Arg His Leu Ile Phe Cys
    1385            1390                1395

His Ser Lys Lys Lys Cys Asp Glu Leu Ala Ala Ala Leu Arg Gly
    1400            1405                1410

Met Gly Leu Asn Ala Val Ala Tyr Tyr Arg Gly Leu Asp Val Ser
    1415            1420                1425

Ile Ile Pro Ala Gln Gly Asp Val Val Val Ala Thr Asp Ala
    1430            1435                1440

Leu Met Thr Gly Tyr Thr Gly Asp Phe Asp Ser Val Ile Asp Cys
    1445            1450                1455

Asn Val Ala Val Thr Gln Ala Val Asp Phe Ser Leu Asp Pro Thr
    1460            1465                1470

Phe Thr Ile Thr Thr Gln Thr Val Pro Gln Asp Ala Val Ser Arg
    1475            1480                1485

Ser Gln Arg Arg Gly Arg Thr Gly Arg Gly Arg Gln Gly Thr Tyr
    1490            1495                1500

Arg Tyr Val Ser Thr Gly Glu Arg Ala Ser Gly Met Phe Asp Ser
    1505            1510                1515

Val Val Leu Cys Glu Cys Tyr Asp Ala Gly Ala Ala Trp Tyr Asp
    1520            1525                1530

Leu Thr Pro Ala Glu Thr Thr Val Arg Leu Arg Ala Tyr Phe Asn
    1535            1540                1545

Thr Pro Gly Leu Pro Val Cys Gln Asp His Leu Glu Phe Trp Glu
    1550            1555                1560

Ala Val Phe Thr Gly Leu Thr His Ile Asp Ala His Phe Leu Ser
    1565            1570                1575

Gln Thr Lys Gln Ala Gly Glu Asn Phe Ala Tyr Leu Val Ala Tyr
    1580            1585                1590

Gln Ala Thr Val Cys Ala Arg Ala Lys Ala Pro Pro Pro Ser Trp
    1595            1600                1605

Asp Ala Met Trp Lys Cys Leu Ala Arg Leu Lys Pro Thr Leu Ala
    1610            1615                1620

Gly Pro Thr Pro Leu Leu Tyr Arg Leu Gly Pro Ile Thr Asn Glu
    1625            1630                1635

Val Thr Leu Thr His Pro Gly Thr Lys Tyr Ile Ala Thr Cys Met
    1640            1645                1650

Gln Ala Asp Leu Glu Val Met Thr Ser Thr Trp Val Leu Ala Gly
    1655            1660                1665

Gly Val Leu Ala Ala Val Ala Ala Tyr Cys Leu Ala Thr Gly Cys
    1670            1675                1680

Val Ser Ile Ile Gly Arg Leu His Val Asn Gln Arg Val Val Val
    1685            1690                1695

Ala Pro Asp Lys Glu Val Leu Tyr Glu Ala Phe Asp Glu Met Glu
    1700            1705                1710

Glu Cys Ala Ser Arg Ala Ala Leu Ile Glu Glu Gly Gln Arg Ile
    1715            1720                1725

Ala Glu Met Leu Lys Ser Lys Ile Gln Gly Leu Leu Gln Gln Ala
    1730            1735                1740

Ser Lys Gln Ala Gln Asp Ile Gln Pro Ala Met Gln Ala Ser Trp
    1745            1750                1755

Pro Lys Val Glu Gln Phe Trp Ala Arg His Met Trp Asn Phe Ile
```

-continued

```
                1760                1765                1770

Ser Gly Ile Gln Tyr Leu Ala Gly Leu Ser Thr Leu Pro Gly Asn
    1775                1780                1785

Pro Ala Val Ala Ser Met Met Ala Phe Ser Ala Ala Leu Thr Ser
    1790                1795                1800

Pro Leu Ser Thr Ser Thr Thr Ile Leu Leu Asn Ile Met Gly Gly
    1805                1810                1815

Trp Leu Ala Ser Gln Ile Ala Pro Pro Ala Gly Ala Thr Gly Phe
    1820                1825                1830

Val Val Ser Gly Leu Val Gly Ala Ala Val Gly Ser Ile Gly Leu
    1835                1840                1845

Gly Lys Val Leu Val Asp Ile Leu Ala Gly Tyr Gly Ala Gly Ile
    1850                1855                1860

Ser Gly Ala Leu Val Ala Phe Lys Ile Met Ser Gly Glu Lys Pro
    1865                1870                1875

Ser Met Glu Asp Val Ile Asn Leu Leu Pro Gly Ile Leu Ser Pro
    1880                1885                1890

Gly Ala Leu Val Val Gly Val Ile Cys Ala Ala Ile Leu Arg Arg
    1895                1900                1905

His Val Gly Pro Gly Glu Gly Ala Val Gln Trp Met Asn Arg Leu
    1910                1915                1920

Ile Ala Phe Ala Ser Arg Gly Asn His Val Ala Pro Thr His Tyr
    1925                1930                1935

Val Thr Glu Ser Asp Ala Ser Gln Arg Val Thr Gln Leu Leu Gly
    1940                1945                1950

Ser Leu Thr Ile Thr Ser Leu Leu Arg Arg Leu His Asn Trp Ile
    1955                1960                1965

Thr Glu Asp Cys Pro Ile Pro Cys Ser Gly Ser Trp Leu Arg Asp
    1970                1975                1980

Val Trp Asp Trp Val Cys Thr Ile Leu Thr Asp Phe Lys Asn Trp
    1985                1990                1995

Leu Thr Ser Lys Leu Phe Pro Lys Leu Pro Gly Leu Pro Phe Ile
    2000                2005                2010

Ser Cys Gln Lys Gly Tyr Lys Gly Val Trp Ala Gly Thr Gly Ile
    2015                2020                2025

Met Thr Thr Arg Cys Pro Cys Gly Ala Asn Ile Ser Gly Asn Val
    2030                2035                2040

Arg Leu Gly Ser Met Arg Ile Thr Gly Pro Lys Thr Cys Met Asn
    2045                2050                2055

Thr Trp Gln Gly Thr Phe Pro Ile Asn Cys Tyr Thr Glu Gly Gln
    2060                2065                2070

Cys Ala Pro Lys Pro Pro Thr Asn Tyr Lys Thr Ala Ile Trp Arg
    2075                2080                2085

Val Ala Ala Ser Glu Tyr Ala Glu Val Thr Gln His Gly Ser Tyr
    2090                2095                2100

Ser Tyr Val Thr Gly Leu Thr Thr Asp Asn Leu Lys Ile Pro Cys
    2105                2110                2115

Gln Leu Pro Ser Pro Glu Phe Phe Ser Trp Val Asp Gly Val Gln
    2120                2125                2130

Ile His Arg Phe Ala Pro Thr Pro Lys Pro Phe Phe Arg Asp Glu
    2135                2140                2145

Val Ser Phe Cys Val Gly Leu Asn Ser Tyr Ala Val Gly Ser Gln
    2150                2155                2160
```

-continued

Leu Pro Cys Glu Pro Glu Pro Asp Ala Asp Val Leu Arg Ser Met
2165                2170                2175

Leu Thr Asp Pro Pro His Ile Thr Ala Glu Thr Ala Ala Arg Arg
2180                2185                2190

Leu Ala Arg Gly Ser Pro Pro Ser Glu Ala Ser Ser Ser Val Ser
2195                2200                2205

Gln Leu Ser Ala Pro Ser Leu Arg Ala Thr Cys Thr Thr His Ser
2210                2215                2220

Asn Thr Tyr Asp Val Asp Met Val Asp Ala Asn Leu Leu Met Glu
2225                2230                2235

Gly Gly Val Ala Gln Thr Glu Pro Glu Ser Arg Val Pro Val Leu
2240                2245                2250

Asp Phe Leu Glu Pro Met Ala Glu Glu Glu Ser Asp Leu Glu Pro
2255                2260                2265

Ser Ile Pro Ser Glu Cys Met Leu Pro Arg Ser Gly Phe Pro Arg
2270                2275                2280

Ala Leu Pro Ala Trp Ala Arg Pro Asp Tyr Asn Pro Pro Leu Val
2285                2290                2295

Glu Ser Trp Arg Arg Pro Asp Tyr Gln Pro Pro Thr Val Ala Gly
2300                2305                2310

Cys Ala Leu Pro Pro Pro Lys Lys Ala Pro Thr Pro Pro Pro Arg
2315                2320                2325

Arg Arg Arg Thr Val Gly Leu Ser Glu Ser Thr Ile Ser Glu Ala
2330                2335                2340

Leu Gln Gln Leu Ala Ile Lys Thr Phe Gly Gln Pro Pro Ser Ser
2345                2350                2355

Gly Asp Ala Gly Ser Ser Thr Gly Ala Gly Ala Ala Glu Ser Gly
2360                2365                2370

Gly Pro Thr Ser Pro Gly Glu Pro Ala Pro Ser Glu Thr Gly Ser
2375                2380                2385

Ala Ser Ser Met Pro Pro Leu Glu Gly Glu Pro Gly Asp Pro Asp
2390                2395                2400

Leu Glu Ser Asp Gln Val Glu Leu Gln Pro Pro Gln Gly Gly
2405                2410                2415

Gly Val Ala Pro Gly Ser Gly Ser Gly Ser Trp Ser Thr Cys Ser
2420                2425                2430

Glu Glu Asp Asp Thr Thr Val Cys Cys Ser Met Ser Tyr Ser Trp
2435                2440                2445

Thr Gly Ala Leu Ile Thr Pro Cys Ser Pro Glu Glu Glu Lys Leu
2450                2455                2460

Pro Ile Asn Pro Leu Ser Asn Ser Leu Leu Arg Tyr His Asn Lys
2465                2470                2475

Val Tyr Cys Thr Thr Ser Lys Ser Ala Ser Gln Arg Ala Lys Lys
2480                2485                2490

Val Thr Phe Asp Arg Thr Gln Val Leu Asp Ala His Tyr Asp Ser
2495                2500                2505

Val Leu Lys Asp Ile Lys Leu Ala Ala Ser Lys Val Ser Ala Arg
2510                2515                2520

Leu Leu Thr Leu Glu Glu Ala Cys Gln Leu Thr Pro Pro His Ser
2525                2530                2535

Ala Arg Ser Lys Tyr Gly Phe Gly Ala Lys Glu Val Arg Ser Leu
2540                2545                2550

Ser Gly Arg Ala Val Asn His Ile Lys Ser Val Trp Lys Asp Leu
2555                2560                2565

-continued

```
Leu Glu Asp Pro Gln Thr Pro Ile Pro Thr Thr Ile Met Ala Lys
    2570            2575            2580

Asn Glu Val Phe Cys Val Asp Pro Ala Lys Gly Gly Lys Lys Pro
    2585            2590            2595

Ala Arg Leu Ile Val Tyr Pro Asp Leu Gly Val Arg Val Cys Glu
    2600            2605            2610

Lys Met Ala Leu Tyr Asp Ile Thr Gln Lys Leu Pro Gln Ala Val
    2615            2620            2625

Met Gly Ala Ser Tyr Gly Phe Gln Tyr Ser Pro Ala Gln Arg Val
    2630            2635            2640

Glu Tyr Leu Leu Lys Ala Trp Ala Glu Lys Lys Asp Pro Met Gly
    2645            2650            2655

Phe Ser Tyr Asp Thr Arg Cys Phe Asp Ser Thr Val Thr Glu Arg
    2660            2665            2670

Asp Ile Arg Thr Glu Glu Ser Ile Tyr Gln Ala Cys Ser Leu Pro
    2675            2680            2685

Glu Glu Ala Arg Thr Ala Ile His Ser Leu Thr Glu Arg Leu Tyr
    2690            2695            2700

Val Gly Gly Pro Met Phe Asn Ser Lys Gly Gln Thr Cys Gly Tyr
    2705            2710            2715

Arg Arg Cys Arg Ala Ser Gly Val Leu Thr Thr Ser Met Gly Asn
    2720            2725            2730

Thr Ile Thr Cys Tyr Val Lys Ala Leu Ala Ala Cys Lys Ala Ala
    2735            2740            2745

Gly Ile Val Ala Pro Thr Met Leu Val Cys Gly Asp Asp Leu Val
    2750            2755            2760

Val Ile Ser Glu Ser Gln Gly Thr Glu Glu Asp Glu Arg Asn Leu
    2765            2770            2775

Arg Ala Phe Thr Glu Ala Met Thr Arg Tyr Ser Ala Pro Pro Gly
    2780            2785            2790

Asp Pro Pro Arg Pro Glu Tyr Asp Leu Glu Leu Ile Thr Ser Cys
    2795            2800            2805

Ser Ser Asn Val Ser Val Ala Leu Gly Pro Arg Gly Arg Arg Arg
    2810            2815            2820

Tyr Tyr Leu Thr Arg Asp Pro Thr Thr Pro Leu Ala Arg Ala Ala
    2825            2830            2835

Trp Glu Thr Val Arg His Ser Pro Ile Asn Ser Trp Leu Gly Asn
    2840            2845            2850

Ile Ile Gln Tyr Ala Pro Thr Ile Trp Val Arg Met Val Leu Met
    2855            2860            2865

Thr His Phe Phe Ser Ile Leu Met Val Gln Asp Thr Leu Asp Gln
    2870            2875            2880

Asn Leu Asn Phe Glu Met Tyr Gly Ser Val Tyr Ser Val Asn Pro
    2885            2890            2895

Leu Asp Leu Pro Ala Ile Ile Glu Arg Leu His Gly Leu Asp Ala
    2900            2905            2910

Phe Ser Met His Thr Tyr Ser His His Glu Leu Thr Arg Val Ala
    2915            2920            2925

Ser Ala Leu Arg Lys Leu Gly Ala Pro Pro Leu Arg Val Trp Lys
    2930            2935            2940

Ser Arg Ala Arg Ala Val Arg Ala Ser Leu Ile Ser Arg Gly Gly
    2945            2950            2955

Lys Ala Ala Val Cys Gly Arg Tyr Leu Phe Asn Trp Ala Val Lys
```

|     |     |     |     |     |     |     |     |     |     |
|---|---|---|---|---|---|---|---|---|---|
|     |     | 2960 |     |     | 2965 |     |     | 2970 |     |
| Thr | Lys | Leu | Lys | Leu | Thr | Pro | Leu | Pro | Glu | Ala | Arg | Leu | Leu | Asp |
|     |     | 2975 |     |     | 2980 |     |     | 2985 |     |
| Leu | Ser | Ser | Trp | Phe | Thr | Val | Gly | Ala | Gly | Gly | Gly | Asp | Ile | Phe |
|     |     | 2990 |     |     | 2995 |     |     | 3000 |     |
| His | Ser | Val | Ser | Arg | Ala | Arg | Pro | Arg | Ser | Leu | Leu | Phe | Gly | Leu |
|     |     | 3005 |     |     | 3010 |     |     | 3015 |     |
| Leu | Leu | Leu | Phe | Val | Gly | Val | Gly | Leu | Phe | Leu | Leu | Pro | Ala | Arg |
|     |     | 3020 |     |     | 3025 |     |     | 3030 |     |

<210> SEQ ID NO 29
<211> LENGTH: 9678
<212> TYPE: DNA
<213> ORGANISM: Artificial Sequence
<220> FEATURE:
<223> OTHER INFORMATION: Chemically synthesized chimeric DNA

<400> SEQUENCE: 29

| acctgcccct aatagggggcg acactccgcc atgaatcact ccctgtgag gaactactgt | 60 |
|---|---|
| cttcacgcag aaagcgccta gccatggcgt tagtatgagt gtcgtacagc ctccaggccc | 120 |
| cccctcccg ggagagccat agtggtctgc ggaaccggtg agtacaccgg aattgccggg | 180 |
| aagactgggg cctttcttgg ataaacccac tctatgcccg gccatttggg cgtgcccccg | 240 |
| caagactgct agccgagtag cgttgggttg cgaaaggcct tgtggtactg cctgataggg | 300 |
| tgcttgcgag tgccccggga ggtctcgtag accgtgcacc atgagcacaa atcctaaacc | 360 |
| tcaaagaaaa accaaaagaa acaccaaccg tcgcccacaa gacgttaagt ttccgggcgg | 420 |
| cggccagatc gttggcggag tatacttgtt gccgcgcagg ggcccaggt tgggtgtgcg | 480 |
| cgcgacaagg aagacttcgg agcggtccca gccacgtgga aggcgccagc ccatccctaa | 540 |
| agatcggcgc tccactggca aatcctgggg aaaaccagga taccctggc ccctatacgg | 600 |
| gaatgaggga ctcggctggg caggatggct cctgtccccc cgaggttccc gtccctcttg | 660 |
| gggccccaat gacccccggc ataggtcgcg caacgtgggt aaggtcatcg ataccctaac | 720 |
| gtgcggcttt gccgacctca tggggtacat ccctgtcgtg ggcgcccgc tcggcggcgt | 780 |
| cgccagagct ctcgcgcatg gcgtgagagt cctggaggac ggggttaatt ttgcaacagg | 840 |
| gaacttaccc ggttgctcct tttctatctt cttgctggcc ctgctgtcct gcatcaccac | 900 |
| ccggtctcc gctgccgaag tgaagaacat cagtaccggc tacatggtga ctaacgactg | 960 |
| caccaatgac agcattacct ggcagctcca ggctgctgtc ctccacgtcc ccgggtgcgt | 1020 |
| cccgtgcgag aaagtgggga atgcatctca gtgctggata ccggtctcac cgaatgtggc | 1080 |
| cgtgcagcgg cccggcgccc tcacgcaggg cttgcgacg cacatcgaca tggttgtgat | 1140 |
| gtccgccacg ctctgctctg ccctctacgt ggggggacctc tgcggtgggg tgatgctcgc | 1200 |
| agcccaaatg ttcattgtct cgccgcagca ccactggttt gtccaagact gcaattgctc | 1260 |
| catctaccct ggtaccatca ctggacaccg catggcatgg gacatgatga tgaactggtc | 1320 |
| gcccacggct accatgatct ggcgtacgc gatgcgtgtc cccgaggtca ttatagacat | 1380 |
| cattagcggg gctcattggg gcgtcatgtt cggcttggcc tacttctcta tgcagggagc | 1440 |
| gtgggcgaaa gtcgttgtca tccttctgtt ggccgccggg gtggacgcgc gcacccatac | 1500 |
| tgttgggggt tctgccgcgc agaccaccgg gcgcctcacc agcttatttg acatgggccc | 1560 |
| caggcagaaa atccagctcg ttaacaccaa tggcagctgg cacatcaacc gcaccgccct | 1620 |
| gaactgcaat gactccttgc acaccggctt tatcgcgtct ctgttctaca cccacagctt | 1680 |

```
caactcgtca ggatgtcccg aacgcatgtc cgcctgccgc agtatcgagg ccttccgggt    1740
gggatggggc gccttgcaat atgaggataa tgtcaccaat ccagaggata tgagaccccta   1800 ttgctggcac tacccaccaa ggcagtgtgg cgtggtctcc gcgaagactg tgtgtggccc    1860
agtgtactgt ttcacccccca gcccagtggt agtgggcacg accgacaggc ttggagcgcc   1920
cacttacacg tgggggggaga atgagacaga tgtcttccta ttgaacagca ctcgaccacc   1980
gctggggtca tggttcggct gcacgtggat gaactcttct ggctacacca agacttgcgg    2040
cgcaccaccc tgccgtacta gagctgactt caacgccagc acggacctgt tgtgccccac    2100
ggactgtttt aggaagcatc ctgataccac ttacctcaaa tgcggctctg ggccctggct    2160
cacgccaagg tgcctgatcg actaccccta caggctctgg cattacccct gcacagttaa    2220
ctataccatc ttcaaaataa ggatgtatgt gggagggggtt gagcacaggc tcacggctgc   2280
atgcaatttc actcgtgggg atcgttgcaa cttggaggac agagacagaa gtcaactgtc    2340
tcctttgttg cactccacca cggaatgggc cattttacct tgctcttact cggacctgcc    2400
cgccttgtcg actggtcttc tccacctcca ccaaaacatc gtggacgtac aattcatgta    2460
tggcctatca cctgccctca caaaatacat cgtccgatgg gagtgggtaa tactcttatt    2520
cctgctctta gcggacgcca gggtttgcgc ctgcttatgg atgctcatct tgttgggcca    2580
ggccgaagca gcactagaga agctggtcat cttgcacgct cgcagcgcag ctagctgcaa    2640
tggcttccta tattttgtca tctttttcgt ggctgcttgg tacatcaagg gtcgggtagt    2700 cccccttagct acctattccc tcactggcct gtggtccttt agcctactgc tcctagcatt    2760
gccccaacag gcttatgctt atgacgcatc tgtgcatggc cagataggag cggctctgct    2820
ggtaatgatc accctcttca cactcacccc ggggtataag accctcctcg gccagtgtct    2880
gtggtggttg tgctatctcc tgaccctggg ggaagccatg attcaggagt gggtaccacc    2940
catgcaggtg cgcggcggcc gcgatggcat cgcgtgggcc gtcactatat tctgcccggg    3000
tgtggtgttt gacattacca aatggctttt ggcgttgctt gggcctgctt acctcttaag    3060
ggccgctttg acacatgtgc cgtacttcgt cagagctcac gctctgataa gggtatgcgc    3120
tttggtgaag cagctcgcgg gggtaggta tgttcaggtg gcgctattgg cccttggcag    3180
gtggactggc acctacatct atgaccacct cacacctatg tcggactggg ccgctagcgg    3240
cctgcgcgac ttagcggtcg ccgtggaacc catcatcttc agtccgatgg agaagaaggt    3300
catcgtctgg ggagcggaga cggctgcatg tggggacatt ctacatggac ttcccgtgtc    3360
cgcccgactc ggccaggaga tcctcctcgg cccagctgat ggctacacct caagggggtg    3420
gaagctcctt gctcccatca ctgcttatgc ccagcaaaca cgaggcctcc tgggcgccat    3480
agtggtgagt atgacgggc gtgacaggac agaacaggcc gggaagtcc aaatcctgtc     3540 cacagtctct cagtccttcc tcggaacaac catctcgggg gttttgtgga ctgtttacca    3600
cggagctggc aacaagactc tagccggctt acggggtccg gtcacgcaga tgtactcgag    3660
tgctgagggg gacttggtag ctggcccag ccccctggg accaagtctt tggagccgtg     3720
caagtgtgga gccgtcgacc tatatctggt cacgcgcaac gctgatgtca tcccggctcg    3780
gagacgcggg gacaagcggg gagcattgct ctccccgaga cccatttcga ccttgaaggg    3840
gtcctcgggg gggccggtgc tctgccctag gggccacgtc gttgggctct ccgagcagc    3900 tgtgtgctct cggggcgtgg ccaaatccat cgatttcatc cccgttgaga cactcgacgt    3960
tgttacaagg tctcccactt tcagtgacaa cagcacgcca ccggctgtgc cccagaccta    4020
tcaggtcggg tacttgcatg ctccaactgg cagtggaaag agcaccaagg tccctgtcgc    4080
```

```
gtatgccgcc caggggtaca aagtactagt gcttaacccc tcggtagctg ccaccctggg   4140
gtttggggcg tacctatcca aggcacatgg catcaatccc aacattagga ctggagtcag   4200
gaccgtgatg accggggagg ccatcacgta ctccacatat ggcaaatttc tcgccgatgg   4260
gggctgcgct agcggcgcct atgacatcat catatgcgat gaatgccacg ctgtggatgc   4320
tacctccatt ctcggcatcg gaacggtcct tgatcaagca gagacagccg gggtcagact   4380
aactgtgctg gctacggcca cacccccccgg gtcagtgaca accccccatc ccgatataga   4440
agaggtaggc ctcgggcggg agggtgagat ccccttctat gggagggcga ttcccctatc   4500
ctgcatcaag ggagggagac acctgatttt ctgccactca agaaaaagt gtgacgagct    4560
cgcggcggcc cttcggggca tgggcttgaa tgccgtggca tactatagag ggttggacgt   4620
ctccataata ccagctcagg gagatgtggt ggtcgtcgcc accgacgccc tcatgacggg   4680
gtacactgga gactttgact ccgtgatcga ctgcaatgta gcggtcaccc aagctgtcga   4740
cttcagcctg gaccccacct tcactataac cacacagact gtcccacaag acgctgtctc   4800
acgcagtcag cgccgcgggc gcacaggtag aggaagacag ggcacttata ggtatgtttc   4860
cactggtgaa cgagcctcag gaatgtttga cagtgtagtg ctttgtgagt gctacgacgc   4920
aggggctgcg tggtacgatc tcacaccagc ggagaccacc gtcaggctta gagcgtattt   4980
caacacgccc ggcctacccg tgtgtcaaga ccatcttgaa ttttgggagg cagttttcac   5040
cggcctcaca cacatagacg cccacttcct ctcccaaaca aagcaagcgg gggagaactt   5100
cgcgtaccta gtagcctacc aagctacggt gtgcgccaga gccaaggccc ctcccccgtc   5160
ctgggacgcc atgtggaagt gcctggcccg actcaagcct acgcttgcgg gccccacacc   5220
tctcctgtac cgtttgggcc ctattaccaa tgaggtcacc ctcacacacc ctgggacgaa   5280
gtacatcgcc acatgcatgc aagctgacct tgaggtcatg accagcacgt gggtcctagc   5340
tggaggagtc ctggcagccg tcgccgcata ttgcctggcg actggatgcg tttccatcat   5400
cggccgcttg cacgtcaacc agcgagtcgt cgttgcgccg gataaggagg tcctgtatga   5460
ggcttttgat gagatggagg aatgcgcctc tagggcggct ctcatcgaag aggggcagcg   5520
gatagccgag atgttgaagt ccaagatcca aggcttgctg cagcaggcct ctaagcaggc   5580
ccaggacata caacccgcta tgcaggcttc atggcccaaa gtggaacaat tttgggccag   5640
acacatgtgg aacttcatta gcggcatcca atacctcgca ggattgtcaa cactgccagg   5700
gaaccccgcg gtggcttcca tgatggcatt cagtgccgcc ctcaccagtc cgttgtcgac   5760
cagtaccacc atccttctca acatcatggg aggctggtta gcgtcccaga tcgcaccacc   5820
cgcgggggcc accggctttg tcgtcagtgg cctggtgggg gctgccgtgg gcagcatagg   5880
cctgggtaag gtgctggtgg acatcctggc aggatatggt gcgggcattt cgggggccct   5940
cgtcgcattc aagatcatgt ctggcgagaa gccctctatg aagatgtca tcaatctact    6000
gcctgggatc ctgtctccgg gagccctggt ggtgggggtc atctgcgcgg ccattctgcg   6060
ccgccacgtg gaccgggggg agggcgcggt ccaatggatg aacaggctta ttgccttttgc   6120
ttccagagga aaccacgtcg cccctactca ctacgtgacg gagtcggatg cgtcgcagcg   6180
tgtgacccaa ctacttggct ctcttactat aaccagccta ctcagaagac tccacaattg   6240
gataactgag gactgcccca tcccatgctc cggatcctgg ctccgcgacg tgtgggactg   6300
ggtttgcacc atcttgacag acttcaaaaa ttggctgacc tctaaattgt tccccaagct   6360
gcccggcctc cccttcatct cttgtcaaaa ggggtacaag ggtgtgtggg ccggcactgg   6420
catcatgacc acgcgctgcc cttgcggcgc caacatctct ggcaatgtcc gcctgggctc   6480
```

```
tatgaggatc acagggccta aaacctgcat gaacacctgg caggggacct ttcctatcaa    6540
ttgctacacg gagggccagt gcgcgccgaa accccccacg aactacaaga ccgccatctg    6600
gagggtggcg gcctcggagt acgcggaggt gacgcagcat gggtcgtact cctatgtaac    6660
aggactgacc actgacaatc tgaaaattcc ttgccaacta ccttctccag agttttctc    6720 ctgggtggac ggtgtgcaga tccataggtt tgcacccaca ccaaagccgt ttttccggga    6780
tgaggtctcg ttctgcgttg ggcttaattc ctatgctgtc gggtcccagc ttccctgtga    6840
acctgagccc gacgcagacg tattgaggtc catgctaaca gatccgcccc acatcacggc    6900
ggagactgcg gcgcggcgct tggcacgggg atcacctcca tctgaggcga gctcctcagt    6960
gagccagcta tcagcaccgt cgctgcgggc cacctgcacc acccacagca cacctatga    7020 cgtggacatg gtcgatgcca acctgctcat ggagggcgt gtggctcaga cagagcctga    7080
gtccagggtg cccgttctgg actttctcga gccaatggcc gaggaagaga gcgaccttga    7140
gccctcaata ccatcggagt gcatgctccc caggagcggg tttccacggg ccttaccggc    7200
ttgggcacgg cctgactaca acccgccgct cgtggaatcg tggaggaggc cagattacca    7260
accgcccacc gttgctggtt gtgctctccc cccccccaag aaggcccga cgcctccccc    7320 aaggagacgc cggacagtgg gtctgagcga gagcaccata tcagaagccc tccagcaact    7380
ggccatcaag acctttggcc agccccctc gagcggtgat gcaggctcgt ccacgggggc    7440
gggcgccgcc gaatccggcg gtccgacgtc ccctggtgag ccggccccct cagagacagg    7500
ttccgcctcc tctatgcccc cctcgagggg ggagcctgga gatccggacc tggagtctga    7560
tcaggtagag cttcaacctc cccccaggg ggggggggta gctcccggtt cgggctcggg    7620
gtcttggtct acttgctccg aggaggacga taccaccgtg tgctgctcca tgtcatactc    7680
ctggaccggg gctctaataa ctccctgtag ccccgaagag gaaaagttgc caatcaaccc    7740
tttgagtaac tcgctgttgc gataccataa caaggtgtac tgtacaacat caaagagcgc    7800
ctcacagagg gctaaaaagg taacttttga caggacgcaa gtgctcgacg cccattatga    7860
ctcagtctta aaggacatca agctagcggc ttccaaggtc agcgcaaggc tcctcacctt    7920
ggaggaggcg tgccagttga ctccacccca ttctgcaaga tccaagtatg gattcggggc    7980
caaggaggtc cgcagcttgt ccgggagggc cgttaaccac atcaagtccg tgtggaagga    8040
cctcctggaa gacccacaaa caccaattcc cacaaccatc atggccaaaa atgaggtgtt    8100
ctgcgtggac cccgccaagg ggggtaagaa accagctcgc ctcatcgttt accctgacct    8160
cggcgtccgg gtctgcgaga aaatggccct ctatgacatt acacaaaagc ttcctcaggc    8220
ggtaatggga gcttcctatg cttccagta ctcccctgcc caacgggtgg agtatctctt    8280
gaaagcatgg gcgaaaaga aggacccccat gggttttcg tatgataccc gatgcttcga    8340
ctcaaccgtc actgagagag acatcaggac cgaggagtcc atataccagg cctgctccct    8400
gcccgaggag gcccgcactg ccatacactc gctgactgag agactttacg taggagggcc    8460
catgttcaac agcaagggtc aaacctgcgg ttacagacgt tgccgcgcca gcgggtgct    8520 aaccactagc atgggtaaca ccatcacatg ctatgtgaaa gccctagcgg cctgcaaggc    8580
tgcggggata gttgcgccca caatgctggt atgcggcgat gacctagtag tcatctcaga    8640 aagcagggg actgaggagg acgagcggaa cctgagagcc ttcacggagg ccatgaccag    8700
gtactctgcc cctcctggtg atccccccag accggaatat gacctggagc taataacatc    8760
ctgttcctca aatgtgtctg tggcgttggg cccgcgggc cgccgcagat actacctgac    8820
cagagaccca accactccac tcgcccgggc tgcctgggaa acagttagac actcccctat    8880
```

-continued

| | |
|---|---|
| caattcatgg ctgggaaaca tcatccagta tgctccaacc atatgggttc gcatggtcct | 8940 |
| aatgacacac ttcttctcca ttctcatggt ccaagacacc ctggaccaga acctcaactt | 9000 |
| tgagatgtat ggatcagtat actccgtgaa tcctttggac cttccagcca taattgagag | 9060 |
| gttacacggg cttgacgcct tttctatgca cacatactct caccacgaac tgacgcgggt | 9120 |
| ggcttcagcc ctcagaaaac ttggggcgcc accctcagg gtgtggaaga gtcgggctcg | 9180 |
| cgcagtcagg gcgtccctca tctcccgtgg agggaaagcg gccgtttgcg gccgatatct | 9240 |
| cttcaattgg gcggtgaaga ccaagctcaa actcactcca ttgccggagg cgcgcctact | 9300 |
| ggacttatcc agttggttca ccgtcggcgc cggcgggggc gacattttc acagcgtgtc | 9360 |
| gcgcgcccga ccccgctcat tactcttcgg cctactccta cttttcgtag gggtaggcct | 9420 |
| cttcctactc cccgctcggt agagcggcac acactaggta cactccatag ctaactgttc | 9480 |
| cttttttttt ttttttttt tttttttttt tttttttttt ttttctttt tttttttttc | 9540 |
| cctctttctt cccttctcat cttattctac tttctttctt ggtggctcca tcttagccct | 9600 |
| agtcacggct agctgtgaaa ggtccgtgag ccgcatgact gcagagagtg ccgtaactgg | 9660 |
| tctctctgca gatcatgt | 9678 |

<210> SEQ ID NO 30
<211> LENGTH: 9666
<212> TYPE: DNA
<213> ORGANISM: Artificial Sequence
<220> FEATURE:
<223> OTHER INFORMATION: Chemically synthesized chimeric DNA

<400> SEQUENCE: 30

| | |
|---|---|
| acctgcccct aatagggcg acactccgcc atgaatcact ccctgtgag gaactactgt | 60 |
| cttcacgcag aaagcgccta gccatggcgt tagtatgagt gtcgtacagc ctccaggccc | 120 |
| cccctcccg ggagagccat agtggtctgc ggaaccggtg agtacaccgg aattgccagg | 180 |
| acgaccgggt cctttcttgg ataaacccgc tcaatgcctg gagatttggg cgtgcccccg | 240 |
| caagactgct agccgagtag tgttgggtcg cgaaaggcct tgtggtactg cctgataggg | 300 |
| tgcttgcgag tgccccggga ggtctcgtag accgtgcacc atgagcacga atcctaaacc | 360 |
| tcaaagaaaa accaaacgta acaccaaccg tcgcccacag gacgtcaagt tcccgggtgg | 420 |
| cggtcagatc gttggtggag tttacttgtt gccgcgcagg ggccctagat tgggtgtgcg | 480 |
| cgcgacgagg aagacttccg agcggtcgca acctcgaggt agacgtcagc ctatccccaa | 540 |
| ggcacgtcgg cccgagggca ggacctgggc tcagcccggg tacccttggc ccctctatgg | 600 |
| caatgagggt tgcgggtggg cgggatggct cctgtctccc cgtggctctc ggcctagctg | 660 |
| gggcccaca gaccccggc gtaggtcgcg caatttgggt aaggtcatcg ataccttac | 720 |
| gtgcggcttc gccgacctca tggggtacat accgctcgtc ggcgcccctc ttggaggcgc | 780 |
| tgccagggc ctggcgcatg gcgtccgggt tctggaagac ggcgtgaact atgcaacagg | 840 |
| gaaccttcct ggttgctctt tctctatctt ccttctggcc ctgctctctt gcctgactgt | 900 |
| gcccgcttca gcctaccaag tgcgcaattc ctcgggcctt taccatgtca ccaatgattg | 960 |
| ccctaactcg agtattgtgt acgaggcggc cgatgccatc ctgcacactc ggggtgtgt | 1020 |
| cccttgcgtt cgcgagggta acgctcgag gtgttgggtg gcggtgaccc ccacggtggc | 1080 |
| caccagggac ggcaaactcc ccacaacgca gcttcgacgt catatcgatc tgcttgtcgg | 1140 |
| gagcgccacc ctctgctcgg ccctctacgt gggggacctg tgcggtgtctg tcttctcttgt | 1200 |
| tggtcaactg tttaccttct ctcccaggcg ccactggacg acgcaagact gcaattgttc | 1260 |

-continued

```
tatctatccc ggccatataa cgggtcatcg catggcatgg gatatgatga tgaactggtc    1320
ccctacggca gcgttggtgg tagctcagct gctccggatc ccacaagcca tcatggacat    1380
gatcgctggt gctcactggg gagtcctggc gggcatagcg tatttctcca tggtggggaa    1440
ctgggcgaag gtcctggtag tgctgctgct atttgccggc gtcgacgcgg aaacccacgt    1500 caccgggga aatgccggcc gcaccacggc tgggcttgtt ggtctcctta caccaggcgc    1560
caagcagaac atccaactga tcaacaccaa cggcagttgg cacatcaata gcacggcctt    1620
gaattgcaat gaaagcctta acaccggctg gttagcaggg ctcttctatc aacacaaatt    1680
caactcttca ggctgtcctg agaggttggc cagctgccga cgccttaccg attttgccca    1740
gggctggggt cctatcagtt atgccaacgg aagcggcctc gacgaacgcc cctactgctg    1800
gcactaccct ccaagacctt gtggcattgt gcccgcaaag agcgtgtgtg gcccggtata    1860
ttgcttcact cccagccccg tggtggtggg aacgaccgac aggtcgggcg cgcctaccta    1920
cagctggggt gcaaatgata cggatgtctt cgtccttaac aacaccaggc caccgctggg    1980
caattggttc ggttgtacct ggatgaactc aactggattc accaaagtgt gcggagcgcc    2040
cccttgtgtc atcggagggg tgggcaacaa caccttgctc tgccccactg attgcttccg    2100
caaacatccg gaagccacat actctcggtg cggctccggt ccctggatta cacccaggtg    2160
catggtcgac tacccgtata ggctttggca ctatccttgt accatcaatt acaccatatt    2220
caaagtcagg atgtacgtgg gaggggtcga gcacaggctg gaagcggcct gcaactggac    2280
gcggggcgaa cgctgtgatc tggaagacag ggacaggtcc gagctcagcc cgttgctgct    2340
gtccaccaca cagtggcagg tccttccgtg ttctttcacg accctgccag ccttgtccac    2400
cggcctcatc cacctccacc agaacattgt ggacgtgcag tacttgtacg gggtagggtc    2460
aagcatcgcg tcctgggcca ttaagtggga gtacgtcgtt ctcctgttcc ttctgcttgc    2520
agacgcgcgc gtctgctcct gcttgtggat gatgttactc atatcccaag cggaggcggc    2580
tttggagaac ctcgtaatac tcaatgcagc atccctggcc gggacgcacg tcttgtgtc    2640 cttcctcgtg ttcttctgct ttgcgtggta tctgaagggt aggtgggtgc ccggagcggt    2700
ctacgccctc tacgggatgt ggcctctcct cctgctcctg ctggcgttgc ctcagcgggc    2760
atacgcatat gacgcacctg tgcacggaca gataggcgtg ggtttgttga tattgatcac    2820
cctcttcaca ctcaccccgg ggtataagac cctcctcggc cagtgtctgt ggtggttgtg    2880
ctatctcctg accctggggg aagccatgat tcaggagtgg gtaccaccca tgcaggtgcg    2940
cggcggccgc gatggcatcg cgtgggccgt cactatattc tgcccgggtg tggtgtttga    3000
cattaccaaa tggcttttgg cgttgcttgg gcctgcttac ctcttaaggg ccgctttgac    3060
acatgtgccg tacttcgtca gagctcacgc tctgataagg gtatgcgctt tggtgaagca    3120
gctcgcgggg ggtaggtatg ttcaggtggc gctattggcc cttggcaggt ggactggcac    3180
ctacatctat gaccacctca cacctatgtc ggactgggcc gctagcggcc tgcgcgactt    3240
agcggtcgcc gtggaaccca tcatcttcag tccgatggag aagaaggtca tcgtctgggg    3300
agcggagacg gctgcatgtg gggacattct acatggactt cccgtgtccg cccgactcgg    3360
ccaggagatc ctcctcggcc cagctgatgg ctacacctcc aagggggtgga agctccttgc    3420 tcccatcact gcttatgccc agcaaacacg aggcctcctg ggcgccatag tggtgagtat    3480 gacgggcgt gacaggacag aacaggccgg ggaagtccaa atcctgtcca cagtctctca    3540
gtccttcctc ggaacaacca tctcgggggt tttgtggact gtttaccacg gagctggcaa    3600
caagactcta gccggcttac ggggtccggt cacgcagatg tactcgagtg ctgaggggga    3660
```

```
cttggtaggc tggcccagcc ccctgggac caagtctttg gagccgtgca agtgtggagc    3720
cgtcgaccta tatctggtca cgcggaacgc tgatgtcatc ccggctcgga gacgcgggga   3780
caagcgggga gcattgctct ccccgagacc catttcgacc ttgaaggggt cctcgggggg   3840
gccggtgctc tgcccctaggg gccacgtcgt tgggctcttc cgagcagctg tgtgctctcg  3900
gggcgtggcc aaatccatcg atttcatccc cgttgagaca ctcgacgttg ttacaaggtc   3960
tcccactttc agtgacaaca gcacgccacc ggctgtgccc cagacctatc aggtcggta    4020
cttgcatgct ccaactggca gtggaaagag caccaaggtc cctgtcgcgt atgccgccca   4080
ggggtacaaa gtactagtgc ttaaccccte ggtagctgcc accctggggt ttggggcgta   4140
cctatccaag gcacatggca tcaatcccaa cattaggact ggagtcagga ccgtgatgac   4200
cggggaggcc atcacgtact ccacatatgg caaatttctc gccgatgggg gctgcgctag   4260
cggcgcctat gacatcatca tatgcgatga atgccacgct gtggatgcta cctccattct   4320
cggcatcgga acggtccttg atcaagcaga gacagccggg gtcagactaa ctgtgctggc   4380
tacggccaca ccccccgggt cagtgacaac ccccatccc gatatagaag aggtaggcct    4440
cgggcgggag ggtgagatcc ccttctatgg gagggcgatt cccctatcct gcatcaaggg   4500
agggagacac ctgattttct gccactcaaa gaaaaagtgt gacgagctcg cggcggccct   4560
tcggggcatg gcttgaatg ccgtggcata ctatagaggg ttggacgtct ccataataacc   4620
agctcaggga gatgtggtgg tcgtcgccac cgacgccctc atgacggggt acactggaga   4680
ctttgactcc gtgatcgact gcaatgtagc ggtcacccaa gctgtcgact tcagcctgga   4740
ccccaccttc actataacca cacagactgt cccacaagac gctgtctcac gcagtcagcg   4800
ccgcggggcgc acaggtagag gaagacaggg cacttatagg tatgtttcca ctggtgaacg   4860
agcctcagga atgtttgaca gtgtagtgct ttgtgagtgc tacgacgcag gggctgcgtg   4920
gtacgatctc acaccagcgg agaccaccgt caggcttaga gcgtatttca acacgcccgg   4980
cctacccgtg tgtcaagacc atcttgaatt ttgggaggca gttttcaccg gcctcacaca   5040
catagacgcc cacttcctct cccaaacaaa gcaagcgggg gagaacttcg cgtacctagt   5100
agcctaccaa gctacggtgt gcgccagagc caaggcccct cccccgtcct gggacgccat   5160
gtggaagtgc ctggcccgac tcaagcctac gcttgcgggc cccacacctc tcctgtaccg   5220
tttgggcccct attaccaatg aggtcaccct cacacaccct gggacgaagt acatcgccac   5280
atgcatgcaa gctgaccttg aggtcatgac cagcacgtgg gtcctagctg gaggagtcct   5340
ggcagccgtc gccgcatatt gcctggcgac tggatgcgtt ccatcatcg gccgcttgca    5400
cgtcaaccag cgagtcgtcg ttgcgccgga taaggaggtc ctgtatgagg cttttgatga   5460
gatggaggaa tgcgcctcta gggcggctct catcgaagag gggcagcgga tagccgagat   5520
gttgaagtcc aagatccaag gcttgctgca gcaggcctct aagcaggccc aggacataca   5580
acccgctatg caggcttcat ggcccaaagt ggaacaattt tgggcagac acatgtggaa    5640
cttcattagc ggcatccaat acctcgcagg attgtcaaca ctgccaggga accccgcggt   5700
ggcttccatg atggcattca gtgccgccct caccagtccg ttgtcgacca gtaccaccat   5760
ccttctcaac atcatgggag ctggttagc gtcccagatc gcaccacccg cgggggccac    5820
cggctttgtc gtcagtggcc tggtgggggc tgccgtgggc agcataggcc tgggtaaggt   5880
gctggtggac atcctggcag gatatggtgc gggcatttcg ggggccctcg tcgcattcaa   5940
gatcatgtct ggcgagaagc cctctatgga agatgtcatc aatctactgc ctgggatcct   6000
gtctccggga gccctggtgg tggggggtca t ctgcgcggcc attctgcgcc gccacgtggg    6060
```

```
accgggggag ggcgcggtcc aatggatgaa caggcttatt gcctttgctt ccagaggaaa    6120
ccacgtcgcc cctactcact acgtgacgga gtcggatgcg tcgcagcgtg tgacccaact    6180
acttggctct cttactataa ccagcctact cagaagactc cacaattgga taactgagga    6240
ctgccccatc ccatgctccg gatcctggct ccgcgacgtg tgggactggg tttgcaccat    6300
cttgacagac ttcaaaaatt ggctgacctc taaattgttc cccaagctgc ccggcctccc    6360
cttcatctct tgtcaaaagg ggtacaaggg tgtgtgggcc ggcactggca tcatgaccac    6420
gcgctgccct tgcggcgcca acatctctgg caatgtccgc ctgggctcta tgaggatcac    6480
agggcctaaa acctgcatga acacctggca ggggaccttt cctatcaatt gctacacgga    6540
gggccagtgc gcgccgaaac cccccacgaa ctacaagacc gccatctgga gggtggcggc    6600
ctcggagtac gcggaggtga cgcagcatgg gtcgtactcc tatgtaacag gactgaccac    6660
tgacaatctg aaaattcctt gccaactacc ttctccagag ttttttctcct gggtggacgg    6720 tgtgcagatc cataggtttg cacccacacc aaagccgttt ttccgggatg aggtctcgtt    6780
ctgcgttggg cttaattcct atgctgtcgg gtcccagctt ccctgtgaac ctgagcccga    6840
cgcagacgta ttgaggtcca tgctaacaga tccgccccac atcacggcgg agactgcggc    6900
gcggcgcttg gcacggggat cacctccatc tgaggcgagc tcctcagtga gccagctatc    6960
agcaccgtcg ctgcgggcca cctgcaccac ccacagcaac acctatgacg tggacatggt    7020
cgatgccaac ctgctcatgg agggcggtgt ggctcagaca gagcctgagt ccagggtgcc    7080
cgttctggac tttctcgagc caatggccga ggaagagagc gaccttgagc cctcaatacc    7140
atcggagtgc atgctcccca ggagcgggtt tccacgggcc ttaccggctt gggcacggcc    7200
tgactacaac ccgccgctcg tggaatcgtg gaggaggcca gattaccaac cgcccaccgt    7260
tgctggttgt gctctccccc cccccaagaa ggccccgacg cctcccccaa ggagacgccg    7320
gacagtgggt ctgagcgaga gcaccatatc agaagccctc cagcaactgg ccatcaagac    7380
cttttggcca g cccccctcga gcggtgatgc aggctcgtcc acggggggcgg gcgccgccga    7440 atccggcggt ccgacgtccc ctggtgagcc ggccccctca gagacaggtt ccgcctcctc    7500
tatgcccccc ctcgaggggg agcctggaga tccggacctg gagtctgatc aggtagagct    7560
tcaacctccc ccccaggggg gggggtagc tcccggttcg ggctcggggt cttggtctac    7620
ttgctccgag gaggacgata ccaccgtgtg ctgctccatg tcatactcct ggaccggggc    7680
tctaataact ccctgtagcc ccgaagagga aaagttgcca atcaacccctt tgagtaactc    7740 gctgttgcga taccataaca aagtgtactg tacaacatca aagagcgcct cacagagggc    7800
taaaaaggta acttttgaca ggacgcaagt gctcgacgcc cattatgact cagtcttaaa    7860
ggacatcaag ctagcggctt ccaaggtcag cgcaaggctc ctcaccttgg aggaggcgtg    7920
ccagttgact ccaccccatt ctgcaagatc caagtatgga ttcgggggcca aggaggtccg    7980 cagcttgtcc ggggagggccg ttaaccacat caagtccgtg tggaaggacc tcctggaaga    8040
cccacaaaca ccaattccca caaccatcat ggccaaaaat gaggtgttct gcgtggaccc    8100
cgccaagggg ggtaagaaac cagctcgcct catcgtttac cctgacctcg cgtccgggt    8160 ctgcgagaaa atggccctct atgacattac acaaaagctt cctcaggcgg taatgggagc    8220
ttcctatggc ttccagtact cccctgccca acggtggag tatctcttga agcatgggc    8280 ggaaaagaag gaccccatgg gttttttcgta tgatacccga tgcttcgact caaccgtcac    8340
tgagagagac atcaggaccg aggagtccat ataccaggcc tgctccctgc ccagggaggc    8400
ccgcactgcc atacactcgc tgactgagag actttacgta ggagggccca tgttcaacag    8460
```

| | | | | |
|---|---|---|---|---|
| caagggtcaa | acctgcggtt | acagacgttg | ccgcgccagc | ggggtgctaa ccactagcat | 8520 |
| gggtaacacc | atcacatgct | atgtgaaagc | cctagcggcc | tgcaaggctg cggggatagt | 8580 |
| tgcgcccaca | atgctggtat | gcggcgatga | cctagtagtc | atctcagaaa gccaggggac | 8640 |
| tgaggaggac | gagcggaacc | tgagagcctt | cacggaggcc | atgaccaggt actctgcccc | 8700 |
| tcctggtgat | cccccagac | cggaatatga | cctggagcta | ataacatcct gttcctcaaa | 8760 |
| tgtgtctgtg | gcgttgggcc | cgcggggccg | ccgcagatac | tacctgacca gagacccaac | 8820 |
| cactccactc | gcccgggctg | cctgggaaac | agttagacac | tcccctatca attcatggct | 8880 |
| gggaaacatc | atccagtatg | ctccaaccat | atgggttcgc | atggtcctaa tgacacactt | 8940 |
| cttctccatt | ctcatggtcc | aagacaccct | ggaccagaac | ctcaactttg agatgtatgg | 9000 |
| atcagtatac | tccgtgaatc | ctttggacct | tccagccata | attgagaggt tacacgggct | 9060 |
| tgacgccttt | tctatgcaca | catactctca | ccacgaactg | acgcgggtgg cttcagccct | 9120 |
| cagaaaactt | ggggcgccac | ccctcagggt | gtggaagagt | cgggctcgcg cagtcagggc | 9180 |
| gtccctcatc | tcccgtggag | ggaaagcggc | cgtttgcggc | cgatatctct tcaattgggc | 9240 |
| ggtgaagacc | aagctcaaac | tcactccatt | gccggaggcg | cgcctactgg acttatccag | 9300 |
| ttggttcacc | gtcggcgccg | gcgggggcga | catttttcac | agcgtgtcgc gcgcccgacc | 9360 |
| ccgctcatta | ctcttcggcc | tactcctact | tttcgtaggg | gtaggcctct tcctactccc | 9420 |
| cgctcggtag | agcggcacac | actaggtaca | ctccatagct | aactgttcct tttttttttt | 9480 |
| tttttttttt | tttttttttt | tttttttttt | tctttttttt | ttttttttccc tctttcttcc | 9540 |
| cttctcatct | tattctactt | tctttcttgg | tggctccatc | ttagccctag tcacggctag | 9600 |
| ctgtgaaagg | tccgtgagcc | gcatgactgc | agagagtgcc | gtaactggtc tctctgcaga | 9660 |
| tcatgt | | | | | 9666 |

<210> SEQ ID NO 31
<211> LENGTH: 9666
<212> TYPE: DNA
<213> ORGANISM: Artificial Sequence
<220> FEATURE:
<223> OTHER INFORMATION: Synthetic DNA

<400> SEQUENCE: 31

| | | | | |
|---|---|---|---|---|
| acctgcccct | aatagggcg | acactccgcc | atgaatcact | cccctgtgag gaactactgt | 60 |
| cttcacgcag | aaagcgccta | gccatggcgt | tagtatgagt | gtcgtacagc ctccaggccc | 120 |
| cccctcccg | ggagagccat | agtggtctgc | ggaaccggtg | agtacaccgg aattgccagg | 180 |
| acgaccgggt | cctttcttgg | atcaacccgc | tcaatgcctg | gagatttggg cgtgcccccg | 240 |
| cgagactgct | agccgagtag | tgttgggtcg | cgaaaggcct | tgtggtactg cctgataggg | 300 |
| tgcttgcgag | tgccccggga | ggtctcgtag | accgtgcatc | atgagcacaa atcctaaacc | 360 |
| ccaaagaaaa | accaaacgta | acaccaaccg | tcgcccacag | gacgttaagt tcccgggcgg | 420 |
| tggtcagatc | gtcggtggag | tttacttgtt | gccgcgcagg | ggcccaggt tgggtgtgcg | 480 |
| tgcgactagg | aagacttccg | agcggtcgca | acctcgtgga | aggcgacaac ctatccccaa | 540 |
| ggctcgccgg | cccgagggca | ggacctgggc | tcagcctggg | tatccttggc ccctctatgg | 600 |
| caatgagggc | ttggggtggg | caggatggct | cctgtcaccc | cgcggctctc ggcctagttg | 660 |
| gggccctaat | gacccccggc | gtaggtcgcg | taatttgggt | aaggtcatcg atacccttac | 720 |
| atgcggcttc | gccgacctca | tggggtacat | cccgcttgtc | ggcgcccct taggggcgc | 780 |
| tgccagggcc | ctggcacatg | gtgtccgggt | tctggaggac | ggcgtgaact atgcaacagg | 840 |

```
gaatttgccc ggttgctctt tctctatctt cctcttagct ctgctgtcct gtttgaccat    900
cccagcttcc gcttatgaag tgcgcaacgt gtccgggata taccatgtca caaacgactg    960
ctccaactca agcattgtgt atgaggcggc ggacgtgatc atgcatgccc ccgggtgcgt   1020
gccctgcgtt cgggagaaca attcctcccg ttgctgggta cgctcactc ccacgctcgc    1080 ggccaggaat gccagcgtcc ccactacgac attacgacgc cacgtcgact tgctcgttgg   1140
gacggctgct ttctgctccg ctatgtacgt ggggatctc tgcggatctg ttttcctcat    1200
ctcccagctg ttcaccttct cgcctcgccg gcatgagaca gtacaggact gcaactgctc   1260
aatctatccc ggccacgtat caggccatcg tatggcttgg gatatgatga tgaactggtc   1320
gcccacggca gccttagtgg tgtcgcagtt actccggatc ccacaagctg tcatggacat   1380
ggtggcgggg gcccactggg gagtcctagc gggccttgcc tactattcca tggtggggaa   1440
ctgggctaag gttttgattg tgatgctact ctttgccggc gttgacgggc atacccgcgt   1500 gacgggggg gtgcaaggcc atgtcacctc tacactcacg tccctcttta gacctggggc    1560
gtcccagaaa attcagcttg taaacaccaa tggcagttgg catatcaaca ggactgccct   1620
gaactgcaat gactccctca aaactgggtt tcttgccgcg ctgttctaca cacacaagtt   1680
caacgcgtcc ggatgcccgg agcgcatggc cagctgtcgc tccattgaca agttcgacca   1740 gggatgggt cccatcacct atgctcaacc tgacaactcg gaccagaggc cgtattgctg    1800
gcactacgca cctcgacagt gtggtatcgt acccgcgtcg caggtgtgcg gtccagtgta   1860
ttgcttcacc ccaagccctg ttgtagtggg gacgaccgat cgtttcggcg cccctacgta   1920
taactggggg gacaatgaga cggacgtgct gctcctaaac aacacgcggc cgccgcatgg   1980
caactggttc ggctgtacat ggatgaatag cactgggttc accaagacgt gcggaggccc   2040
cccgtgtaac atcagggggg tcggcaacaa caccttgacc tgccccacgg actgcttccg   2100
gaagcacccc gacgccactt acacaaaatg tggttcgggc ccttggttga cacctaggtg   2160
cttggttgac tacccataca ggctctggca ctaccctgc actgtcaact ttaccatctt    2220
caaggttagg atgtatgtgg ggggcgtgga gcacaggctt gatgctgcat gcaactggac   2280
tcgaggagag cgttgcgact tggaggacag ggatagagca gagctcagcc cgctattgct   2340
gtctacaaca gagtggcaga tactgccctg ttcctacacc acctaccgg ctctgtccac    2400 tggtttaatc cacctccacc agaacatcgt ggacatacaa tacctgtacg gtataggtc    2460 ggcggtcgtc tccattgcca tcaagtggga gtatgtcgtg ctgctcttcc ttctcctggc   2520
ggacgcgcgc gtctgtgcct gcttgtggat gatgctgctg atagcccagg ccgaggctgc   2580
cttagagaac ttggtggtcc tcaatgcggc gtccgtggtc ggagcgcatg gcatgctccc   2640
cttctttatg ttcttctgtg ccgcctggta catgaagggc aggctggtcc ctggagcggc   2700
atacgctttc tacggtgtat ggccgctgct cctgctcctg ctagcattac caccacgagc   2760
ttacgcctat gacgcacctg tgcacggaca gataggcgtg ggtttgttga tattgatcac   2820
cctcttcaca ctcaccccgg ggtataagac cctcctcggc cagtgtctgt ggtggttgtg   2880
ctatctcctg accctggggg aagccatgat tcaggagtgg gtaccaccca tgcaggtgcg   2940
cggcggccgc gatggcatcg cgtgggccgt cactatattc tgcccgggtg tggtgtttga   3000
cattaccaaa tggctttttgg cgttgcttgg gcctgcttac ctcttaaggg ccgctttgac   3060
acatgtgccg tacttcgtca gagctcacgc tctgataagg gtatgcgctt tggtgaagca   3120
gctcgcgggg gtaggtatg ttcaggtggc gctattggcc cttggcaggt ggactggcac    3180
ctacatctat gaccacctca cacctatgtc ggactgggcc gctagcggcc tgcgcgactt   3240
```

```
agcggtcgcc gtggaaccca tcatcttcag tccgatggag aagaaggtca tcgtctgggg    3300
agcggagacg gctgcatgtg gggacattct acatggactt cccgtgtccg cccgactcgg    3360
ccaggagatc ctcctcggcc cagctgatgg ctacacctcc aaggggtgga agctccttgc    3420
tcccatcact gcttatgccc agcaaacacg aggcctcctg ggcgccatag tggtgagtat    3480
gacggggcgt gacaggacag aacaggccgg ggaagtccaa atcctgtcca cagtctctca    3540
gtccttcctc ggaacaacca tctcgggggt tttgtggact gtttaccacg gagctggcaa    3600
caagactcta gccggcttac ggggtccggt cacgcagatg tactcgagtg ctgaggggga    3660
cttggtaggc tggcccagcc ccctgggac caagtctttg gagccgtgca agtgtggagc    3720
cgtcgaccta tatctggtca cgcggaacgc tgatgtcatc ccggctcgga gacgcgggga    3780
caagcgggga gcattgctct ccccgagacc catttcgacc ttgaaggggt cctcgggggg    3840
gccggtgctc tgccctaggg gccacgtcgt tgggctcttc cgagcagctg tgtgctctcg    3900
gggcgtggcc aaatccatcg atttcatccc cgttgagaca ctcgacgttg ttacaaggtc    3960
tcccactttc agtgacaaca gcacgccacc ggctgtgccc cagacctatc aggtcgggta    4020
cttgcatgct ccaactggca gtggaaagag caccaaggtc cctgtcgcgt atgccgccca    4080
ggggtacaaa gtactagtgc ttaacccctc ggtagctgcc accctggggt ttggggcgta    4140
cctatccaag gcacatggca tcaatcccaa cattaggact ggagtcagga ccgtgatgac    4200
cggggaggcc atcacgtact ccacatatgg caaatttctc gccgatgggg gctgcgctag    4260
cggcgcctat gacatcatca tatgcgatga atgccacgct gtggatgcta cctccattct    4320
cggcatcgga acggtccttg atcaagcaga gacagccggg gtcagactaa ctgtgctggc    4380
tacgccacac ccccccgggt cagtgacaac cccccatccc gatatagaag aggtaggcct    4440
cgggcgggag ggtgagatcc ccttctatgg gagggcgatt cccctatcct gcatcaaggg    4500
agggagacac ctgattttct gccactcaaa gaaaaagtgt gacgagctcg cggcggccct    4560
tcggggcatg ggcttgaatg ccgtggcata ctatagaggg ttggacgtct ccataatacc    4620
agctcaggga gatgtggtgg tcgtcgccac cgacgccctc atgacggggt acactgagag    4680
ctttgactcc gtgatcgact gcaatgtagc ggtcacccaa gctgtcgact tcagcctgga    4740
ccccaccttc actataacca cacagactgt cccacaagac gctgtctcac gcagtcagcg    4800
ccgcgggcgc acaggtagag gaagacaggg cacttatagg tatgtttcca ctggtgaacg    4860
agcctcagga atgtttgaca gtgtagtgct ttgtgagtgc tacgacgcag gggctgcgtg    4920
gtacgatctc acaccagcgg agaccaccgt caggcttaga gcgtatttca acacgccgg    4980 cctacccgtg tgtcaagacc atcttgaatt ttgggaggca gttttcaccg gcctcacaca    5040
catagacgcc cacttcctct cccaaacaaa gcaagcgggg gagaacttcg cgtacctagt    5100
agcctaccaa gctacggtgt gcgccagagc caaggccct cccccgtcct gggacgccat    5160
gtggaagtgc ctggccccgac tcaagcctac gcttgcgggc cccacacctc tcctgtaccg    5220
tttgggccct attaccaatg aggtcacct cacacaccct gggacgaagt acatcgccac    5280
atgcatgcaa gctgaccttg aggtcatgac cagcacgtgg gtcctagctg gaggagtcct    5340
ggcagccgtc gccgcatatt gcctggcgac tggatgcgtt tccatcatcg gccgcttgca    5400
cgtcaaccag cgagtcgtcg ttgcgccgga taaggaggtc ctgtatgagg cttttgatga    5460
gatggaggaa tgcgcctcta gggcggctct catcgaagag gggcagcgga tagccgagat    5520
gttgaagtcc aagatccaag gcttgctgca gcaggcctct aagcaggccc aggacataca    5580
acccgctatg caggcttcat ggcccaaagt ggaacaattt tgggcagac acatgtggaa    5640
```

```
cttcattagc ggcatccaat acctcgcagg attgtcaaca ctgccaggga accccgcggt   5700
ggcttccatg atggcattca gtgccgccct caccagtccg ttgtcgacca gtaccaccat   5760
ccttctcaac atcatgggag gctggttagc gtcccagatc gcaccacccg cgggggccac   5820
cggctttgtc gtcagtggcc tggtgggggc tgccgtgggc agcataggcc tgggtaaggt   5880
gctggtggac atcctggcag gatatggtgc gggcatttcg ggggccctcg tcgcattcaa   5940
gatcatgtct ggcgagaagc cctctatgga agatgtcatc aatctactgc ctgggatcct   6000
gtctccggga gccctggtgg tgggggtcat ctgcgcggcc attctgcgcc gccacgtggg   6060 accggggggag ggcgcggtcc aatggatgaa caggcttatt gcctttgctt ccagaggaaa   6120
ccacgtcgcc cctactcact acgtgacgga gtcggatgcg tcgcagcgtg tgacccaact   6180
acttggctct cttactataa ccagcctact cagaagactc cacaattgga taactgagga   6240
ctgccccatc ccatgctccg atcctggct ccgcgacgtg tgggactggg tttgcaccat   6300
cttgacagac ttcaaaaatt ggctgacctc taaattgttc cccaagctgc ccggcctccc   6360
cttcatctct tgtcaaaagg ggtacaaggg tgtgtgggcc ggcactggca tcatgaccac   6420
gcgctgccct tgcggcgcca acatctctgg caatgtccgc ctgggctcta tgaggatcac   6480
agggcctaaa acctgcatga acacctggca ggggaccttt cctatcaatt gctacacgga   6540
gggccagtgc gcgccgaaac ccccacgaa ctacaagacc gccatctgga gggtggcggc   6600
ctcggagtac gcggaggtga cgcagcatgg gtcgtactcc tatgtaacag gactgaccac   6660
tgacaatctg aaaattcctt gccaactacc ttctccagag ttttttctcct gggtggacgg   6720 tgtgcagatc ataggtttg cacccacacc aaagccgttt tccgggatg aggtctcgtt   6780 ctgcgttggg cttaattcct atgctgtcgg gtcccagctt ccctgtgaac ctgagcccga   6840
cgcagacgta ttgaggtcca tgctaacaga tccgccccac atcacggcgg agactgcggc   6900
gcggcgcttg gcacggggat cacctccatc tgaggcgagc tcctcagtga gccagctatc   6960
agcaccgtcg ctgcgggcca cctgcaccac ccacagcaac acctatgacg tggacatggt   7020
cgatgccaac ctgctcatgg agggcggtgt ggctcagaca gagcctgagt ccagggtgcc   7080
cgttctggac tttctcgagc caatggccga ggaagagagc gaccttgagc cctcaatacc   7140
atcggagtgc atgctcccca ggagcgggtt ccacgggcc ttaccggctt gggcacggcc   7200
tgactacaac ccgccgctcg tggaatcgtg gaggaggcca gattaccaac cgcccaccgt   7260
tgctggttgt gctctcccc cccccaagaa ggccccgacg cctcccccaa ggagacgccg   7320
gacagtgggt ctgagcgaga gcaccatatc agaagccctc cagcaactgg ccatcaagac   7380
ctttggccag cccccctcga gcggtgatgc aggctcgtcc acggggggcgg gcgccgccga   7440 atccggcggt ccgacgtccc ctggtgagcc ggccccctca gagacaggtt ccgcctcctc   7500 tatgccccc ctcgaggggg agcctggaga tccggacctg gagtctgatc aggtagagct   7560
tcaacctccc ccccaggggg gggggtagc tcccggttcg ggctcggggt cttggtctac   7620
ttgctccgag gaggacgata ccaccgtgtg ctgctccatg tcatactcct ggaccggggc   7680
tctaataact ccctgtagcc ccgaagagga aaagttgcca atcaaccctt tgagtaactc   7740
gctgttgcga taccataaca aggtgtactg tacaacatca aagagcgcct cacagagggc   7800
taaaaaggta acttttgaca ggacgcaagt gctcgacgcc cattatgact cagtcttaaa   7860
ggacatcaag ctagcggctt ccaaggtcag cgcaaggctc ctcaccttgg aggaggcgtg   7920
ccagttgact ccaccccatt ctgcaagatc caagtatgga ttcggggcca aggaggtccg   7980
cagcttgtcc gggagggccg ttaaccacat caagtccgtg tggaaggacc tcctggaaga   8040
```

```
cccacaaaca ccaattccca caaccatcat ggccaaaaat gaggtgttct gcgtggaccc    8100
cgccaagggg ggtaagaaac cagctcgcct catcgtttac cctgacctcg gcgtccgggt    8160
ctgcgagaaa atggccctct atgacattac acaaaagctt cctcaggcgg taatgggagc    8220
ttcctatggc ttccagtact cccctgccca acggtggag tatctcttga aagcatgggc     8280
ggaaaagaag accccatgg gttttcgta tgatacccga tgcttcgact caaccgtcac      8340
tgagagagac atcaggaccg aggagtccat ataccaggcc tgctccctgc ccgaggaggc    8400
ccgcactgcc atacactcgc tgactgagag actttacgta ggagggccca tgttcaacag    8460
caagggtcaa acctgcggtt acagacgttg ccgcgccagc ggggtgctaa ccactagcat    8520
gggtaacacc atcacatgct atgtgaaagc cctagcggcc tgcaaggctg cggggatagt    8580
tgcgcccaca atgctggtat gcggcgatga cctagtagtc atctcagaaa gccaggggac    8640
tgaggaggac gagcggaacc tgagagcctt cacggaggcc atgaccaggt actctgcccc    8700
tcctggtgat cccccagac cggaatatga cctggagcta ataacatcct gttcctcaaa    8760
tgtgtctgtg gcgttgggcc cgcggggccg ccgcagatac tacctgacca gagacccaac    8820
cactccactc gcccgggctg cctgggaaac agttagacac tcccctatca attcatggct    8880
gggaaacatc atccagtatg ctccaaccat atgggttcgc atggtcctaa tgacacactt    8940
cttctccatt ctcatggtcc aagacaccct ggaccagaac ctcaactttg agatgtatgg    9000
atcagtatac tccgtgaatc ctttggacct tccagccata attgagaggt tacacgggct    9060
tgacgccttt tctatgcaca catactctca ccacgaactg acgcgggtgg cttcagccct    9120
cagaaaactt ggggcgccac ccctcagggt gtggaagagt cgggctcgcg cagtcagggc    9180
gtccctcatc tcccgtggag ggaaagcggc cgtttgcggc cgatatctct tcaattgggc    9240
ggtgaagacc aagctcaaac tcactccatt gccggaggcg cgcctactgg acttatccag    9300
ttggttcacc gtcggcgccg gcggggcgca cttttcac agcgtgtcgc gcgcccgacc     9360
ccgctcatta ctcttcggcc tactccact tttcgtaggg gtaggcctct tcctactccc     9420
cgctcggtag agcggcacac actaggtaca ctccatagct aactgttcct ttttttttt     9480 ttttttttt tttttttttt tttttttttt ttctttttt tttttttccc tctttcttcc     9540
cttctcatct tattctactt tcttccttgg tggctccatc ttagccctag tcacggctag    9600
ctgtgaaagg tccgtgagcc gcatgactgc agagagtgcc gtaactggtc tctctgcaga    9660
tcatgt                                                                9666
```

<210> SEQ ID NO 32
<211> LENGTH: 9666
<212> TYPE: DNA
<213> ORGANISM: Artificial Sequence
<220> FEATURE:
<223> OTHER INFORMATION: Synthetic DNA

<400> SEQUENCE: 32

```
acctgcccct aatagggcg acactccgcc atgaatcact cccctgtgag gaactactgt      60
cttcacgcag aaagcgccta gccatggcgt tagtatgagt gtcgtacagc ctccaggccc    120 cccctcccg ggagagccat agtggtctgc ggaaccggtg agtacaccgg aattgccagg     180
acgaccgggt ccttcttggg atcaaccgc tcaatgcctg gagatttggg cgtgcccccg    240
cgagactgct agccgagtag tgttgggtcg cgaaaggcct tgtggtactg cctgataggg    300
tgcttgcgag tgccccggga ggtctcgtag accgtgcatc atgagcacaa atcctaaacc    360
ccaaagaaaa accaaacgta acaccaaccg tcgcccacag gacgttaagt tcccgggcgg    420
```

| | |
|---|---|
| tggtcagatc gtcggtggag tttacttgtt gccgcgcagg ggcccaggt tgggtgtgcg | 480 |
| tgcgactagg aagacttccg agcggtcgca acctcgtgga aggcgacaac ctatccccaa | 540 |
| ggctcgccgg cccgagggca ggacctgggc tcagcctggg tatccttggc ccctctatgg | 600 |
| caatgagggc ttggggtggg caggatggct cctgtcaccc cgcggctctc ggcctagttg | 660 |
| gggccctaat gaccccggc gtaggtcgcg taatttgggt aaggtcatcg atacccttac | 720 |
| atgcggcttc gccgacctca tggggtacat cccgcttgtc ggcgcccct taggggcgc | 780 |
| tgccagggcc ctggcacatg gtgtccgggt tctggaggac ggcgtgaact atgcaacagg | 840 |
| gaatttgccc ggttgctctt tctctatctt cctcttagct ctgctgtcct gtttgaccat | 900 |
| cccagcttcc gcttatgaag tgcgcaacgt gtccgggata taccatgtca caaacgactg | 960 |
| ctccaactca agcattgtgt atgaggcggc ggacgtgatc atgcatgccc ccgggtgcgt | 1020 |
| gccctgcgtt cgggagaaca attcctcccg ttgctgggta gcgctcactc ccacgctcgc | 1080 |
| ggccaggaat gccagcgtcc ccactacgac attacgacgc cacgtcgact tgctcgttgg | 1140 |
| gacggctgct ttctgctccg ctatgtacgt gggggatctc tgcggatctg ttttcctcat | 1200 |
| ctcccagctg ttcaccttct cgcctcgccg gcatgagaca gtacaggact gcaactgctc | 1260 |
| aatctatccc ggccacgtat caggccatcg tatggcttgg gatatgatga tgaactggtc | 1320 |
| gcccacggca gccttagtgg tgtcgcagtt actccggatc ccacaagctg tcatggacat | 1380 |
| ggtggcgggg gcccactggg gagtcctagc gggccttgcc tactattcca tggtggggaa | 1440 |
| ctgggctaag gttttgattg tgatgctact ctttgccggc gttgacgggc atacccgcgt | 1500 |
| gacgggggg gtgcaaggcc atgtcacctc tacactcacg tccctctta gacctggggc | 1560 |
| gtcccagaaa attcagcttg taaacaccaa tggcagttgg catatcaaca ggactgccct | 1620 |
| gaactgcaat gactccctca aaactgggtt tcttgccgcg ctgttctaca cacacaagtt | 1680 |
| caacgcgtcc ggatgcccgg agcgcatggc cagctgtcgc tccattgaca agttcgacca | 1740 |
| gggatgggt cccatcacct atgctcaacc tgacaactcg gaccagaggc cgtattgctg | 1800 |
| gcactacgca cctcgacagt gtggtatcgt acccgcgtcg caggtgtgcg gtccagtgta | 1860 |
| ttgcttcacc ccaagccctg ttgtagtggg gacgaccgat cgtttcggcg cccctacgta | 1920 |
| taactggggg gacaatgaga cggacgtgct gctcctaaac aacacgcggc cgccgcatgg | 1980 |
| caactggttc ggctgtacat ggatgaatag cactgggttc accaagacgt gcggaggccc | 2040 |
| cccgtgtaac atcagggggg tcggcaacaa caccttgacc tgccccacgg actgcttccg | 2100 |
| gaagcacccc gacgccactt acacaaaatg tggttcgggc ccttggttga cacctaggtg | 2160 |
| cttggttgac tacccataca ggctctggca ctaccctgc actgtcaact ttaccatctt | 2220 |
| caaggttagg atgtatgtgg ggggcgtgga gcacaggctt gatgctgcat gcaactggac | 2280 |
| tcgaggagag cgttgcgact tggaggacag ggatagagca gagctcagcc cgctattgct | 2340 |
| gtctacaaca gagtggcaga tactgccctg ttcctacacc accctaccgg ctctgtccac | 2400 |
| tggtttaatc cacctccacc agaacatcgt ggacatacaa tacctgtacg gtatagggtc | 2460 |
| ggcggtcgtc tccattgcca tcaagtggga gtatgtcgtg ctgctcttcc ttctcctggc | 2520 |
| ggacgcgcgc gtctgtgcct gcttgtggat gatgctgctg atagcccagg ccgaggctgc | 2580 |
| cttagagaac ttggtggtcc tcaatgcggc gtccgtggtc ggagcgcatg gcatgctccc | 2640 |
| cttctttatg ttcttctgtg ccgcctggta catgaagggc aggctggtcc ctggagcggc | 2700 |
| atacgctttc tacggtgtat ggccgctgct cctgctcctg ctagcattac caccacgagc | 2760 |
| ttacgccatg gaccgggaga tggttgcatc ttgcggaggc ggggttttg taggtctagc | 2820 |

```
actcctgacc ttgtcaccat actgtaaagt gttcctcgct aggctcatat ggtggttaca   2880
atattttatc accaaagccg aggcgcattt gcaagtgtcg ctccccccc tcaacgttcg    2940 aggcggacgc gatgccatca tcctcctcat gtgcgcggtc cacccagagc taatctttga   3000
catcaccaaa cttctgctct ccatactcgg tccgctcatg gtgctccaag ctagtttaat   3060
ccgagtgccg tacttcgtgc gcgctcaagg gctcattcgc gcatgcatgt tggtgcggaa   3120
agctgccggg ggccattatg tccaaatggc cttcgtgaag ctagctgcgc tgacaggcac   3180
gtacgtttat gaccacctca ctccactgca ggattgggcc catgtgggcc tacgagacct   3240
tgcggtggca gtagagcccg ttgtctttc tgccatggag accaaggtca tcacctgggg    3300
ggcagacacc gcggcgtgtg gggacattat ctcaggtcta cccgtctccg cccgaagggg   3360
gaaggagata cttttgggac cggccgatag ttttgaaggg caggggtggc gactccttgc   3420
tcccatcact gcttatgccc agcaaacacg aggcctcctg ggcgccatag tggtgagtat   3480
gacggggcgt gacaggacag aacaggccgg gaagtccaa atcctgtcca cagtctctca    3540
gtccttcctc ggaacaacca tctcgggggt tttgtggact gtttaccacg gagctggcaa   3600
caagactcta gccggcttac ggggtccggt cacgcagatg tactcgagtg ctgaggggga   3660
cttggtaggc tggcccagcc ccctgggac caagtctttg gagccgtgca agtgtggagc    3720
cgtcgaccta tatctggtca cgcggaacg tgatgtcatc ccggctcgga gcgcggga     3780 caagcgggga gcattgctct ccccgagacc catttcgacc ttgaagggt cctcgggggg    3840 gccggtgctc tgccctaggg gccacgtcgt tgggctcttc cgagcagctg tgtgctctcg   3900
gggcgtggcc aaatccatcg atttcatccc cgttgagaca ctcgacgttg ttacaaggtc   3960
tcccactttc agtgacaaca gcacgccacc ggctgtgccc cagacctatc aggtcgggta   4020
cttgcatgct ccaactggca gtggaaagag caccaaggtc cctgtcgcgt atgccgccca   4080
ggggtacaaa gtactagtgc ttaacccctc ggtagctgcc accctggggt ttggggcgta   4140
cctatccaag gcacatggca tcaatcccaa cattaggact ggagtcagga ccgtgatgac   4200
cggggaggcc atcacgtact ccacatatgg caaatttctc gccgatgggg ctgcgctag    4260 cggcgcctat gacatcatca tatgcgatga atgccacgct gtggatgcta cctccattct   4320
cggcatcgga acggtccttg atcaagcaga cagccgggg gtcagactaa ctgtgctggc    4380 tacgccaca ccccccgggt cagtgacaac ccccatccc gatatagaag aggtaggcct     4440
cgggcgggag ggtgagatcc ccttctatgg gagggcgatt cccctatcct gcatcaaggg   4500
agggagacac ctgattttct gccactcaaa gaaaagtgt gacgagctcg cggcggccct    4560
tcggggcatg ggcttgaatg ccgtggcata ctatagaggg ttggacgtct ccataatacc   4620
agctcaggga gatgtggtgg tcgtcgccac cgacgccctc atgacggggt acactggaga   4680
ctttgactcc gtgatcgact gcaatgtagc ggtcacccaa gctgtcgact tcagcctgga   4740
ccccaccttc actataacca cacagactgt cccacaagac gctgtctcac gcagtcagcg   4800
ccgcgggcgc acaggtagag aagacaggg cacttatagg tatgtttcca ctggtgaacg    4860
agcctcagga atgtttgaca gtgtagtgct ttgtgagtgc tacgacgcag gggctgcgtg   4920
gtacgatctc acaccagcgg agaccaccgt caggcttaga gcgtatttca acacgcccgg   4980
cctacccgtg tgtcaagacc atcttgaatt ttgggaggca gttttcaccg gcctcacaca   5040
catagacgcc cacttcctct cccaaacaaa gcaagcgggg gagaacttcg cgtacctagt   5100
agcctaccaa gctacggtgt gcgccagagc caaggccct ccccgtcct gggacgccat     5160 gtggaagtgc ctggcccgac tcaagcctac gcttgcgggc cccacacctc tcctgtaccg   5220
```

```
tttgggccct attaccaatg aggtcaccct cacacaccct gggacgaagt acatcgccac    5280
atgcatgcaa gctgaccttg aggtcatgac cagcacgtgg gtcctagctg gaggagtcct    5340
ggcagccgtc gccgcatatt gcctggcgac tggatgcgtt ccatcatcg gccgcttgca     5400 cgtcaaccag cgagtcgtcg ttgcgccgga taaggaggtc ctgtatgagg cttttgatga    5460
gatggaggaa tgcgcctcta gggcggctct catcgaagag gggcagcgga tagccgagat    5520
gttgaagtcc aagatccaag gcttgctgca gcaggcctct aagcaggccc aggacataca    5580
acccgctatg caggcttcat ggcccaaagt ggaacaattt gggccagaca catgtggaa     5640 cttcattagc ggcatccaat acctcgcagg attgtcaaca ctgccaggga accccgcggt    5700
ggcttccatg atggcattca gtgccgccct caccagtccg ttgtcgacca gtaccaccat    5760
ccttctcaac atcatgggag gctggttagc gtcccagatc gcaccacccg cggggccac     5820 cggctttgtc gtcagtggcc tggtgggggc tgccgtgggc agcataggcc tgggtaaggt    5880
gctggtggac atcctggcag atatggtgc gggcatttcg ggggccctcg tcgcattcaa     5940
gatcatgtct ggcgagaagc cctctatgga agatgtcatc aatctactgc ctgggatcct    6000
gtctccggga gccctggtgg tgggggtcat ctgcgcggcc attctgcgcc gccacgtggg    6060
accgggggag ggcgcggtcc aatggatgaa caggcttatt gcctttgctt ccagaggaaa    6120
ccacgtcgcc cctactcact acgtgacgga gtcggatgcg tcgcagcgtg tgacccaact    6180
acttggctct cttactataa ccagcctact cagaagactc cacaattgga taactgagga    6240
ctgccccatc ccatgctccg gatcctggct ccgcgacgtg tgggactggg tttgcaccat    6300
cttgacagac ttcaaaaatt ggctgacctc taaattgttc cccaagctgc ccggcctccc    6360
cttcatctct tgtcaaaagg ggtacaaggg tgtgtgggcc ggcactggca tcatgaccac    6420
gcgctgccct tgcggcgcca acatctctgg caatgtccgc ctgggctcta tgaggatcac    6480
agggcctaaa acctgcatga acacctggca ggggaccttt cctatcaatt gctacacgga    6540
gggccagtgc gcgccgaaac cccccacgaa ctacaagacc gccatctgga gggtggcggc    6600
ctcggagtac gcggaggtga cgcagcatgg gtcgtactcc tatgtaacag gactgaccac    6660
tgacaatctg aaaattcctt gccaactacc ttctccagag ttttttctcct gggtggacgg    6720 tgtgcagatc cataggtttg cacccacacc aaagccgttt ttccgggatg aggtctcgtt    6780
ctgcgttggg cttaattcct atgctgtcgg gtcccagctt ccctgtgaac ctgagcccga    6840
cgcagacgta ttgaggtcca tgctaacaga tccgcccac atcacggcgg agactgcggc    6900
gcggcgcttg gcacggggat cacctccatc tgaggcgagc tcctcagtga gccagctatc    6960
agcaccgtcg ctgcgggcca cctgcaccac ccacagcaac acctatgacg tggacatggt    7020
cgatgccaac ctgctcatgg agggcggtgt ggctcagaca gagcctgagt ccagggtgcc    7080
cgttctggac tttctcgagc caatggccga ggaagagagc gaccttgagc cctcaatacc    7140
atcggagtgc atgctcccca ggagcgggtt tccacgggcc ttaccggctt gggcacggcc    7200
tgactacaac ccgccgctcg tggaatcgtg gaggaggcca gattaccaac cgcccaccgt    7260
tgctggttgt gctctccccc ccccaagaa ggccccgacg cctcccccaa ggagacgccg     7320
gacagtgggt ctgagcgaga gcaccatatc agaagccctc cagcaactgg ccatcaagac    7380
ctttggccag ccccctcga gcggtgatgc aggctcgtcc acggggcgg gcgccgccga     7440 atccggcggt ccgacgtccc ctggtgagcc ggccccctca gagacaggtt ccgcctcctc    7500
tatgcccccc ctcgaggggg agcctggaga tccggacctg gagtctgatc aggtagagct    7560
tcaacctccc ccccaggggg gggggtagc tcccggttcg ggctcgggt cttggtctac      7620
```

```
ttgctccgag gaggacgata ccaccgtgtg ctgctccatg tcatactcct ggaccggggc   7680
tctaataact ccctgtagcc ccgaagagga aaagttgcca atcaacccctt tgagtaactc   7740 gctgttgcga taccataaca aggtgtactg tacaacatca aagagcgcct cacagagggc   7800
taaaaaggta acttttgaca ggacgcaagt gctcgacgcc cattatgact cagtcttaaa   7860
ggacatcaag ctagcggctt ccaaggtcag cgcaaggctc ctcaccttgg aggaggcgtg   7920
ccagttgact ccaccccatt ctgcaagatc aagtatgga ttcggggcca aggaggtccg    7980
cagcttgtcc gggagggccg ttaaccacat caagtccgtg tggaaggacc tcctggaaga   8040
cccacaaaca ccaattccca caaccatcat ggccaaaaat gaggtgttct gcgtggaccc   8100
cgccaagggg ggtaagaaac cagctcgcct catcgtttac cctgacctcg cgtccgggt    8160 ctgcgagaaa atggccctct atgacattac acaaaagctt cctcaggcgg taatgggagc   8220
ttcctatggc ttccagtact cccctgccca acgggtggag tatctcttga agcatgggc    8280 ggaaaagaag gacccccatgg gttttcgta tgatacccga tgcttcgact caaccgtcac   8340
tgagagagac atcaggaccg aggagtccat ataccaggcc tgctccctgc ccgaggaggc   8400
ccgcactgcc atacactcgc tgactgagag actttacgta ggagggccca tgttcaacag   8460
caagggtcaa acctgcggtt acagacgttg ccgcgccagc ggggtgctaa ccactagcat   8520
gggtaacacc atcacatgct atgtgaaagc cctagcggcc tgcaaggctg cggggatagt   8580
tgcgcccaca atgctggtat gcggcgatga cctagtagtc atctcagaaa gccaggggac   8640
tgaggaggac gagcggaacc tgagagcctt cacggaggcc atgaccaggt actctgcccc   8700
tcctggtgat cccccccagac cggaatatga cctggagcta ataacatcct gttcctcaaa   8760
tgtgtctgtg gcgttgggcc cgcggggccg ccgcagatac tacctgacca gagacccaac   8820
cactccactc gcccgggctg cctgggaaac agttagacac tcccctatca attcatggct   8880
gggaaacatc atccagtatg ctccaaccat atgggttcgc atggtcctaa tgacacactt   8940
cttctccatt ctcatggtcc aagacacct ggaccagaac ctcaactttg agatgtatgg   9000
atcagtatac tccgtgaatc ctttggacct tccagccata attgagaggt tacacgggct   9060
tgacgccttt tctatgcaca catactctca ccacgaactg acgcgggtgg cttcagccct   9120
cagaaaactt ggggcgccac ccctcagggt gtggaagagt cgggctcgcg cagtcagggc   9180
gtccctcatc tcccgtggag ggaaagcggc cgtttgcggc cgatatctct tcaattgggc   9240
ggtgaagacc aagctcaaac tcactccatt gccggaggcg cgcctactgg acttatccag   9300
ttggttcacc gtcggcgccg gcggggggcga cattttcac agcgtgtcgc gcgcccgacc   9360
ccgctcatta ctcttcggcc tactcctact tttcgtaggg gtaggcctct tcctactccc   9420
cgctcggtag agcggcacac actaggtaca ctccatagct aactgttcct tttttttttt   9480
tttttttttt tttttttttt tttttttttt ttctttttttt tttttttccc tctttcttcc   9540
cttctcatct tattctactt tctttttcttgg tggctccatc ttagccctag tcacggctag   9600
ctgtgaaagg tccgtgagcc gcatgactgc agagagtgcc gtaactggtc tctctgcaga   9660
tcatgt                                                               9666
```

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)

<223> OTHER INFORMATION: n is A, G, C or T

<400> SEQUENCE: 33
cgtctcntat tacctgcc                    18

<210> SEQ ID NO 34
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: n is A, G, C or T

<400> SEQUENCE: 34
gatcatgtcc cngagacg                    18

<210> SEQ ID NO 35
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: n is a, c, g, or t

<400> SEQUENCE: 35
ggcaggtaat angagacg                    18

<210> SEQ ID NO 36
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t

<400> SEQUENCE: 36
cgtctcnggg acatgatc                    18

<210> SEQ ID NO 37
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 37
gggttattgg agacggtacc gtctcctccc ccc                    33

<210> SEQ ID NO 38
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 38 gggggggagga gacggtaccg tctccaataa ccc                    33

<210> SEQ ID NO 39

```
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 39
tattacctgc c                                                               11

<210> SEQ ID NO 40
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 40
gggacatgat c                                                               11

<210> SEQ ID NO 41
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 41
gggttattac ctgcc                                                           15

<210> SEQ ID NO 42
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 42
gatcatgtcc cccc                                                            14

<210> SEQ ID NO 43
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 43
ggcaggtaat aaccc                                                           15

<210> SEQ ID NO 44
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 44 gggggacat gatc                                                             14

<210> SEQ ID NO 45
<211> LENGTH: 32
<212> TYPE: DNA
<213> ORGANISM: Artificial Sequence
<220> FEATURE:
<223> OTHER INFORMATION: Synthetic oligonucleotide
```

-continued

<400> SEQUENCE: 45
tgctggcttt gatgaaaacc tgcccctaat ag 32

HIGH PRODUCTION SYSTEM FOR INFECTIOUS HEPATITIS C VIRUS PARTICLE

TECHNICAL FIELD

The present invention relates to a high production method for infectious human hepatitis C virus particles.

BACKGROUND ART

Human hepatitis C virus (HCV) is a single-stranded RNA virus that causes chronic hepatitis through persistent infection. Currently, the main cause of chronic hepatitis observed worldwide is persistent HCV infection. In fact, around 50% of individuals with persistent infection develop chronic hepatitis. Chronic hepatitis in approximately 20% of these patients shifts to liver cirrhosis over the course of 10 to 20 years, and some of these patients further go on to advanced lethal pathological conditions such as hepatic cancer.

The main reasons that studies on the development of therapies for such serious diseases are hindered are the lack of efficient cellular culture systems for HCV proliferation, the lack of appropriate small animal models susceptible to HCV infection, viral replication at low levels, and genetic heterogeneity in viral genomes.

Thus, it has been expected that the development of HCV genome replication systems in cell culture systems would contribute to the understanding of viral replication and virus-cell interaction and the provision of systems for evaluation of therapeutic drugs for HCV-induced diseases.

Recently, HCV subgenomic RNA replicons have been produced as HCV-derived autonomously replicable RNAs (Patent Documents 1 and 2 and Non-Patent Documents 1-3). Thus, it becomes possible to analyze the HCV replication mechanism with the use of culture cells. Such HCV subgenomic RNA replicons are obtained by substituting structural proteins located downstream of HCV IRES in the 5' untranslated region of HCV genomic RNA with a neomycin-resistant gene and EMCV-IRES ligated downstream thereof. By introducing such RNA replicon into a Huh7 human liver cancer cell and culturing the cell in the presence of neomycin, it was demonstrated that the RNA replicon replicates autonomously in Huh7 cells. However, only viral RNA replication, among the propagation and replication processes of HCV virus, can be evaluated in this experimental system, and thus virus particles are not produced therein. Thus, the processes of the formation of HCV virus particles in infected cells, the extracellular release of HCV particles, and infection of another cell therewith cannot be analyzed in the system.

In order to solve the above problem, a method for producing virus particles in a culture cell system has been reported. The system utilizes cDNA of HCV entire genomic RNA without the use of an RNA replicon.

Lim et al. attempted to produce HCV virus particles by treating with tetracycline a cell line obtained by introducing an expression vector in which cDNA of genomic RNA of the HCV-S1 strain (genotype 1b) is ligated downstream of a tetracycline response promoter into a Huh7 cell. They confirmed the presence of HCV particles at 1 to $6 \times 10^5$ copies/ml in the culture supernatant. However, they reported that such HCV particles have low infectivity (Non-Patent Document 4).

However, when HCV cDNA is expressed under the control of an RNA polymerase II-type promoter such as CMV, a CAP structure and a polyA strand are added to the 5' end and the 3' end of transcribed RNA, respectively. Accordingly, such RNA is used as a template for protein synthesis in a ribosome, so that replication of transcribed RNA does not take place, which is problematic.

In order to solve the above problem, Heller et al. prepared a construct that can cause intracellular synthesis of HCV RNA to which a cap and polyA are not added, by ligating a ribozyme sequence to the 5' end and the 3' end of the HCV genome such that it is intracellularly transcribed with RNA polymerase II and after that the transcript is cleaved with the ribozyme to produce such HCV RNA (Non-Patent Document 5). Such method for avoiding an addition of a cap at the 5' end by means of a ribozyme is used in a method for intracellular synthesis of hairpin-type RNA (Non-Patent Document 6). In practice, it has been shown that HCV particles are produced at $1 \times 10^7$ copies/ml when an expression vector having an HCV construct sandwiched by two ribozymes is expressed in Huh7. Note that it has not been examined whether or not such particles exhibit infectivity.

Further, it has been recently shown that HCV particles having the ability to infect cells can be produced from HCV entire genomic RNA in a cell culture system (Patent Document 3 and Non-Patent Documents 7 and 8). In such system, the HCV particle production amount is approximately $1 \times 10^7$ copies/ml. Furthermore, it has been shown that it is possible to produce HCV particles having the ability to infect cells in a cell culture system with the use of chimeric viral RNA in which the non-structural protein region of the HCV con1 strain (genotype 1b) has been substituted with the gene of a viral strain (genotype 2a) (Non-Patent Document 9). No specific value for the HCV particle production amount with the use of such system has been disclosed.

Based on the above results, it has become possible to produce an experimental system that allows evaluation of the process involving the formation of HCV virus particles in infected cells, the extracellular release of HCV particles, and infection of another cell therewith.

However, the productivity of the system established by Lim et al. is low. Also, the infectivity possible with the system established by Heller et al. is unclear. Thus, it is considered that mutation might occur upon RNA replication in a system using HCV entire genomic RNA. It has been known that replication might not take place when mutation occurs in the HCV genome. In fact, it has been shown that such replication does not take place when a mutation of the GDD amino acid sequence in the NS5B protein, an HCV non-structural protein, to GND occurs. Meanwhile, the HCV particle production amount is approximately $1 \times 10^7$ copies/ml in both cases. Thus, further increase of the production amount has been expected.

Regarding a method for increasing HCV virus particle production amount, the production of a cell that produce a replicon at a high level has been examined. In this case, the human liver-derived Huh7 cell was used for HCV virus replication, and some cells derived from the strain were cloned. Among them, cells referred to as Huh7.5 were found to replicate approximately 3 times as many HCV RNA replicons as the parent strain (Non-Patent Document 10).

Under the above circumstances, it is thought to be important to develop a high production system for infectious HCV particles with the use of cDNA of HCV entire genomic RNA.

As a virus particle production system using cDNA corresponding to genomic RNA of an RNA virus, a system using an RNA polymerase I promoter/terminator, which is used for production of influenza virus (minus-strand RNA virus) in an animal cell system, has also been known (Non-Patent Document 11). However, it cannot be said that such influenza virus particle production system using an RNA polymerase I promoter/terminator is superior to conventional influenza virus particle production systems in terms of production amount. In addition, Non-Patent Document 11 neither describes nor suggests an HCV production system wherein HCV is a plus strand RNA virus.

Patent Document 1: JP Patent Publication (Kokai) No. 2001-17187 A
Patent Document 2: WO2004/104198A1
Patent Document 3: WO05080575A1
Non-Patent Document 1: Blight et al., Science, 290(2000) pp. 1972-74
Non-Patent Document 2: Friebe et al., J. Virol., 75(2001) pp. 12047-57
Non-Patent Document 3: Kato, T. et al., Gastroenterology, 125(2003) pp. 1808-17
Non-Patent Document 4: Lim S P. et al., Virology, 303(2002) pp. 79-99.
Non-Patent Document 5: Heller, T. et al. Proc. Natl. Acad. Sci. USA., 102 (2005) pp. 2579-83
Non-Patent Document 6: Shinagawa, T. & Ishii, S., Genes Dev., 17(2003) pp. 1340-45
Non-Patent Document 7: Wakita et al. Nature Med. 11 (2005) pp. 791-96
Non-Patent Document 8: Lindenbach B D. et al., Science. 309 (2005) pp. 623-26
Non-Patent Document 9: Pietschmann T. et al., 11th International Symposium on Hepatitis C Virus and Related Viruses, (2004)
Non-Patent Document 10: Blight, K J. et al., J. Virol., 76 (2002) pp. 13001-14
Non-Patent Document 11: Neumann, G. et al., Virology, 202 (1994) pp. 477-479

DISCLOSURE OF THE INVENTION

Problem to be Solved by the Invention

It is an objective of the present invention to provide a method for high production of infectious hepatitis C virus particles from recombinant DNA in a culture cell system.

Means for Solving Problem

In order to establish a method for intracellularly synthesizing HCV genomic RNA having replication ability from HCV genomic cDNA, the present inventors examined HCV genomes having different genotypes and a promoter/terminator that is used for expressing the HCV genomes, and thus have found a novel combination that causes HCV genomic RNA replication. In addition, they cultured cells that synthesize such HCV genomic RNA and thereby confirmed production of infectious HCV particles at a higher level than those reported in the past. This has led to the completion of the present invention.

That is, the present invention relates to the following (a) to (c):

(a) a method for producing infectious hepatitis C virus (HCV) particles, comprising a step of introducing an expression vector into a cell that allows HCV proliferation, such expression vector comprising: JFH1 strain-derived HCV genomic cDNA downstream of a promoter recognized by a ribosomal RNA gene-derived RNA polymerase I; and DNA comprising a terminator recognized by a ribosomal RNA gene-derived RNA polymerase I, further downstream thereof;

(b) a method for producing infectious HCV particles according to (a), wherein the cell that allows HCV proliferation is selected from the group consisting of Huh7, RCYM1RC, 5-15RC, HepG2, and cells of cell lines derived therefrom; and (c) an expression vector for producing infectious hepatitis C virus (HCV) particles, comprising: JFH1 strain-derived HCV genomic cDNA downstream of a promoter recognized by a ribosomal RNA gene-derived RNA polymerase I; and DNA comprising a terminator recognized by a ribosomal RNA gene-derived RNA polymerase I, further downstream thereof.

Further, the present invention relates to a method for producing infectious hepatitis C virus (HCV) particles, comprising the step of introducing an expression vector into a cell that allows HCV proliferation, such expression vector comprising: DNA sequences encoding the 5' untranslated region, structural proteins, and optionally non-structural proteins of HCV and DNA sequences encoding non-structural proteins and the 3' untranslated region derived from the HCV JFH1 strain, downstream of an RNA polymerase I promoter; and DNA comprising an RNA polymerase I terminator further downstream thereof.

More specifically, the present invention relates to the following methods of (1) to (4).

(1) A method for producing infectious hepatitis C virus (HCV) particles, comprising the step of introducing the following expression vector i) or ii) into a cell that is selected from the group consisting of Huh7, RCYM1RC, 5-15RC, HepG2, and cells of cell lines derived therefrom:

i) an expression vector comprising: DNA sequences encoding the 5' untranslated region, Core protein, E1 protein, E2 protein, p7 protein, and NS2 protein derived from an HCV strain and DNA sequences encoding NS3, NS4A, NS4B, NS5A, and NS5B proteins and the 3' untranslated region derived from the HCV JFH1 strain, downstream of a polymerase I promoter; and DNA comprising an RNA polymerase I terminator, further downstream thereof; or ii) an expression vector comprising: DNA sequences encoding the 5' untranslated region, Core protein, E1 protein, E2 protein, and p7 protein derived from an HCV strain and DNA sequences encoding NS2, NS3, NS4A, NS4B, NS5A, and NS5B proteins and the 3' untranslated region derived from the HCV JFH1 strain, downstream of an RNA polymerase I promoter; and DNA containing an RNA polymerase I terminator, further downstream thereof.

(2) The method according to (1) above, wherein the HCV strain is a genotype 1 or genotype 2 HCV strain.

(3) The method according to (2) above, wherein the genotype 1 HCV strain is selected from the group consisting of the H77c strain, the 1 strain, the H strain, the HC-J1 strain, the J1 strain, the con1 strain, the TH strain, the J strain, the JT strain, and the BK strain.

(4) The method according to (2) above, wherein the genotype 2 HCV strain is selected from the group consisting of the J6CF strain, the JFH1 strain, the JCH1 strain, and the HC-J8 strain.

Effects of the Invention

According to the method for producing infectious hepatitis C virus particles from recombinant DNA in a culture cell system of the present invention, infectious HCV particles can be highly produced at a density that is approximately 60 times as high as densities obtained by conventional methods.

BRIEF DESCRIPTION OF THE DRAWINGS

The patent or application file contains at least one drawing executed in color. Copies of this patent or patent application publication with color drawing(s) will be provided by the office upon request and payment of the necessary fee.

Figure 2:
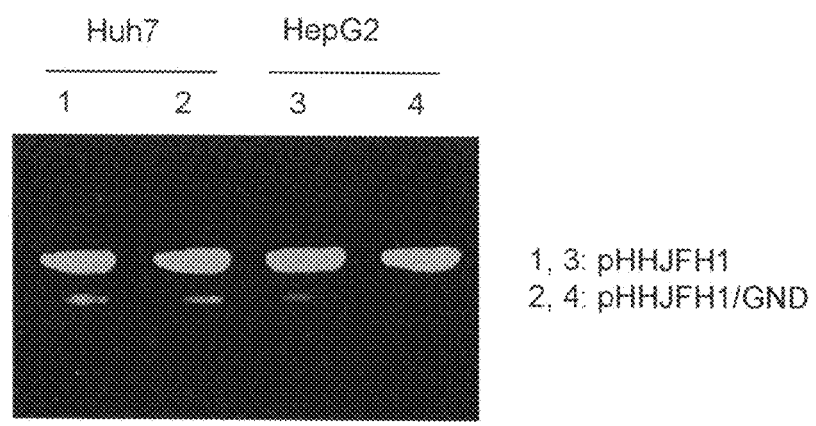

FIG. 2 is an photograph indicating experimental results based on which it was confirmed that HCV RNA was transcribed in a cell into which an HCV expression vector based on an RNA polymerase I promoter/terminator system had been introduced. Lanes 1 and 3 correspond to results for Huh7 and HepG2, into each of which pHH JFH1 was introduced, and lanes 2 and 4 correspond to results for Huh7 and HepG2, into each of which pHH JFH1/GND was introduced.

Figure 3:
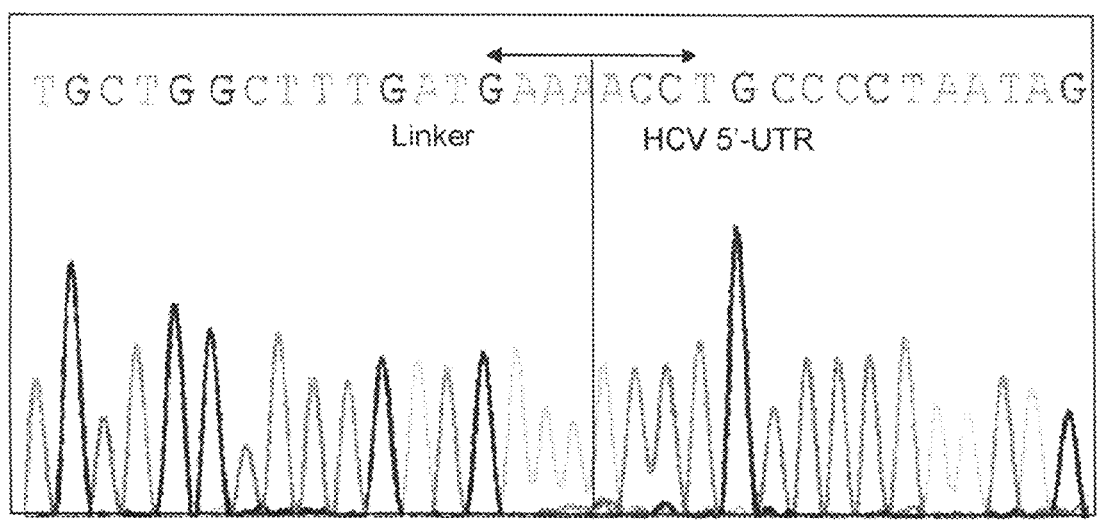

FIG. 3 (SEQ ID NO: 45) shows the 5' end sequence of HCV RNA transcribed from an expression vector based on a polymerase I promoter/terminator system. The 5' end of HCV RNA transcribed in a cell into which PHH JFH1 and pHH JFH1/GND had been introduced was identical to the JFH1 genomic RNA sequence.

Figure 4:
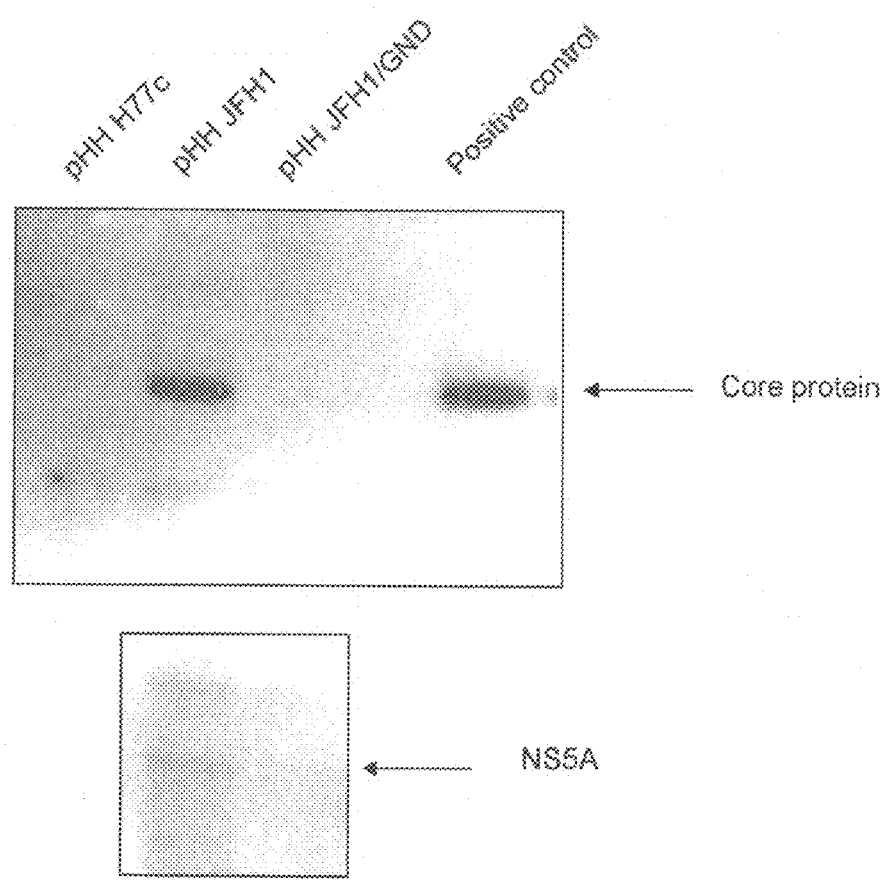

FIG. 4 shows photographs indicating experimental results confirming the presence or absence of translation of an HCV protein in a cell into which an HCV expression vector based on an RNA polymerase I promoter/terminator system had been introduced. It is shown that core protein and the NS5A protein were each translated in a cell into which pHH JFH1 had been introduced. In the case of cells into which pHH H77c and pHH JFH1/GND had been introduced respectively, an HCV protein was not translated.

Figure 5:
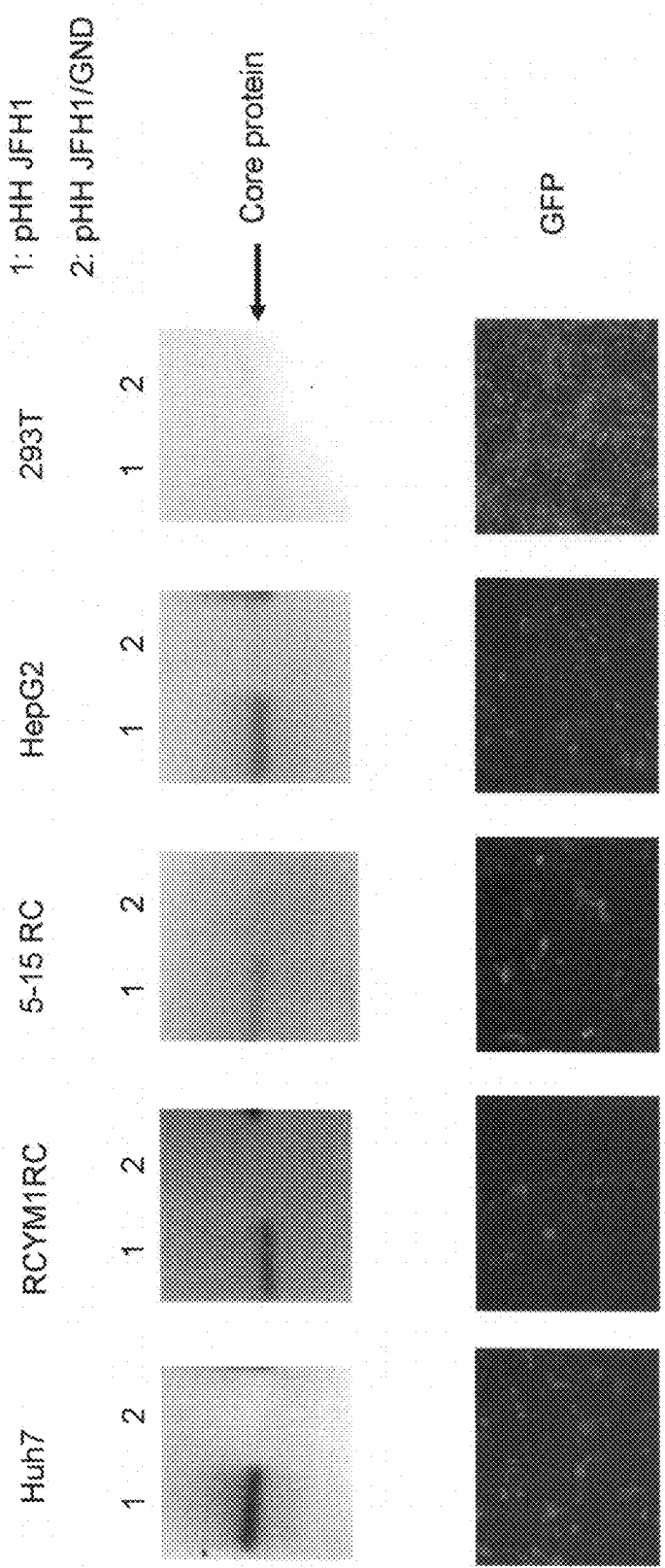

FIG. 5 shows photographs indicating HCV protein expressions and vector transfection efficiencies based on GFP expression in cells of Huh7, RCYM1RC, 5-15RC, HepG2, and 293T cells into which pHH JFH1 and pHH JFH1/GND, respectively, have been introduced together with a GFP expression vector. In the case of pHH JFH1, core protein was expressed therefrom in cells other than 293T. In contrast, in the case of pHH JFH1/GND, core protein was not expressed therefrom in any cells.

Figure 6:
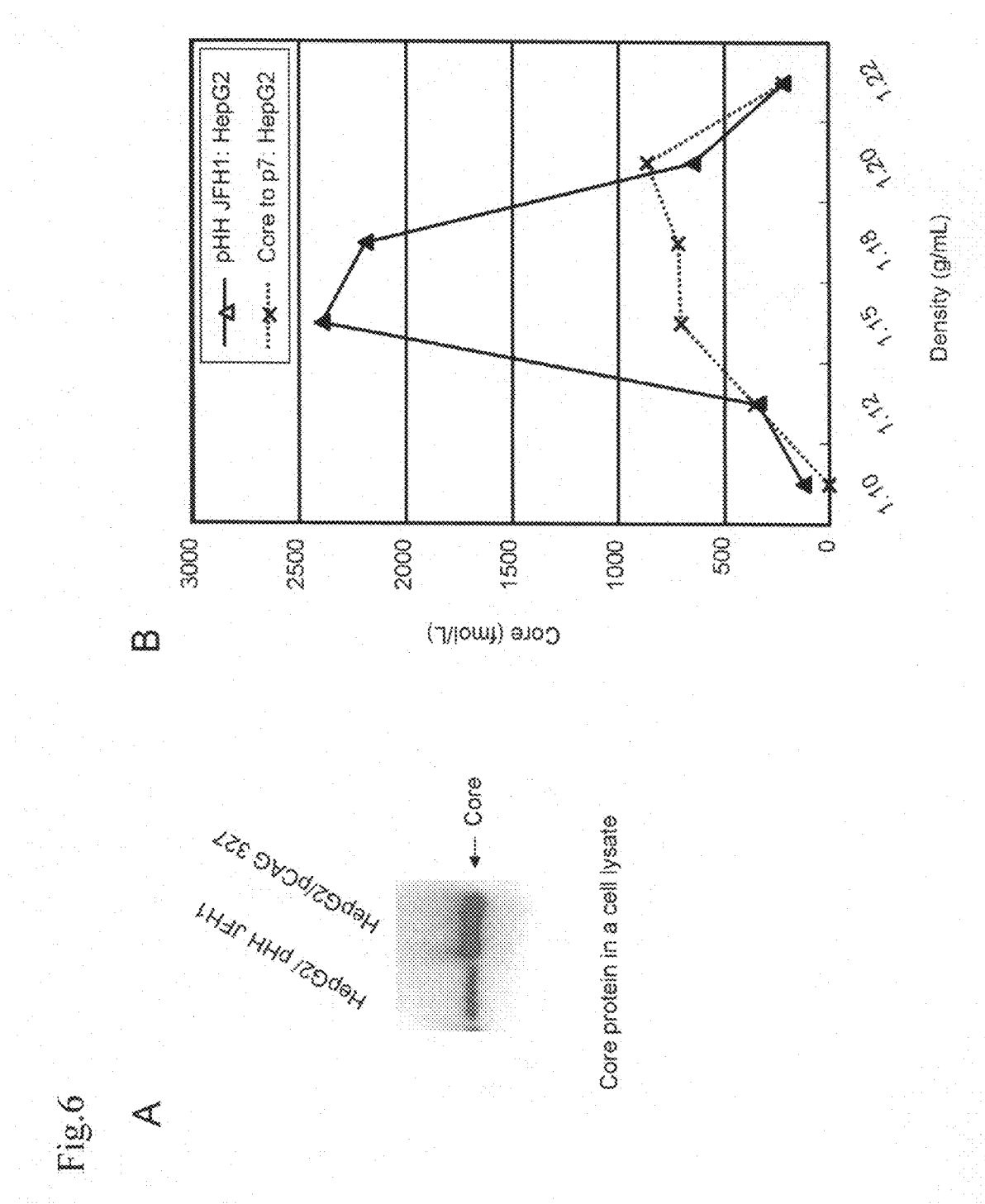

FIG. 6A is a photograph of core protein from a HepG2 cell into which pHH JFH1 has been introduced. FIG. 6B shows the amount of core protein in a sample fractionated by sucrose density centrifugation of a culture solution of HepG2 cells into which pHH JFH1 has been introduced. It is shown that the core protein specific gravity in a pHH JFH1 culture supernatant (Δ in black) was found in the 1.15 g/ml fraction, indicating that the core protein were secreted as an element of virus particles. In contrast, in the case of a culture supernatant of cells in which the core, E1, E2, and p7 were expressed (X), a broad peak was found.

Figure 7:
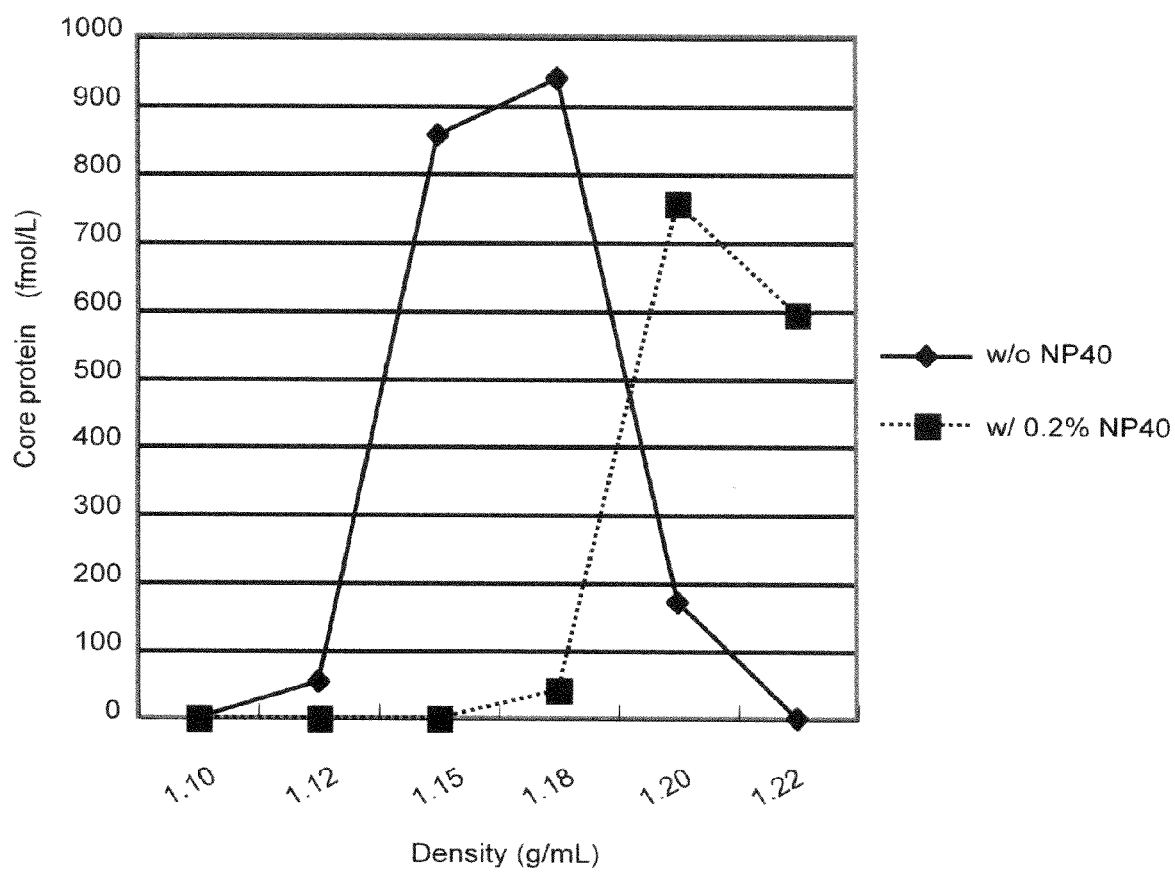

FIG. 7 shows that the core protein peak changes when a culture solution of HepG2 cells into which pHH JFH1 was introduced is treated with NP40, compared with that untreated with NP40. Compared with that untreated with NP40 (♦), in the case of that treated with NP40 (■), the core protein peak shifted to a fraction with a specific gravity of 1.20 g/ml. The results indicate that a surface membrane having a lower specific gravity was detached from each virus particle with NP40 treatment.

Figure 8:
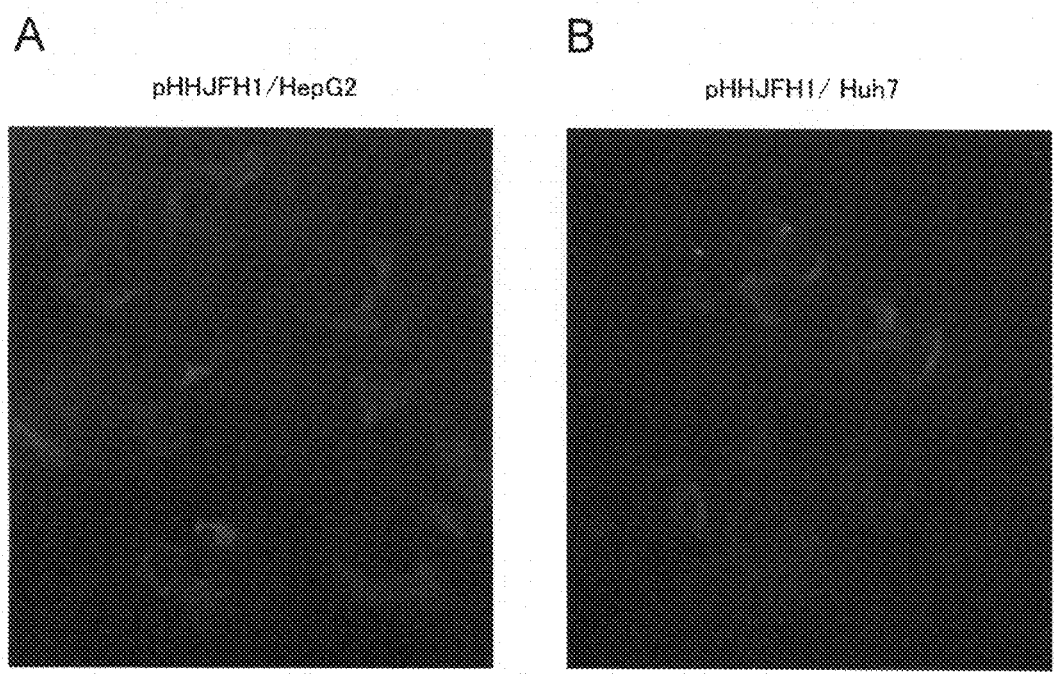

FIG. 8 shows photographs indicating results obtained by inoculating Huh7.5.1 with a culture solution concentrated using ultrafiltration membrane of HepG2 cells (A) or Huh7 cells (B) into which pHH JFH1 had been introduced and staining Huh7.5.1 with an anti-NS5A antibody 4 days later. It is shown that anti-NS5A antibody-positive cells (infected cells) were detected.

Figure 9:
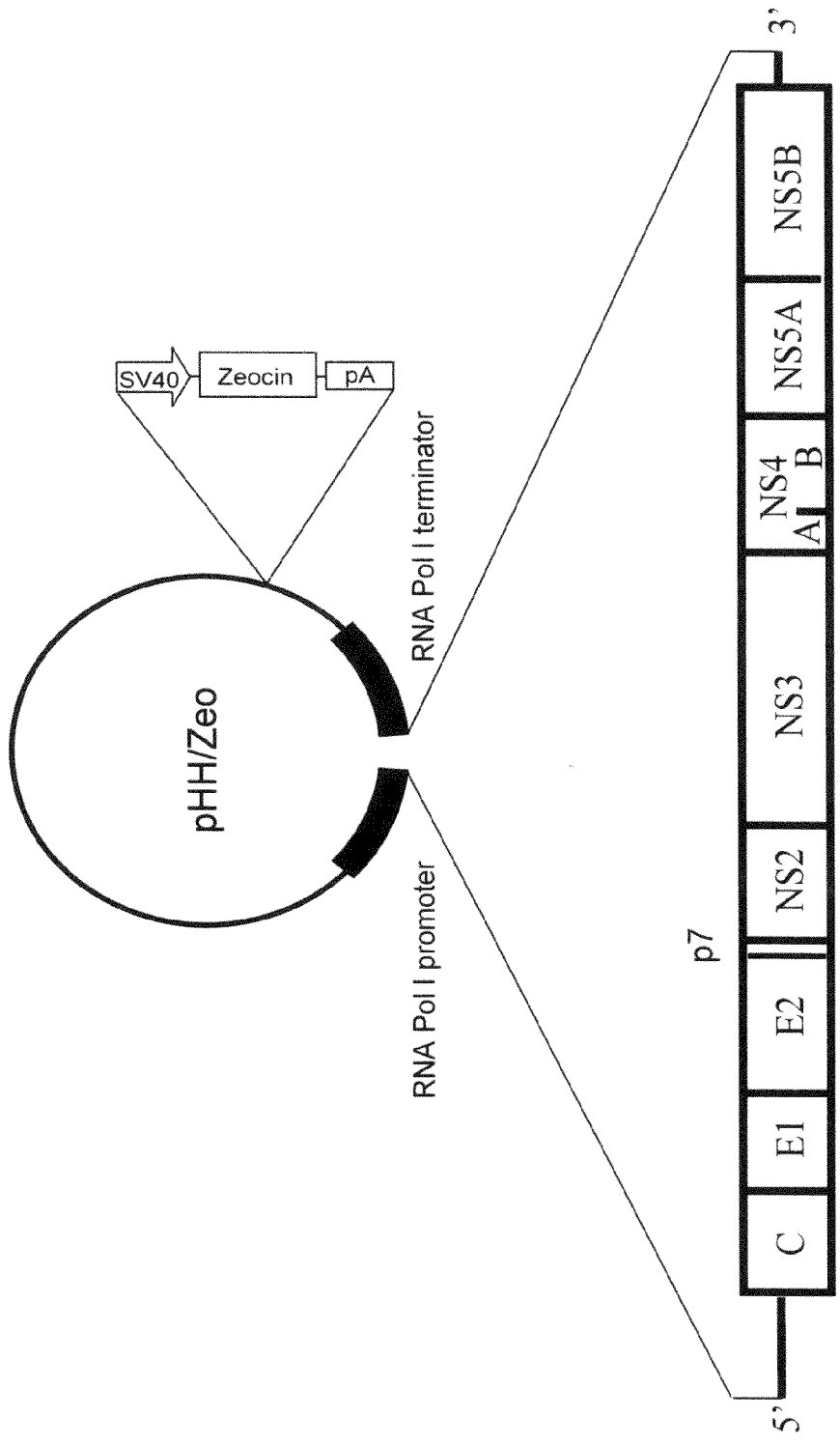

FIG. 9 shows a map of vector in which a cassette that expresses a Zeocin-resistant gene under the control of SV40 promoter has been inserted into pHH JFH1.

FIG. 10 presents SEQ ID NO: 29. FIGS. 10A-10D are views illustrating the DNA sequence of the insert J6(C-p7) JFH1. FIG. 10A shows the most 5' terminal sequence thereof. FIGS. 10B and 10C show the mid-portion of the sequence. FIG. 10D shows the most 3' terminal sequence thereof. Note that the last base of the sequence in FIG. 10A is adjacent to the first base of FIG. 10B, the last base of FIG. 10B is adjacent to the first base of FIG. 10C, and the last base of FIG. 10C is adjacent to the first base of FIG. 10D.

FIG. 11 presents SEQ ID NO: 30. FIGS. 11A-11D are a views illustrating the DNA sequence of the insert H77c(C-p7)JFH1. FIG. 11A shows the most 5' terminal sequence thereof. FIGS. 11B and 11C show the mid-portion of the sequence. FIG. 11D shows the most 3' terminal sequence thereof. Note that the last base of the sequence in FIG. 11A is adjacent to the first base of FIG. 11B, the last base of FIG. 11B is adjacent to the first base of FIG. 11C, and the last base of FIG. 11C is adjacent to the first base of FIG. 11D.

FIG. 12 presents SEQ ID NO: 31 FIGS. 12A-12D are views illustrating the DNA sequence of the insert J1(C-p7) JFH1 and FIG. 12A shows the most 5' terminal sequence thereof. FIGS. 12B and 12C show the mid-portion of the sequence. FIG. 12D shows the most 3' terminal sequence thereof. Note that the last base of the sequence in FIG. 12A is adjacent to the first base of FIG. 12B, the last base of FIG. 12B is adjacent to the first base of FIG. 12C, and the last base of FIG. 12C is adjacent to the first base of FIG. 12D.

FIG. 13 presents SEQ ID NO: 32. FIGS. 13A-13D are views illustrating the DNA sequence of the insert J1(C-NS2) JFH1. FIG. 13A shows the most 5' terminal sequence thereof. FIGS. 13B and 13C show the mid-portion of the sequence. FIG. 13D shows the most 3' terminal sequence thereof. Note that the last base of the sequence in FIG. 13A is adjacent to the first base of FIG. 13B, the last base of FIG. 13B is adjacent to the first base of FIG. 13C, and the last base of FIG. 13C is adjacent to the first base of FIG. 13D.

BEST MODE FOR CARRYING OUT THE INVENTION

1. Construction of an HCV Expression Vectors with the Use of an RNA Polymerase I Promoter/Terminator System There are 3 types of known RNA polymerases that transcribe RNA. RNA polymerase I transcribes rRNA from a ribosomal RNA gene. RNA polymerase II transcribes mRNA from a protein coding gene. RNA polymerase III transcribes tRNA from a tRNA gene.

Each genomic RNA transcribed with RNA polymerases I and III has its own terminator. Transcription is terminated based on the terminator sequence. In contrast, in the case of transcription caused by RNA polymerase II, no terminator sequence is required. The mechanism of the transcription termination is unknown. However, it is considered that what is important for the formation of the 3' end of mRNA is not transcription termination itself but a cleavage reaction of a primary transcription product.

Unlike the cases of a transcription product of a gene located downstream of an RNA polymerase II promoter, cap and polyA are not added to the 5' and 3' ends of each transcription product of genes ligated downstream of RNA polymerase I and III promoters. Natural-occurring HCV genomic RNA does not have cap and polyA added to the 5' and 3' ends thereof. Thus, it is expected that RNA identical to HCV viral genomic RNA can be transcribed by expressing HCV genomic DNA with an RNA polymerase I or III promoter.

As an available promoter, any promoter that does not cause the addition of cap and polyA to the 5' and 3' ends, respectively, of transcribed RNA is appropriate. Such promoter may be preferably an RNA polymerase I promoter and more preferably an rRNA gene-derived promoter. In addition, such promoter is derived from an animal, preferably from mouse or human. A particularly preferable RNA polymerase I promoter is a human ribosomal RNA (rRNA) gene promoter.

Further, as a terminator sequence, an RNA polymerase I terminator is appropriate, and it is preferably an rRNA gene-derived terminator Such terminator is derived from an animal, preferably from mouse or human. A particularly preferred RNA polymerase I terminator is a mouse ribosomal RNA (rRNA) gene terminator.

An RNA polymerase I promoter/terminator system is used for reconstruction of influenza virus particles (Neumann, G. et al., Virology, 202(1994) pp. 477-479, Neumann, G. & Kawaoka, Y., Virology 287 (2001) pp. 243-250, JP Patent Publication (Kohyo) No. 2003-520573 A). In the method of the present invention, pHH21, an RNA polymerase I promoter/terminator system-based vector (Neumann G. et al., Proc. Natl. Acad. Sci. USA, 96 (1999) pp. 9345-9350), can be used. pHH21 is an expression vector that contains a human RNA polymerase I promoter as a promoter and a mouse RNA polymerase I terminator as a terminator.

A promoter/terminator and HCV genomic cDNA can be ligated without the addition of an excessive nucleotide sequence therebetween by adding a restriction enzyme BsmBI recognition sequence to the 5' and 3' ends of HCV genomic cDNA by PCR, digesting it with BsmBI, and inserting the HCV genome into the BsmBI site of pHH21.

In addition, an expression vector used for the method of the present invention can be newly constructed by adequately ligating the above-mentioned promoter, HCV genomic cDNA, and the terminator.

According to phylogenetic analysis with nucleotide sequences of HCV strains, HCVs are classified into the following 6 types: genotype 1a, genotype 1b, genotype 2a, genotype 2b, genotype 3a, and genotype 3b. Each genotype is further classified into some subtypes. In addition, the full-length genomic sequences of some HCV genotypes have been determined (Simmonds, P. et al., Hepatology, 10 (1994) pp. 1321-1324; Choo, Q. L et al., Science, 244 (1989) pp. 359-362; Okamoto, H et al., J. Gen. Virol., 73(1992) pp. 673-679; Mori, S. et al., and Biochem. Biophis. Res. Commun. 183 (1992) pp. 334-342).

In the present invention, specifically, an HCV strain that can be used includes: genotype 1 (including genotypes 1a and 1b) such as H77c (H77 strain consensus sequence: GenBank accession no. AF011751), the 1 strain (GenBank accession no. M62321), the H strain (GenBank accession no. M67463), the HC-J1 strain (GenBank accession no. D10749), the J1 strain (GenBank accession no. D89815), the con1 strain (GenBank accession no. AJ238799), the TH strain (Wakita, T. et al., J. Biol. Chem., (1994) 269, pp. 14205-14210), the J strain (GenBank accession no. D90208), the JT strain (GenBank accession no. D01171), and the BK strain (GenBank accession no. M58335); genotype 2 (including genotypes 2a and 2b) such as the J6CF strain (GenBank accession no. AF177036), the JFH1 strain (also referred to as the JFH-1 strain: GenBank accession no. AB047639), the JCH1 strain (GenBank accession no. AB047640), and the HC-J8 strain (GenBank accession no. D01221). In addition, a list of GenBank accession numbers of other strains has already been reported and thus they are available (Tokita, T. et al., J. Gen. Virol. (1998) 79, pp. 1847-1857; Cristina J. & Colina R. Virolgy Journal, (2006) 3, pp. 1-8).

HCV genomic RNA-derived cDNA of any of the above genotypes can be used for insertion into an RNA polymerase I promoter/terminator-based vector. Further, chimeric cDNA derived from those of any genotypes can also be used. Preferably, cDNA that is derived from a genotype of which HCV genomic RNA can be autonomously replicated when it is introduced into an HCV permissive cell such as Huh7 can be used (Wakita, T., et al. Nat. Med., 11, (2005) pp. 791-796; Lindenbach B D., et al., Science, 309(2005) pp. 623-626). A further preferred cDNA used herein includes a genomic cDNA sequence (GenBank accession no. AB047639, Kato, T. et al., Gastroenterology, 125 (2003) pp. 1808-1817; SEQ ID NO: 27) corresponding to genome RNA of the JFH1 strain of genotype 2a (JP Patent Publication (Kokai) No. 2002-171978 A).

The genome of hepatitis C virus (HCV) is a single-stranded (+) strand RNA comprising approximately 9600 nucleotides. This genomic RNA comprises the 5' untranslated region (also denoted as 5' NTR or 5' UTR), a translated region composed of a structural region and a non-structural region, and the 3' untranslated region (also denoted as 3' NTR or 3' UTR). HCV structural proteins are encoded in the structural region, and a plurality of non-structural proteins are encoded in the non-structural region.

Such HCV structural proteins (Core, E1, E2, and p7) and non-structural proteins (NS2, NS3, NS4A, NS4B, NS5A, and NS5B) are generated by first translation of the translated region into a single continuous polyprotein and then release of proteins with restricted cleavage of the polyprotein by proteases. Among these structural proteins and non-structural proteins (that is, viral proteins of HCV), "Core" is a core protein, and E1 and E2 are envelope proteins. The non-structural proteins are proteins involved in viral self replication, NS2 is known to have metalloprotease activity, and NS3 is known to have serine protease activity (at one-third of the N terminal side) and helicase activity (at two-thirds of the C-terminal side). Furthermore, it has been reported that NS4A is a cofactor for protease activity of NS3, and NS5B has RNA-dependent RNA polymerase activity.

An expression vector used for the method for producing HCV particles of the present invention should comprise: DNA having a sequence containing the 5' untranslated region, Core protein coding sequence, E1 and E2 protein coding sequences, a p7 protein coding sequence, NS2, NS3, NS4 (including NS4A and NS4B), NS5A, and NS5B protein coding sequences, and the 3' untranslated region of HCV genomic cDNA in such order, downstream of a promoter recognized by an RNA polymerase I (RNA polymerase I promoter); and a terminator recognized by an RNA polymerase I (RNA polymerase I terminator), further downstream thereof. These sequences are generated by first translation of them into a single continuous polyprotein and then release of proteins with restricted cleavage of the polyprotein by proteases. As a result, HCV particles are produced.

In the method for producing HCV particles of the present invention, an expression vector used herein comprises a DNA fragment in which cDNA synthesized from HCV genomic RNA derived from any HCV strain is ligated downstream of an RNA polymerase I promoter, and an RNA polymerase I terminator is further ligated downstream thereof. HCV cDNA that is to be ligated downstream of an RNA polymerase I promoter and upstream of an RNA polymerase I terminator may be genomic cDNA corresponding to genomic RNA derived from a single HCV strain (preferably the JFH1 strain), or a chimeric nucleic acid that is derived from cDNAs synthesized from genomic RNAs derived from two or more HCV strains (preferably at least one of them is the JFH1 strain). Preferably, the HCV cDNA that is to be ligated between an RNA polymerase I promoter and an RNA polymerase I terminator comprises an HCV entire genome-like cDNA sequence containing DNA sequences encoding the 5' untranslated region, structural proteins (Core, E1, E2, and p7), non-structural proteins (NS2, NS3, NS4A, NS4B, NS5A, and NS5B), and the 3' untranslated region of HCV in such order.

In particular, a very preferred one because of its high level of infectious HCV production ability is a chimeric HCV expression vector comprising, downstream of an RNA polymerase I promoter, DNA sequences encoding the 5' untranslated region and structural proteins derived from an HCV strain (preferably of genotype 1 or 2), respectively, optionally DNA sequences encoding HCV strain-derived non-structural proteins, and subsequently DNA sequences encoding HCV JFH1 strain-derived non-structural proteins and the 3' untranslated region in the order; and a DNA fragment comprising an RNA polymerase I terminator, further downstream thereof.

A more preferred expression vector used in the present invention comprises, downstream of an RNA polymerase I promoter, an HCV genomic cDNA sequence consisting of the 5' untranslated region coding sequence, a Core protein coding sequence, E1 and E2 protein coding sequences, a p7 protein coding sequence, and an NS2 protein coding sequence of HCV genomic cDNA (i.e., DNA encoding full-length HCV genomic RNA) derived from any HCV strain; and NS3, NS4A, NS4B, NS5A, and NS5B protein coding sequences and the 3' untranslated region coding sequence of JFH1 strain-derived HCV genomic cDNA; and, further downstream thereof, DNA comprising an RNA polymerase I terminator. In addition, another preferable expression vector comprises: an HCV genomic cDNA sequence comprising, downstream of an RNA polymerase I promoter, the 5' untranslated region, a Core protein coding sequence, E1 and E2 protein coding sequences, and a p7 protein coding sequence of HCV genomic cDNA derived from any HCV strain; and NS2, NS3, NS4A, NS4B, NS5A, and NS5B protein coding sequences and the 3' untranslated region coding sequence of JFH1 strain-derived HCV genomic cDNA; and, further downstream thereof, DNA comprising an RNA polymerase I terminator.

Any HCV strain used in the above expression vector can be preferably HCV strains of genotypes 1 and 2. In addition, preferably, the 5' untranslated region coding sequence in the above expression vector may be a JFH1 strain-derived sequence or a chimeric sequence derived from those of two or more HCV strains selected from genotype 1 and genotype 2 HCV strains. When a chimeric sequence is used, it preferably comprises a JFH1 strain-derived sequence. A genotype-1 HCV strain that can be used herein includes, for example, the H77c strain, the 1 strain, the H strain, the HC-J1 strain, the J1 strain, the con1 strain, the TH strain, the J strain, the JT strain, and the BK strain. A genotype-2 HCV strain that can be used herein includes, for example, the J6CF strain, the JFH1 strain, the JCH1 strain, and the HC-J8 strain. Further preferred HCV strain includes the JFH1 strain, the J6CF strain, the J1 strain, and the H77c strain.

As an example, in JFH1 strain-derived full-length genomic cDNA, a region encoding from the 5' untranslated region to the NS2 protein, which can be incorporated into the expression vector of the present invention, ranges from nucleotide numbers 1 to 3430 of the nucleotide sequence shown in SEQ ID NO: 27 (DNA sequence with GenBank accession no. AB047639); and a region encoding from the NS3 protein to the 3' untranslated region ranges from nucleotide numbers 3431 to 9678 thereof. Similarly, in JFH1 strain-derived full-length genomic cDNA, a region encoding from the 5' untranslated region to the p7 protein ranges from nucleotide numbers 1 to 2779 of the nucleotide sequence shown in SEQ ID NO: 27; and a region encoding from the NS2 protein to the 3' untranslated region ranges from nucleotide numbers 2780 to 9678 thereof. Also, positions of regions on another HCV strain-derived genomic cDNA can be defined based on the above genomic cDNA sequence of the JFH1 strain.

A preferred example of the expression vector according to the present invention is an expression vector comprising any one of DNA fragments J6(C-p7)JFH1 (SEQ ID NO: 29), H77c(C-p7)JFH1 (SEQ ID NO: 30), J1(C-p7)JFH1 (SEQ ID NO: 31), and J1(C-NS2)JFH1 (SEQ ID NO: 32) shown in the Examples as described below. Preferably, these DNA fragments are inserted under the control of an expression promoter in the vector.

It has been demonstrated that autonomous replication does not take place when amino acid sequence GDD is mutated into GND in the HCV non-structural protein NS5B (Kato, T. et al., Gastroenterology, 125(2003) pp. 1808-1817). Thus, as an experimental control, the NS5B protein having the mutated GND-containing amino acid sequence can be used.

2. Confirmation of Intracellular HCV RNA Synthesis

HCV RNA can be transcribed by introducing the expression vector produced as described above of the present invention into cells. It is possible to introduce DNA into cells by a common method, such as electroporation, a lipofection method, or a calcium phosphate method.

HCV RNA transcribed from expression vector DNA can be analyzed by a conventional molecular biological method (Molecular Cloning 3$^{rd}$ Edition Sambrook & Russell Cold Spring Harbor Laboratory Press 2001). Specifically, it is possible to analyze the amount or the sequence of transcribed RNA by the Northern blot method, a ribonuclease protection assay method, the RT-PCR method, the RACE method, or the like. Upon RNA quantification, the Northern blot method, the RT-PCR method, or the like is used. Upon RNA sequence analysis, the RACE method is used.

When the sequence of the 5' end of HCV RNA intracellularly transcribed is analyzed, a synthetic RNA linker having a given sequence is ligated to HCV RNA with an RNA ligase and then the resultant is used as a template for cDNA synthesis with a synthetic DNA primer complementary to HCV RNA and a reverse transcription enzyme. Subsequently, PCR is carried out with a primer of a sequence within the linker and a primer located at the 5' side of the primer used above for amplification of a fragment complementary to HCV RNA. Then the amplification product is cloned into a plasmid vector, followed by nucleotide sequence determination thereof. Accordingly, the sequence of HCV RNA intracellularly transcribed can be analyzed. If a DNA fragment is not amplified in the first PCR, nested-PCR method can be used for performing the sequence analysis.

3. Confirmation of Intracellular HCV Protein Expression

In cells infected with HCV, in which HCV genomic RNA is replicated, the above HCV proteins are expressed. Thus, if HCV proteins are detected in a protein extract from HCV genomic RNA-replicating cells, it can be determined that such cells replicate HCV genomic RNA. Detection of HCV proteins can be carried out in accordance with any known protein detection method. For instance, such detection can be carried out by reacting an antibody against an HCV protein that is expected to be expressed from an introduced HCV genomic RNA with a protein extract from cells. More specifically, for example, such detection can be carried out by blotting a protein sample extracted from cells onto a nitrocellulose membrane, reacting it with an anti-HCV protein antibody (e.g., an anti-NS3-specific antibody or an antiserum collected from a hepatitis C patient), and detecting the anti-HCV protein antibody thereon.

A host cell used for expressing the HCV protein therein may be any cell as long as it can be subcultured. Such a host cell may be preferably a eukaryotic cell, more preferably a human cell, and still more preferably a human liver-derived cell, a human uterine cervix-derived cell, or a human fetal kidney-derived cell. Preferred examples of the cells include proliferative cells such as those of cancer cell lines and stem cell lines. More preferred examples thereof include a Huh7 cell (ATCC CCL-185), a HepG2 cell (ATCC HB 8065), an IMY-N9 cell (Date, T. et al., J. Biol. Chem., (2004) 279, pp. 22371-22376), a HeLa cell (ECACC 93021013), an RCYM1RC cell (Murakami, K., et al., Virology, 351, 381-392, 2006), a 5-15RC cell (Pietschmann T., et al., J Virol. (2001) 75, pp. 1252-1264), and cells of cell lines derived from such cells. Particularly preferred cells include a Huh7 cell, an RCYM1RC cell, a 5-15RC cell, a HepG2 cell, and cells of cell lines derived from such cells. These cells used herein may be commercially available cells, or may be obtained from cell depositories, or may be cells of cell lines established from any cells (e.g., cancer cells or stem cells). Cells of cell lines derived from a Huh7 cell include a Huh7.5 cell (Blight, K J. Et al., J. Virol., (2002) 76, pp. 13001-13014) and a Huh7.5.1 cell (Zhong, J. et al., Proc. Natl. Acad. Sci USA, (2005) 102, pp. 9294-9299). The former is a cell with high HCV replication ability, which is obtained by eliminating a replicon with an interferon treatment from a replicon-replicating cell that has been established through gene introduction of a replicon into a Huh7 cell. The latter is a cell with good replicon replication efficiency, which is obtained by eliminating a replicon with an interferon γ treatment from a replicon-replicating cell generated from a Huh7.5 cell.

4. Confirmation of HCV Particle Production

The hepatitis C virus (HCV) particle comprising HCV genomic RNA transcribed from the expression vector of the present invention can be produced by introducing the expression vector of the present invention into an HCV permissive cell (cell that allows HCV proliferation) and culturing the cell resulting that. Preferred HCV permissive cell used herein includes a Huh7 cell, an RCYM1RC cell, a 5-15RC cell, a HepG2 cell, and cells of cell lines derived from such cells. The thus produced hepatitis C virus (HCV) particle has the ability to infect other cells. The present invention relates to such a method for producing the infectious hepatitis C virus particle.

The virus particle production ability of the cells may be confirmed by any known virus detection method. For instance, the culture solution of cells that are suspected of producing virus particles is fractionated through the sucrose density gradient, and the density of fraction, HCV core protein concentration, and amount of HCV genomic RNA are determined for each fraction. As a result, if the peak of the HCV core protein coincides with that of HCV genomic RNA, and if the density of the fraction in which the peak was detected is smaller than the density of the equivalent fraction as obtained by fractionating the culture supernatant treated with 0.25% NP40 (Polyoxyethylene(9)Octylphenyl Ether), the cells used can be determined to have virus particle production ability. Alternatively, since it has been reported that free HCV particles have specific gravity values of 1.14 to 1.16 g/ml (Kaito, M. et al., J. Gen. Virol. 75 (1994) pp. 1755-1760), it is also possible to compare the above values with the specific gravity.

Alternatively, HCV virus particles released into a culture solution can be detected with an antibody against the Core protein, E1 protein, E2 protein, or the like. In addition, the presence of HCV virus particles can be indirectly detected by amplifying HCV genomic RNA contained in HCV virus particles in a culture solution by the RT-PCR method with specific primers, followed by detection.

5. Infection of Another Cell with HCV Particles of the Present Invention

HCV virus particles produced by the method of the present invention have the ability to infect a cell (preferably an HCV permissive (sensitive) cell). According to the present invention, a method for producing a hepatitis C virus-infected cell comprising culturing a cell into which an HCV expression vector based on an RNA polymerase I promoter/terminator system has been introduced and infecting another cell (preferably an HCV permissive cell) with virus particles in the obtained culture (preferably culture supernatant), is also provided. In the present invention, the HCV permissive cell means a cell having an ability to replicate HCV genomic RNA and/or to be infected with HCV. Such HCV permissive cell is preferably, but is not limited to, a hepatic cell or a lymphoid lineage cell. Specifically, the hepatic cell includes, but is not limited to, a primary hepatocyte, a Huh7 cell, a HepG2 cell, an IMY-N9 cell, a HeLa cell, a 293 cell, and the like. The lymphoid lineage cell includes, but is not limited to, a Molt4 cell, an HPB-Ma cell, a Daudi cell, and the like. Particularly preferred examples of such HCV permissive cell include a Huh7 cell, an RCYM1RC cell, a 5-15RC cell, a HepG2 cell, and cells of cell lines derived (produced) from such cells. Preferred examples of a cell derived from a Huh7 cell include a Huh7.5 cell and a Huh7.5.1 cell.

When a cell (e.g., an HCV permissive cell) is infected with HCV particles generated in a cell into which the HCV expression vector based on an RNA polymerase I promoter/terminator system of the present invention has been introduced, HCV genomic RNA is replicated and virus particles are formed in the infected cell.

HCV virus particles generated in the cell into which the HCV expression vector based on an RNA polymerase I promotor/terminator system of the present invention has been introduced can infect HCV-susceptible animals such as chimpanzees and the like and induce hepatitis caused by HCV therein.

It is possible to determine whether or not HCV particles generated in a cell into which the HCV expression vector based on an RNA polymerase I promotor/terminator system of the present invention has been introduced have infectivity in the following manner. An HCV permissive cell (e.g., Huh7) is treated with a culture supernatant obtained by culturing a cell into which the HCV expression vector comprising an RNA polymerase I promotor/terminator system of the present invention has been introduced. 48 hours later, for instance, the cells are immunostained with an anti-core antibody and then infected cells are counted. Alternatively, a cell extract is subjected to SDS-polyacrylamide gel electrophoresis and then core protein can be detected by Western blotting.

6. Obtaining Infectious HCV Particle-Producing Cell Lines

A cell into which the HCV expression vector based on an RNA polymerase I promotor/terminator system of the present invention has been stably introduced can continuously produce infectious HCV particles. In order to obtain a cell line in which the HCV expression vector based on an RNA polymerase I promoter/terminator system of the present invention is stably expressed, it is preferable to incorporate a drug-resistant gene into the vector. Examples of a drug-resistant gene include a G418-resistant gene, a hygromycin-resistant gene, a puromycin-resistant gene, a Zeocin-resistant gene, and a blasticidin-resistant gene. In addition, it is possible to estimate the HCV particle production ability of a clone selected based on drug resistance by detecting the amount of Core protein in a culture supernatant of such clone or the amount of HCV RNA replicated in such clone by Northern blotting or quantitative RT-PCR.

This description includes the disclosure of the description and/or drawings of Japanese Patent Application No. 2005-287646, to which the present application claims a priority.

All publications, patents, and patent applications cited herein are incorporated herein by reference in their entirety.

Examples

The present invention is hereafter described in greater detail with reference to the following examples. However, the technical scope of the present invention is not limited thereto.

Example 1

Construction of HCV Expression Vectors with the Use of the RNA Polymerase I Promotor/Terminator System cDNA of HCV genomic RNA used were cDNA of JFH1 strain-derived genomic RNA of genotype 2a (GenBank accession no. AB047639, Kato, T. et al., Gastroenterology, 125(2003) pp. 1808-1817), cDNA of JFH1 strain-derived genomic RNA having a DNA sequence modified to cause a GDD amino acid sequence in NS5B of the JFH1 strain to be replaced by a GND amino acid sequence (Wakita, T. et al. Nat. Med., 11 (2005) pp. 791-796), cDNA of J6CF strain-derived genomic RNA (GenBank accession no. AF177036, Yanagi, M. et al. Virology, 262 (1999) pp. 250-263), cDNA of H77c strain-derived genomic RNA of genotype 1a (GenBank accession no. AF011751, Yanagi, M. et al., Proc. Natl. Acad. Sci. USA, 94 (1997) pp. 8738-8743), and cDNA of J1 strain-derived genomic RNA of genotype 1b (GenBank accession no. D89815, Aizaki, H. et al. Hepatology, 27 (1998) pp. 621-627).

Figure 1A:
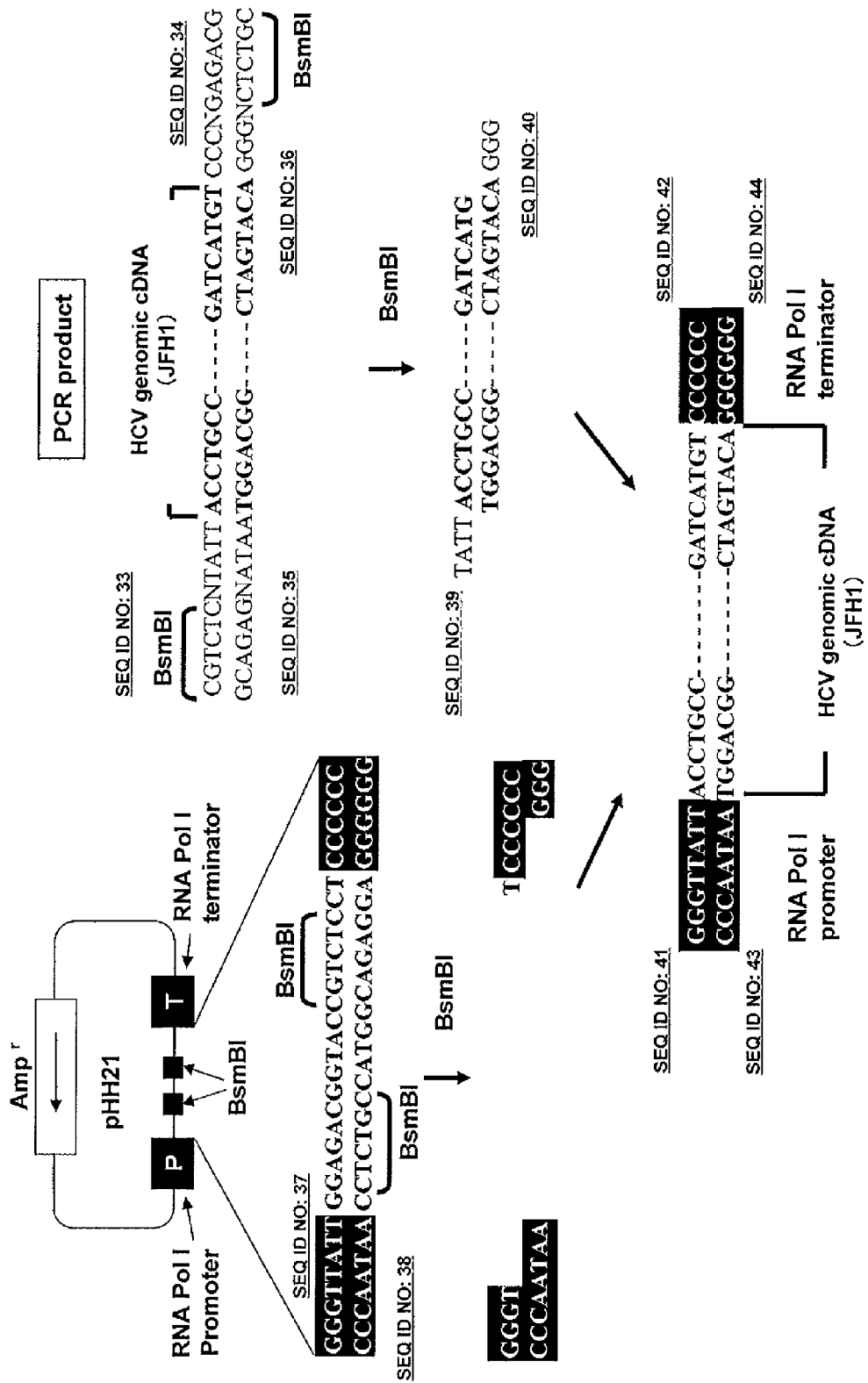
FIG. 1A (SEQ ID NOS: 33-44) shows a diagram of the construction of an HCV expression vector via an RNA polymerase I promoter/terminator system.
Figure 1B:
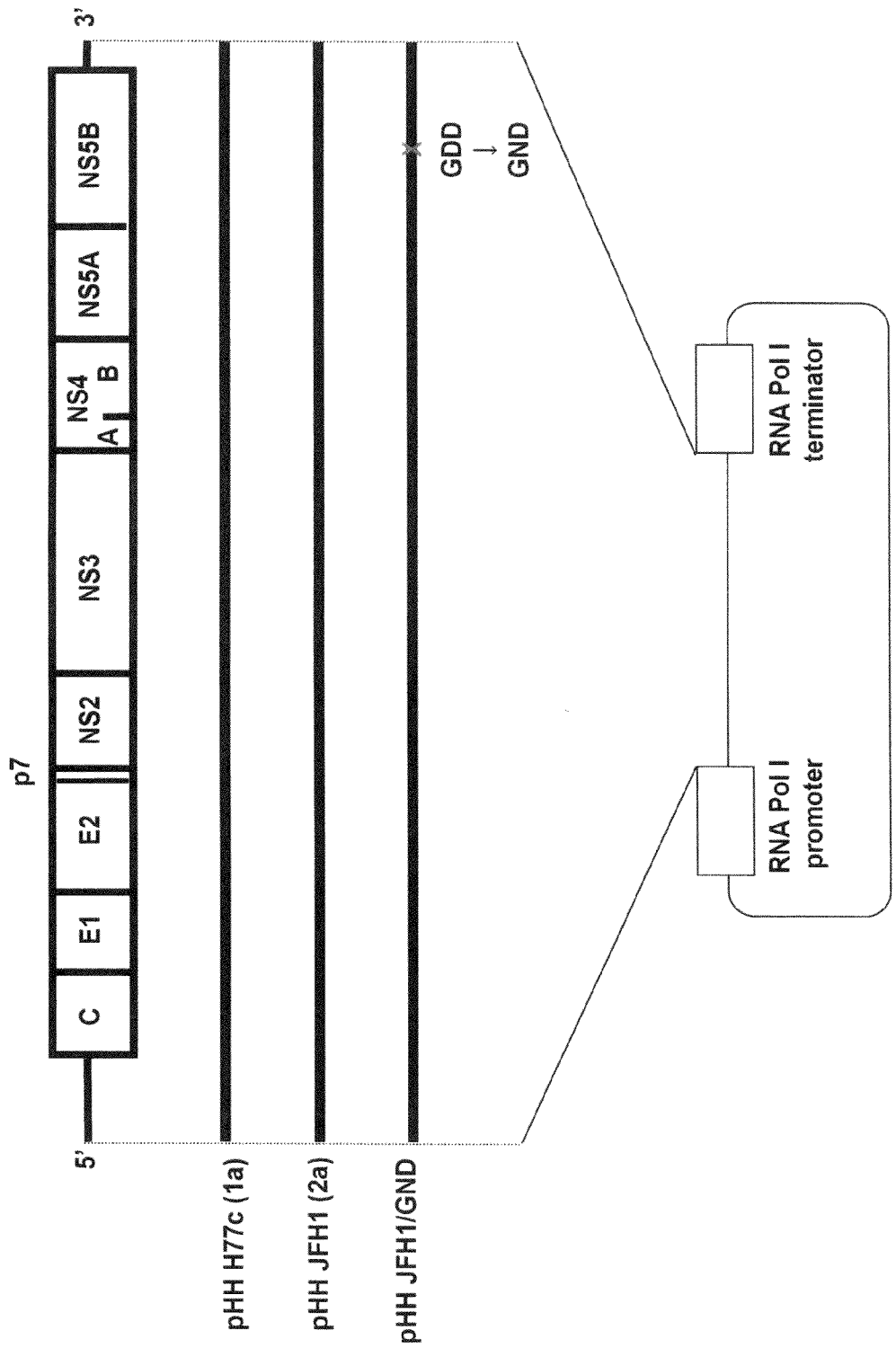
FIG. 1B shows maps of pHH H77c, pHH JFH1, and pHH JFH1/GND.

A restriction enzyme BsmBI recognition sequence was added to the 5' end and the 3' end of each of the above HCV genomic cDNAs (JFH1, JFH1/GND, and H77c) by PCR. A BsmBI cleavage site is located at a distance from a BsmBI recognition site. With the utilization of such property, each HCV genome was inserted into the BsmBI site of a pHH21 vector having the human RNA polymerase I promoter sequence and the mouse RNA polymerase I terminator sequence (Neumann G. et al., Proc. Natl. Acad. Sci. USA, 96 (1999) pp. 9345-9350) without insertion of extra nucleotide sequences between the promoter/terminator and the HCV genome (FIG. 1A). In addition, FIG. 1B shows a map of the individual clones. The thus obtained vectors each comprising the relevant HCV genomic cDNA were designated as pHH JFH1, pHH JFH1/GND, and pHH H77c, respectively.

Further, chimeric HCV expression vectors derived from genomic cDNAs of J6CF and JFH1, those of H77c and JFH1, and those of J1 and JFH1 were produced in the manner described below.

Production of pHH J6(C-p7)/JFH1

A plasmid DNA pJFH1 constructed by cloning cDNA corresponding to the JFH1 strain-derived entire genomic RNA region into a pUC19 plasmid (Wakita, T. et al. Nat. Med., 11 (2005) pp. 791-796, WO 2004/104198) was digested with AgeI, followed by further partial digestion with BclI. And then, the resulting plasmid DNA fragment from which a fragment ranging from the AgeI site to the first BclI site (2672 bp) had been removed was purified. Meanwhile, a 2672-bp fragment obtained by partial digestion of J6CF-strain-derived genomic cDNA with AgeI and BclI was ligated to the above purified fragment to obtain pUC J6/JFH1.

Next, an approximately 4.3 kb of fragment obtained by digestion of pHH JFH1 with NocI and an approximately 8.2 kb of fragment obtained by digesting of pUC J6/JFH1 with NocI were ligated with a ligase to obtain an expression vector pHH J6(C-p7)/JFH1. The insert (J6(C-p7)JFH1; SEQ ID NO: 29, FIGS. 10A to 10D) in pHH J6(C-p7)/JFH1 comprises a chimeric 5' untranslated region derived from those of the JFH1 and J6CF strains; DNA sequences encoding Core protein, E1 protein, E2 protein, and p7 protein derived from the J6CF strain; and DNA sequences encoding NS2, NS3, NS4A, NS4B, NS5A, and NS5B proteins and a 3' untranslated region derived from the JFH1 strain.

Production of pHH H77c(C-p7)/JFH1

To the above JFH1 genomic cDNA as a template, 10× buffer (5 μl) and 2.5 mM dNTP mixture (5 μl) which were attached to an LA-PCR kit (Takara Bio Inc.), and 10 μM primers 5-JFH-S (SEQ ID NO: 10: GCCATGGCGTTAG-TATGAGTGTCGT) and 5-JFH-A (SEQ ID NO: 11: TCGT-GCTCATGGTGCACGGTCTACGAGACC) (1 μl each) were added and then deionized water was added up to a final total volume of 49 μl. Subsequently, Takara LA Taq (Takara Bio Inc.) (1 μl) was added thereto, followed by a PCR reaction. The PCR reaction was carried out under conditions of 30 cycles of 94° C. for 1 minute, 64° C. for 2 minutes, and 72° C. for 3 minutes. The thus obtained PCR product was designated as a PCR product no. 1. Then, to the JFH1 genomic cDNA as a template, 10× buffer (5 μl) and 2.5 mM dNTP mixture (5 μl) which were attached to an LA-PCR kit (Takara Bio Inc.), and 10 μM primers 3-JFH-S (SEQ ID NO: 12: GGCATACG-CATATGACGCACCTGTGCACGG) and 3-JFH-A (SEQ ID NO: 13: GCTCTGACGAAGTACGGCACATGTGTC) (1 μl each) were added, and then, deionized water was added up to a final total volume of 49 μl. Subsequently, Takara LA Taq (Takara Bio Inc.) (1 μl) was added thereto, followed by a PCR reaction. The PCR reaction was carried out under conditions of 25 cycles of 94° C. for 1 minute, 64° C. for 2 minutes, and 72° C. for 3 minutes. The thus obtained PCR product was designated as a PCR product no. 2. Further, to the above H77c genomic cDNA as a template, 10× buffer (5 μl), and 2.5 mM dNTP mixture (5 μl) which were attached to an LA-PCR kit (Takara Bio Inc.), and 10 μM primers 5-H77-S (SEQ ID NO: 14: ACCGTGCACCATGAGCACGAATCCTAAACC) and 5-H77-A (SEQ ID NO: 15: GAAGCCGCACGTAAGGG-TATCGATG) (1 μl each) were added, and then, deionized water was added up to a final total volume of 49 μl. Subsequently, Takara LA Taq (Takara Bio Inc.) (1 μl) was added thereto, followed by a PCR reaction. The PCR reaction was carried out under conditions of 25 cycles of 94° C. for 1 minute, 64° C. for 2 minutes, and 72° C. for 3 minutes. The thus obtained PCR product was designated as a PCR product no. 3. Then, to the H77c genomic cDNA as a template, 10× buffer (5 μl) and 2.5 mM dNTP mixture (5 μl) which were attached to an LA-PCR kit (Takara Bio Inc.), and 10 μM primers 3-H77-S (SEQ ID NO: 16: CATTGTGCCCG-CAAAGAGCGTGTGT) and 3-H77-A (SEQ ID NO: 17: GTGCGTCATATGCGTATGCCCGCTGAGGCA) (1 μl each) were added, and then, deionized water was added up to a final total volume of 49 μl. Subsequently, Takara LA Taq (Takara Bio Inc.) (1 μl) was added thereto, followed by a PCR reaction. The PCR reaction was carried out under conditions of 25 cycles of 94° C. for 1 minute, 64° C. for 2 minutes, and 72° C. for 3 minutes. The thus obtained PCR product was designated as a PCR product no. 4.

Next, each PCR product was purified and dissolved in 50 µl of H$_2$O. DNAs of PCR products nos. 1 and 3 were separately 100-fold diluted and 1 µl of each were mixed together. The resulting mixture was used as a template and PCR was carried out for 5 cycles under the above conditions without the addition of primers. Thereafter, primers 5-JFH-S (SEQ ID NO: 10) and 5-H77-A (SEQ ID NO: 15) were added thereto, followed by PCR for 25 cycles. The thus amplified chimeric DNA fragment was purified. The fragment was cloned into a plasmid vector pCRII. The proper nucleotide sequence was verified by sequencing the DNA fragment. This plasmid obtained by cloning the chimeric DNA fragment into pCRII was designated as pCR5HJ. Further, PCR products nos. 2 and 4 were separately 100-fold diluted and 1 µl of each were mixed together. The resulting mixture was used as a template and PCR was carried out for 5 cycles under the above conditions without the addition of primers. Thereafter, primers 3-H77-S (SEQ ID NO: 16) and 3-JFH-A (SEQ ID NO: 13) were added thereto, followed by PCR for 25 cycles. The thus amplified chimeric DNA fragment was purified. The fragment was cloned into a plasmid vector pCRII. The proper nucleotide sequence was verified by sequencing the DNA fragment. This plasmid obtained by cloning the chimeric DNA fragment into pCRII was designated as pCR3HJ.

Next, pCR5HJ was digested with restriction enzymes AgeI and KpnI, H77c genomic cDNA was digested with restriction enzymes KpnI and AscI, and pCR3HJ was digested with restriction enzymes AscI and NotI. Each HCV cDNA fragment was fractionated by agarose gel electrophoresis and purified. The three DNA fragments above were ligated to a vector obtained by digesting pHH JFH1 with AgeI and NotI. The vector was designated as pHH H77c(C-p7)/JFH. The insert (H77c(C-p7)JFH; SEQ ID NO: 30, FIGS. 11A to 11D) in the expression vector pHH H77c(C-p7)/JFH comprises the chmeric 5' untranslated region derived from those of the JFH1 and H77c strains; DNA sequences encoding Core protein, E1 protein, E2 protein, and p7 protein, which are derived from the H77c strain; and DNA sequences encoding NS2, NS3, NS4A, NS4B, NS5A, and NS5B proteins and the 3' untranslated region, which are derived from the JFH1 strain.

Production of pHH J1(C-p7)/JFH1

To the above JFH1 genomic cDNA as a template, 10× buffer (5 µl) and 2.5 mM dNTP mixture (5 µl) which were attached to an LA-PCR kit (Takara Bio Inc.), and 10 µM primers 5-JFH-S (SEQ ID NO: 10: GCCATGGCGTTAG-TATGAGTGTCGT) and 5-JFH-A2 (SEQ ID NO: 18: TTGT-GCTCATGGTGCACGGTCTACGAGACC) (1 µl each) were added, and then, deionized water was added up to a final total volume of 49 µl. Subsequently, Takara LA Taq (Takara Bio Inc.) (1 µl) was added thereto, followed by a PCR reaction. The PCR reaction was carried out under conditions of 25 cycles of 94° C. for 1 minute, 64° C. for 2 minutes, and 72° C. for 3 minutes. The thus obtained PCR product was designated as a PCR product no. 5.

Next, to the JFH1 genomic cDNA as a template, 10× buffer (5 µl) and 2.5 mM dNTP mixture (5 µl) which were attached to an LA-PCR kit (Takara Bio Inc.), and 10 µM primers 3-JFH-S2 (SEQ ID NO: 19: AGCTTACGCCTATGACG-CACCTGTGCACGG) and 3-JFH-A (SEQ ID NO: 13: GCTCTGACGAAGTACGGCACATGTGTC) (1 µl each) were added, and then, deionized water was added up to a final total volume of 49 µl. Subsequently, Takara LA Taq (Takara Bio Inc.) (1 µl) was added thereto, followed by a PCR reaction. The PCR reaction was carried out under conditions of 25 cycles of 94° C. for 1 minute, 64° C. for 2 minutes, and 72° C. for 3 minutes. The thus obtained PCR product was designated as a PCR product no. 6.

To cDNA corresponding to the genomic RNA derived from the J1 strain of genotype 1b (GenBank accession no. D89815, Aizaki, H. et al. Hepatology, 27 (1998) pp. 621-627) as a template, 10× buffer (5 µl) and 2.5 mM dNTP mixture (5 µl) which were attached to an LA-PCR kit (Takara Bio Inc.), and 10 µM primers 5-J1-S (SEQ ID NO: 20: ACCGTGCACCAT-GAGCACAAATCCTAAACC) and 5-J1-A (SEQ ID NO: 21: AAGCGGGATGTACCCCATGAG) (each 1 µl) were added, and then, deionized water was added up to a final total volume of 49 µl. Subsequently, Takara LA Taq (Takara Bio Inc.) (1 µl) was added thereto, followed by a PCR reaction. The PCR reaction was carried out under conditions of 25 cycles of 94° C. for 1 minute, 64° C. for 2 minutes, and 72° C. for 3 minutes. The thus obtained PCR product was designated as a PCR product no. 7.

Next, to the above J1 strain-derived genomic cDNA as a template, 10× buffer (5 µl) and 2.5 mM dNTP mixture (5 µl) which were attached to an LA-PCR kit (Takara Bio Inc.), and 10 µM primers 3-J1-S (SEQ ID NO: 22: CGGCTGTACATG-GATGAATAGCACTGGGTT) and 3-J1-A (SEQ ID NO: 23: GTGCGTCATAGGCGTAAGCTCGTGGTGGTA) (1 µl each) were added, and then, deionized water was added up to a final total volume of 49 µl. Subsequently, Takara LA Taq (Takara Bio Inc.) (1 µl) was added thereto, followed by a PCR reaction. The PCR reaction was carried out under conditions of 25 cycles of 94° C. for 1 minute, 64° C. for 2 minutes, and 72° C. for 3 minutes. The thus obtained PCR product was designated as a PCR product no. 8.

Next, each PCR product was purified and dissolved in 50 µl of H$_2$O. DNAs of PCR products nos. 5 and 7 were separately 100-fold diluted and 1 µl of each were mixed together. The resulting mixture was used as a template and PCR was carried out for 5 cycles under the above conditions without the addition of primers. Thereafter, primers 5-JFH-S (SEQ ID NO: 10) and 5-J1-A (SEQ ID NO: 21) were added thereto, followed by PCR for 25 cycles. The thus amplified chimeric DNA fragment was purified. The fragment was cloned into a plasmid vector pCRII. The nucleotide sequence was verified by sequencing the DNA fragment. The plasmid obtained by cloning the chimeric DNA fragment into pCRII was designated as pCR5JJ.

Further, DNAs of PCR products nos. 6 and 8 were separately 100-fold diluted and 1 µl of each were mixed together. The resulting mixture was used as a template and PCR was carried out for 5 cycles under the above conditions without the addition of primers. Thereafter, primers 3-J1-S (SEQ ID NO: 22) and 3-JFH-A (SEQ ID NO: 13) were added thereto, followed by PCR for 25 cycles. The thus amplified chimeric DNA fragment was purified. The fragment was cloned into a plasmid vector pCRII. The proper nucleotide sequence was verified by sequencing the DNA fragment. The plasmid obtained by cloning the chimeric DNA fragment into pCRII was designated as pCR3JJ.

pCR5JJ was digested with restriction enzymes AgeI and ClaI, J1 genomic cDNA was digested with restriction enzymes ClaI and AvrII, and pCR3JJ was digested with restriction enzymes AvrII and KpnI. Each HCV cDNA fragment was fractionated by agarose gel electrophoresis and purified. The above three DNA fragments were ligated to a vector obtained by digesting pHH JFH1 with AgeI and KpnI. The vector was designated as pHH J1(C-p7)/JFH. The insert (J1(C-p7)JFH; SEQ ID NO: 31, FIG. 12A to D) in the expression vector pHH J1(C-p7)/JFH comprises the chimeric 5' untranslated region derived from those of the JFH1 and J1 strains; DNA sequences encoding Core protein, E1 protein, E2 protein, and p7 protein, which are derived from the J1 strain; and DNA sequences encoding NS2, NS3, NS4A, NS4B, NS5A, and NS5B proteins and the 3' untranslated region, which are derived from the JFH1 strain.

Production of pHH J1(C-NS2)/JFH1

To the above JFH1 genomic cDNA as a template, 10× buffer (5 μl) and 2.5 mM dNTP mixture (5 μl) which were attached to an LA-PCR kit (Takara Bio Inc.), and 10 μM primers 5-JFH-S (SEQ ID NO: 10: GCCATGGCGTTAG-TATGAGTGTCGT) and 5-JFH-A2 (SEQ ID NO: 18: TTGT-GCTCATGGTGCACGGTCTACGAGACC) (1 μl each) were added, and then, deionized water was added up to a final total volume of 49 μl. Subsequently, Takara LA Taq (Takara Bio Inc.) (1 μl) was added thereto, followed by a PCR reaction. The PCR reaction was carried out under conditions of 25 cycles of 94° C. for 1 minute, 64° C. for 2 minutes, and 72° C. for 3 minutes. The thus obtained PCR product was designated as a PCR product no. 9.

Next, to the JFH1 genomic cDNA as a template, 10× buffer (5 μl) and 2.5 mM dNTP mixture (5 μl) which were attached to an LA-PCR kit (Takara Bio Inc.), and 10 μM primers 3-JFH-NS3-S (SEQ ID NO: 24: GCGACTCCTTGCTC-CCATCACTGCTTATGC) and 3-JFH-NS3-A (SEQ ID NO: 25: TGGGAGACCTTGTAACAACGTCGAGTGT) (1 μl each) were added, and then, deionized water was added up to a final total volume of 49 μl. Subsequently, Takara LA Taq (Takara Bio Inc.) (1 μl) was added thereto, followed by a PCR reaction. The PCR reaction was carried out under conditions of 25 cycles of 94° C. for 1 minute, 64° C. for 2 minutes, and 72° C. for 3 minutes. The thus obtained PCR product was designated as a PCR product no. 10.

To cDNA of the genomic RNA derived from the J1 strain of genotype 1b (GenBank accession no. D89815, Aizaki, H. et al. Hepatology, 27 (1998) pp. 621-627) as a template, 10× buffer (5 μl) and 2.5 mM dNTP mixture (5 μl) which were attached to an LA-PCR kit (Takara Bio Inc.), and 10 μM primers 5-J1-S (SEQ ID NO: 20: ACCGTGCACCATGAG-CACAAATCCTAAACC) and 5-J1-A (SEQ ID NO: 21: AAGCGGGATGTACCCCATGAG) (1 μl each) were added, and then, deionized water was added up to a final total volume of 49 μl. Subsequently, Takara LA Taq (Takara Bio Inc.) (1 μl) was added thereto, followed by a PCR reaction. The PCR reaction was carried out under conditions of 25 cycles of 94° C. for 1 minute, 64° C. for 2 minutes, and 72° C. for 3 minutes. The thus obtained PCR product was designated as a PCR product no. 11.

Next, to J1 strain-derived genomic cDNA as a template, 10× buffer (5 μl) and 2.5 mM dNTP mixture (5 μl) which were attached to an LA-PCR kit (Takara Bio Inc.), and 10 μM primers 3-J1-S (SEQ ID NO: 22: CGGCTGTACATGGAT-GAATAGCACTGGGTT) and 3-J1-NS3-A (SEQ ID NO: 26: CATAAGCAGTGATGGGAGCAAGGAGTCGCC) (1 μl each) were added, and then, deionized water was added up to a final total volume of 49 μl. Subsequently, Takara LA Taq (Takara Bio Inc.) (1 μl) was added thereto, followed by a PCR reaction. The PCR reaction was carried out under conditions of 25 cycles of 94° C. for 1 minute, 64° C. for 2 minutes, and 72° C. for 3 minutes. The thus obtained PCR product was designated as a PCR product no. 12.

Each PCR product was purified and dissolved in 50 μl of H₂O. DNAs of PCR products nos. 9 and 11 were separately 100-fold diluted and 1 μl of each were mixed together. The resulting mixture was used as a template and PCR was carried out for 5 cycles under the above conditions without the addition of primers. Thereafter, primers 5-JFH-S (SEQ ID NO: 10) and 5-J1-A (SEQ ID NO: 21) were added thereto, followed by PCR for 25 cycles. The thus amplified chimeric DNA fragment was purified. The fragment was cloned into a plasmid vector pCRII. The proper nucleotide sequence was verified by sequencing the DNA fragment. The plasmid obtained by cloning the chimeric DNA fragment into pCRII was designated as pCR5JJ.

Further, DNAs of PCR products nos. 10 and 12 were separately 100-fold diluted and 1 μl of each were mixed together. The resulting mixture was used as a template and PCR was carried out for 5 cycles under the above conditions without the addition of primers. Thereafter, primers 3-J1-S (SEQ ID NO: 22) and 3-JFH-NS3-A (SEQ ID NO: 25) were added thereto, followed by PCR for 25 cycles. The thus amplified chimeric DNA fragment was purified. The fragment was cloned into a plasmid vector pCRII. The proper nucleotide sequence was verified by sequencing the DNA fragment. The plasmid obtained by cloning the chimeric DNA fragment into pCRII was designated as pCR3JJNS3.

pCR5JJ was digested with restriction enzymes AgeI and ClaI, J1 genomic cDNA was digested with restriction enzymes ClaI and AvrII, and pCR3JJNS3 was digested with restriction enzymes AvrII and BspDI. Each HCV cDNA fragment was fractionated by agarose gel electrophoresis and purified. The three DNA fragments above were ligated to a vector obtained by digesting pHH JFH1 with AgeI and BspDI. The vector was designated as pHH J1(C-NS2)/JFH. The insert (J1(C-NS2)JFH; SEQ ID NO: 32, FIG. 13A to D) in the expression vector pHH J1(C-NS2)/JFH comprises the chimeric 5' untranslated region derived from those of the JFH1 and J1 strains; DNA sequences encoding Core protein, E1 protein, E2 protein, p7 protein, and NS2 protein, which are derived from the J1 strain; and DNA sequences encoding NS3, NS4A, NS4B, NS5A, and NS5B proteins and the 3' untranslated region, which are derived from the JFH1 strain.

Figure 1C:
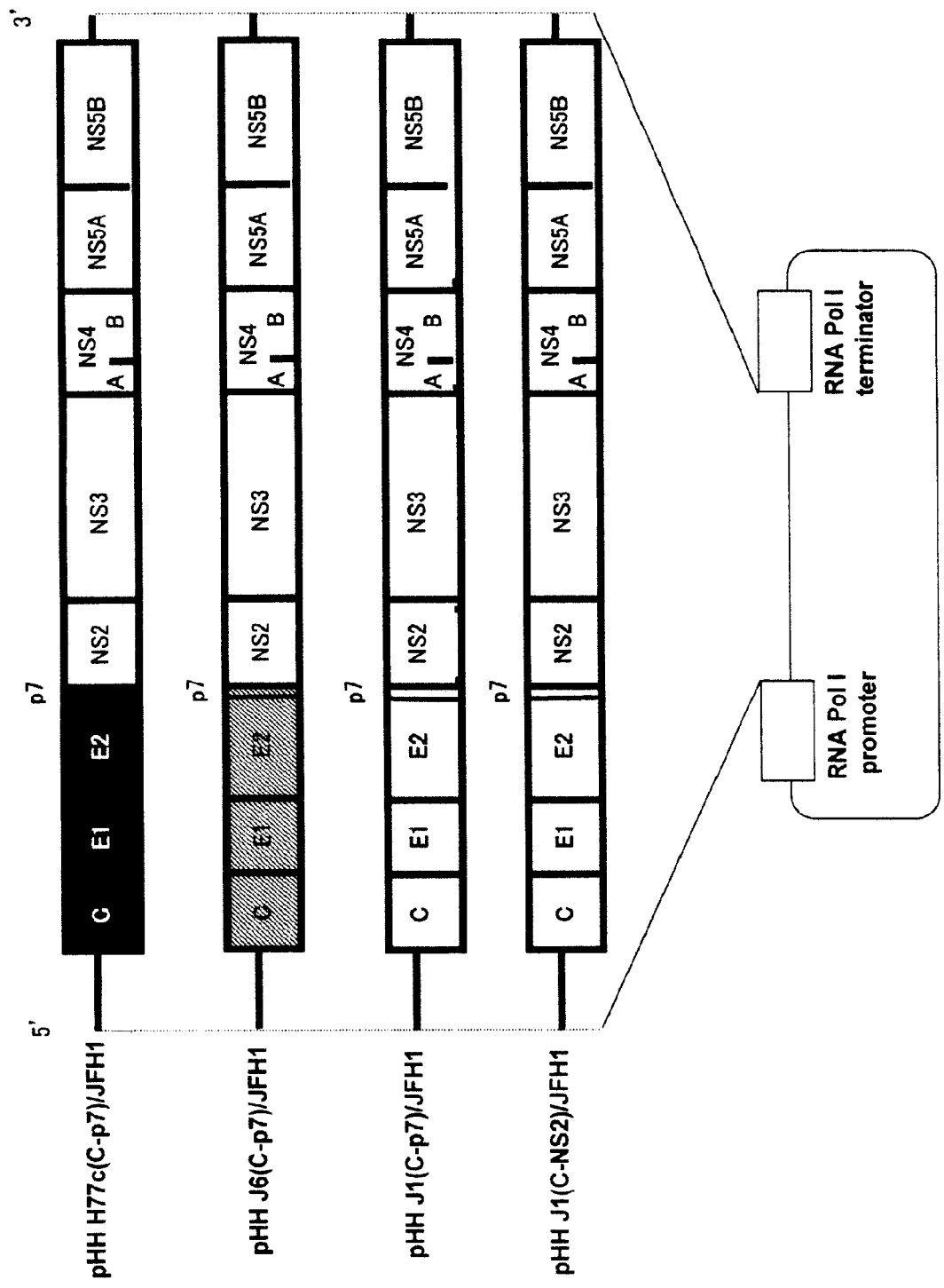
FIG. 1C shows maps of pHH H77c(C-p7)/JFH1, pHH J6(C-p7)/JFH1, pHH J1(C-p7)/JFH1, and pHH J1(C-NS2)/JFH1.

FIG. 1C shows a map of the individual clones.

Example 2

Confirmation of Intracellular HCV RNA Synthesis pHH JFH1 and pHH JFH1/GND produced in Example 1 were introduced into Huh7 and HepG2 cells using Fugene 6 (Roche) in accordance with the attached manufacturer's instructions. 24 hours later, RNA was prepared from each cell with Isogen (Nippon Gene Co., Ltd.) in accordance with the attached manufacturer's instructions.

As described below, it was confirmed whether or not HCV RNA was synthesized from pHH JFH1 and pHH JFH1/GND by the RACE method using the obtained RNAs as templates.

2 μg each RNA prepared above were separately ligated to 2.5 μM RNA linker (SEQ ID NO: 1: GCUGAUGGC-GAUGAAUGAACACUGCGUUUGCUGGCU-UUGAUGAAA) with T4 RNA ligase (Takara) and an attached buffer. Then, cDNA synthesis was carried out with RNA linker-ligated RNA as a template, a primer (SEQ ID NO: 2: gtacccatgaggtcggcaaag) complementary to HCV RNA, and the SuperScript III reverse-transcription enzyme (Invitrogen Corporation) in accordance with the attached manufacturer's instructions.

Next, DNA amplification was carried out by PCR using each synthesized cDNA described above as a template and two types of primers, which were a 5' end sense primer (SEQ ID NO: 3: GCTGATGGCGATGAATGAACACTG) for RNA linker and a 3' end antisense primer (SEQ ID NO: 4:gaccgctccgaagttttccttg). Further, a second PCR step was carried out with each amplified DNA as a template and a primer set of a 5' end primer (SEQ ID NO: 5:GAACACT-GCGTTTGCTGGCTTTGATG) and a 3' end primer (SEQ ID NO: 6: cgccctatcaggcagtaccacaag) corresponding to the inside sequence of the amplified DNA. This PCR was carried out with a commercially available kit, Ex Taq kit (Takara) as follows: heating treatment at 96° C. for 5 minutes; 35 cycles of 96° C. for 1 minute, 55° C. for 1 minute, and 72° C. for 2 minutes; and preservation at 4° C. Subsequently, in order to confirm the production of the $2^{nd}$ PCR product, a portion of the reaction solution was subjected to agarose gel electrophoresis for confirmation. As a result (FIG. 2), it was confirmed that HCV RNA transcription from pHH JFH1 and pHH JFH1/GND took place in both Huh7 and HepG2 cells. Further, each $2^{nd}$ PCR product was cloned into a pGEM-T Easy vector (Promega). The nucleotide sequence of the cloned DNA in the obtained plasmid DNA was determined with a DNA sequencer (ABI PRISM 377). As a result, the 5' end sequence of HCV RNA transcribed from pHH JFH1 and that transcribed from pHH JFH1/GND were found to be identical to the 5' end sequence of the HCV genome. FIG. 3 shows the 5' end sequence of HCV RNA transcribed from pHH JFH1 and the linker sequence.

Example 3

Confirmation of Intercellular HCV Protein Expression

It was confirmed whether or not HCV protein translation took place following transcription in cells into which pHH JFH1, pHH H77c, and pHH JFH1/GND had been separately introduced, as described below.

pHH JFH1, pHH H77c, and pHH JFH1/GND were separately introduced into Huh7 cells using Fugene 6 (Roche) in accordance with the attached manufacturer's instructions. On the 4th day after culture, cell extracts were prepared by a conventional method. Then, proteins in the extracts were analyzed by SDS-PAGE and the Western blot method. Upon analysis, a cell extract obtained by transiently transfecting expression plasmid DNA containing the Core gene into a Huh7 cell was used as a positive control. Further, a cell extract obtained from an untransfected Huh7 cell was used as a negative control. A sample extracted from each cell clone was subjected to SDS-PAGE, followed by blotting on a PVDF membrane (Immobilon-P, Millipore). The Core protein and the NS5A protein translated in each cell that had been blotted on the membrane were detected using ECL (Amersham Pharmacia) with an anti-Core-specific antibody (rabbit polyclonal antibody), a mouse monoclonal antibody (Austral) as an anti-NS5A antibody, and HRP-labeled secondary antibodies capable of recognizing the above antibodies.

Consequently, as shown in FIG. 4, Core protein expression and NS5A protein expression were confirmed in the cell into which pHH JFH1 had been introduced. However, these protein expressions were not detected in the cells into which pHH H77c and pHH JFH1/GND had been separately introduced. The results were thought to indicate that in the cell into which pHH JFH1 had been introduced, RNA was transcribed from pHH JFH1 and intracellularly replicated and then protein translation took place to produce detectable levels of the proteins; while, in the cell into which pHH JFH1/GND had been introduced, RNA was transcribed from pHH JFH1/GND and but not intracellularly replicated because of a mutation of NS5B thereof, and, as a result, the proteins were not produced at detectable levels. It is unclear why HCV protein expression from pHH H77c was not detected, although HCV genomic RNA is autonomously replicated in culture cells (Yi, M. & Lemon S T., J. Virol., 78 (2004) pp. 7904-7915).

Next, examination took place to identify the cell lines in which HCV protein expression could be caused. pHH JFH1 and pHH JFH1/GND were introduced together with a GFP expression vector into Huh7, RCYM1RC, 5-15RC, HepG2, and 293T cells (pGreenLantern: Life Technologies Inc.) with Fugen 6 (Roche) in accordance with the attached manufacturer's instructions. On the 4th day after introduction, GFP expression was observed with a fluorescence microscope so that introduction of each vector was confirmed. Then, a cell extract was prepared from each cell. Subsequently, the Core protein in each extract was analyzed by SDS-PAGE and the Western blot method. The Core protein was detected using ECL (Amersham Pharmacia) with an anti-Core-specific rabbit polyclonal antibody and an HRP-labeled secondary antibody capable of recognizing the antibody. As a result, as shown in FIG. 5, the Core protein was detected in Huh7, RCYM1RC, 5-15RC, and HepG2 cells.

Example 4

Production of HCV Particles

Next, in order to confirm whether or not HCV particles would be produced by a cell into which pHH JFH1 had been introduced, the Core protein in a culture supernatant was analyzed. pHH JFH1 and, as a control, a vector pCAG327JFH1 expressing Core protein, E1, E2 and p7 were separately introduced into HepG2 cells using Fugene 6. On the 2nd day after introduction, each culture supernatant was removed, followed by the addition of a fresh medium and further culturing for 2 days. Thereafter, cells and culture solutions were collected, followed by protein extraction from the cells. The Core protein expression in each cell was analyzed by the method shown in Example 3. As a result, the Core protein expression was confirmed (FIG. 6A). In order to confirm the presence of HCV particles in the culture solution, the culture solution was fractionated through a sucrose density gradient. A culture supernatant (0.2 ml) of each sample was overlayered on 10% to 60% (wt/wt) sucrose density gradient solutions (each dissolved in 50 mM Tris pH 7.5/0.1 M NaCl/l mM EDTA). This was centrifuged in a Beckman rotor S W41E at 35,000 RPM and 4° C. for 16 hours. After centrifugation, the fractions of 0.5 ml each were collected from the bottom of the centrifuge tube. The density and the HCV core protein concentration of each fraction were quantified. The HCV core protein was assayed by the Ortho HCV antigen IRMA test (Aoyagi et al., J. Clin. Microbiol., 37 (1999) pp. 1802-1808).

As shown in FIG. 6B, the Core protein peak was observed in fractions at 1.15 and 1.18 mg/ml. In contrast, in the case of the cell expressing Core protein, E1, E2, and p7, the Core protein peak was not observed.

If Core protein and HCV RNA found in fractions at 1.15 to 1.18 mg/ml form an HCV particle structure, such particles would be sensitive to surfactant NP40 treatment. Thus, a culture solution obtained 2 to 4 days after introduction of pHH JFH1 into HepG2 was treated with 0.2% NP40 for 20 minutes, followed by fractionation through a sucrose density gradient. As shown in FIG. 7, the Core protein peak was observed in a fraction at 1.20 mg/ml as a result of NP40 treatment. That is, it was considered that NP40 treatment caused a lipid-containing surface membrane having a light specific gravity to become detached from a virus particle such that a Core particle having no virus-like structure that consists of nucleic acid and the Core protein was obtained, such particle having a heavier specific gravity.

Based on the above results, it was confirmed that introduction of pHH JFH1 into a HepG2 cell resulted in transcription of viral RNA from the HCV genomic cDNA, followed by viral protein synthesis and viral RNA replication, and thus virus particles were formed and secreted in a culture solution.

Example 5

Confirmation of Infectivity of HCV Particles

It was examined whether or not HCV particles obtained in Example 4 would be infectious. pHH JFH1 was introduced into each of Huh7 and HepG2 cells using Fugene 6. Culture supernatants cultured for 3 to 5 days were 30-fold concentrated with an ultrafilter membrane (cut off: $1\times10^5$ Da). Then, Huh7.5.1 cells were cultured on 15-mm coverslips in the concentrated culture solutions (100 μl each) containing HCV particles. On the 4th day, the cells were fluorescent-stained with an anti-NS5A antibody. Anti-NS5A antibody-staining-positive cells (namely, infected cells) were counted. As a result, as shown in FIG. 8, some infected cells were observed. Based on the results, HCV particles secreted in the culture solution as a result of introduction of pHH JFH1 into Huh7 or HepG2 cells were confirmed to exhibit infectivity.

Example 6

Obtaining an Infectious HCV Particle-Producing Cell Line

With the use of the system shown in the above Examples, it was attempted to establish a cell line that continuously produces infectious HCV particles.

A vector was produced by digesting pHH JFH1 with NheI and incorporating into the digested site an expression unit (SV40 promotor/Zeo/polyA) obtained by ligating the Zeocin-resistant gene downstream of an SV40 promoter that had been obtained by digesting pSV40/Zeo2 (Invitrogen) with NheI and XbaI and ligating an SV40 polyA addition signal further downstream thereof. The obtained vector was designated as pHH/ZeoJFH1 (FIG. 9).

pHH/ZeoJFH1 was introduced into HepG2 cells using Fugene 6, followed by culture in a Zeocin-containing medium. Then, culture in a Zeocin-containing medium was continued, with a culture solution being exchanged twice a week. The viable cell colony found in a culture dish prepared on the $21^{st}$ day of culture was cloned. Then, culture was continued. As a result of such colony cloning, 100 cell clones were obtained. The Core protein amount in a culture supernatant of such a clone was determined by the Ortho HCV antigen IRMA test (Aoyagi et al., J. Clin. Microbiol., 37 (1999) p. 1802-1808). A HepG2/No59 cell clone having a high Core protein expression level was selected.

HepG2/No59 cells ($2\times10^6$ cells) were cultured in a medium (8 ml) with a 10-cm dish. 48 hours later, the culture supernatant was collected.

As a result of assay of the Core protein in the culture supernatant, the HepG2/No59 cell was found to produce 1,400 fmol/L of Core protein.

In addition, RNA prepared from the culture supernatant was subjected to measurement of HCV genomic RNA amount. HCV RNA was detected by quantitative RT-PCR according to the method of Takeuchi et al. (Takeuchi T. et al., Gastroenterology, 116 (1999) pp. 636-642), during which RNA in the 5' untranslated region of HCV RNA was detected. Specifically, HCV RNA contained in RNA extracted from cells was subjected to PCR amplification with the following synthesis primers and an EZ rTth RNA PCR kit (Applied Biosystems), followed by detection with an ABI Prism 7700 sequence detector system (Applied Biosystems).

```
R6-130-S17:
5'-CGGGAGAGCCATAGTGG-3'        (SEQ ID NO: 7)

R6-290-R19:
5'-AGTACCACAAGGCCTTTCG-3'      (SEQ ID NO: 8)

TaqMan Probe, R6-148-S21FT:
5'-CTGCGGAACCGGTGAGTACAC-3'    (SEQ ID NO: 9)
```

The results showed that there were $6.1\times10^8$ copies/ml of HCV RNA in the HepG2/No59 cell culture supernatant. Such production amount was approximately 60 times as large as those reported in the past.

Further, the HepG2/No59 cell culture supernatant was 30-fold concentrated with an ultrafilter membrane (cut off: $1\times10^5$ Da). Then, Huh7.5.1 cells were cultured on 15-mm coverslips in the concentrated culture solution (100 μl) containing HCV particles. On the 4th day, the cells were immunostained with an anti-NS5A antibody. As a result, Anti-NS5A antibody-staining-positive cells, namely infected cells, were detected. Accordingly, HCV particles secreted in a HepG2/No59 cell culture solution were confirmed to exhibit infectivity.

Example 7

Production of HCV Particles with Chimeric HCV Expression Vectors

Chimeric HCV expression vectors pHH H77c(C-p7)/JFH1, pHH J6(C-p7)/JFH1, pHH J1(C-p7)/JFH1, and pHH J1(C-NS2)/JFH1 produced in Example 1 were introduced into Huh7.5.1 cells, which were of an established cell line derived from a Huh7 cell (Zhong, J. et al., Proc. Natl. Acad. Sci USA, 102, 9294-9299, (2005)) using Fugene 6 (Roche) in accordance with the attached manufacturer's instructions. On the $3^{rd}$ day after introduction, the culture supernatants were collected, followed by measurement of the Core protein amount in the culture supernatants. The Core protein amount was measured by the Ortho HCV antigen IRMA test (Aoyagi et al., J. Clin. Microbiol., 37 (1999) pp. 1802-1808). A culture supernatant of a cell into which no vectors had been introduced was used as a negative control. A culture supernatant of a cell into which pHH JFH1 had been introduced was used as a positive control. Table 1 shows examples of the above experimental results. The Core protein was observed in each cell supernatant of cells into which a different chimeric HCV expression vector had been introduced, and therefore it was determined that virus particles were produced. In addition, pHH J6(C-p7)/JFH1 was found to have HCV production ability at a level at least 10 times higher than that of pHH JFH1.

TABLE 1

| Expression vector | Core protein amount 3 days after vector introduction (fmol/L) |
|---|---|
| No introduction | 0 |
| pHH JFH1 | 252.164 |
| pHH J6(C-p7)/JFH1 | 2272.878 |
| pHH H77c(C-p7)/JFH1 | 29.555 |
| pHH J1 (C-p7)/JFH1 | 0.403 |
| pHH J1 (C-NS2)/JFH1 | 11.004 |

Example 8 pHH J6(C-p7)/JFH1 and pHH J1(C-p7)/JFH1 were introduced into Huh7.5.1 cells in the manner described in Example 7. The culture supernatants obtained on the 3$^{rd}$ day after introduction were concentrated with an ultrafilter membrane (cut off: 1×10$^5$ Da). Then, each the concentrated culture supernatant (100 μl) containing HCV particles was added to Huh7.5.1 cells, followed by culture on 15-mm coverslips. On the 4th day, the cells were immunostained with an anti-NS5A antibody. As a result, cells strongly stained with the anti-NS5A antibody were found among cells treated with the culture supernatant obtained from the cells into which pHH J6(C-p7)/JFH1 had been introduced. In contrast, cells treated with the culture supernatant obtained from the cells into which pHH J1(C-p7)/JFH1 had been introduced were clearly stained when compared with control cells, although the intensity of staining with an anti-NS5A antibody in the case of pHH J1(C-p7)/JFH1 was weaker than that in the case of pHH J6(C-p7)/JFH1. Accordingly, it was revealed that infectious HCV was produced in cells into which pHH J6(C-p7)/JFH1 and pHH J1(C-p7)/JFH1 had been introduced.

In addition, pHH/Zeo J1(C-p7)/JFH1 was produced by inserting a Zeocin-resistant gene expression unit into pHH J1(C-p7)/JFH1 in the manner described in Example 6. Then, pHH/Zeo J1(C-p7)/JFH1 was introduced into Huh7.5.1 such that cells capable of stably expressing virus particles and of propagating in a Zeocin-containing medium were obtained. The culture supernatant (8 ml) of such cells was concentrated with an ultrafilter membrane (cut off: 1×10$^5$ Da). The HCV core protein amount in the concentrated culture supernatant was 2365 fmol/L. Huh7.5.1 was infected with the concentrated culture supernatant (100 μl). On the 4$^{th}$ day, cells were immunostained with an anti-NS5A antibody. As a result, cells strongly stained with anti-NS5A antibody were found among cells treated with the culture supernatant obtained from stable expression cells into which pHH/Zeo J1(C-p7)/JFH1 had been introduced. Accordingly, it was revealed that infectious HCV was produced from the above cells.

It was shown that a chimeric HCV expression vector as described above can produce infectious HCV in cells infected therewith.

Free Text of Sequence Listing
The sequence of SEQ ID NO: 1 refers to synthetic RNA.
The sequences of SEQ ID NO: 2 to SEQ ID NO: 9 refer to synthetic DNAs.
The sequences of SEQ ID NOS: 10 to 26 refer to primers.
The sequences of SEQ ID NOS: 29 to 32 refer to chimeric DNAs.
The sequences of SEQ ID NOS: 33 to 45 refer to synthetic DNAs.

The invention claimed is:

1. A method for producing infectious hepatitis C virus (HCV) particles, comprising the step of introducing the following expression vector i) or ii) into a cell that is selected from the group consisting of Huh7, Huh7.5.1, and HepG2 cells:

i) an expression vector comprising: DNA sequences encoding the 5' untranslated region, Core protein, E1 protein, E2 protein, p7 protein, NS2 protein, NS3 protein, NS4A protein, NS4B protein, NS5A protein, and NS5B protein and the 3' untranslated region derived from the HCV JFH1 strain, downstream of an RNA polymerase I promoter; and DNA comprising an RNA polymerase I terminator, further downstream thereof; or ii) an expression vector comprising: DNA sequences encoding the 5' untranslated region, Core protein, E1 protein, E2 protein, and p7 protein derived from an HCV J6CF strain and DNA sequences encoding NS2, NS3, NS4A, NS4B, NS5A, and NS5B proteins and the 3' untranslated region derived from the HCV JFH1 strain, downstream of an RNA polymerase I promoter; and DNA containing an RNA polymerase I terminator, further downstream thereof.

2. The method according to claim 1, wherein said expression vector i) comprises the nucleotide sequence of SEQ ID NO: 27.

3. The method according to claim 1, wherein said expression vector ii) comprises the nucleotide sequence of SEQ ID NO: 29.

4. The method according to claim 1, wherein said expression vector i) is introduced into a HepG2 cell.

5. The method according to claim 1, wherein said expression vector ii) is introduced into a Huh7.5.1 cell.

* * * * *